United States Patent
Bejar et al.

(10) Patent No.: US 10,711,308 B2
(45) Date of Patent: Jul. 14, 2020

(54) MUTATION SIGNATURES FOR PREDICTING THE SURVIVABILITY OF MYELODYSPLASTIC SYNDROME SUBJECTS

(75) Inventors: Rafael Bejar, Boston, MA (US); Benjamin Levine Ebert, Boston, MA (US); Kristen Stevenson, Boston, MA (US); Donna Neuberg, Boston, MA (US)

(73) Assignees: BRIGHAM AND WOMEN'S HOSPITAL, INC., Boston, MA (US); DANA-FARBER CANCER INSTITUTE, INC., Boston, MA (US)

( * ) Notice: Subject to any disclaimer, the term of this patent is extended or adjusted under 35 U.S.C. 154(b) by 525 days.

(21) Appl. No.: 14/125,432

(22) PCT Filed: Jun. 15, 2012

(86) PCT No.: PCT/US2012/042734
§ 371 (c)(1),
(2), (4) Date: Dec. 11, 2013

(87) PCT Pub. No.: WO2012/174419
PCT Pub. Date: Dec. 20, 2012

(65) Prior Publication Data
US 2014/0127690 A1   May 8, 2014

Related U.S. Application Data

(60) Provisional application No. 61/498,497, filed on Jun. 17, 2011.

(51) Int. Cl.
*C12Q 1/68* (2018.01)
*C12Q 1/6883* (2018.01)
*C12Q 1/6886* (2018.01)

(52) U.S. Cl.
CPC ......... *C12Q 1/6883* (2013.01); *C12Q 1/6886* (2013.01); *C12Q 2600/118* (2013.01); *C12Q 2600/156* (2013.01)

(58) Field of Classification Search
None
See application file for complete search history.

(56) References Cited

FOREIGN PATENT DOCUMENTS

WO   WO 2010/087702 A1   8/2010

OTHER PUBLICATIONS

List et al; Journal of Clinical Oncology, vol. 26, 2008; 15S abstract.*
Rocquain et al; BMC Cancer, 2010, 10:401.*
Nagata et al; Blood, 2010, 116:21, abstract 4011.*
O'Connor et al; Leukemia, 1998, vol. 12, pp. 1099-1106.*
Bejar, R. et al., "Validation of a Prognostic Model and the Impact of Mutations in Patients With Lower-Risk Myelodysplastic Syndromes," Journal of Clinical Oncology, pp. 1-7 (2012).
Bejar, R., et al., "Clinical Effect of Point Mutations in Myelodysplastic Syndromes," The New England Journal of Medicine, 364: pp. 2496-2506 (2011).
Malcovati, L. et al., "Clinical significance of SF3B1 mutations in myelodysplastic syndromes and myelodysplastic/myeloproliferative neoplasms," Blood, 118(24): 6239-46 (2011).
Papaemmanuil, M. et al., "Somatic SF3B1 Mutation in Myelodysplasia with Ring Sideroblasts," The New England Journal of Medicine, 365: pp. 1384-1395 (2011).
Affymetrix: "Data Sheet Affymetrix (R) Genome-Wide Human SNP Array 6.0", Internet Citation, pp. 1-4. XP002525407 (2007) Retrieved from the Internet: [retrieved on Apr. 10, 2009] URL:http://www.affymetrix.comjsupportjtechnicaljdatasheetsjgenomewide_snp6_datasheet.pdf.
Bejar, R. et al., "Clinical Effect of Point Mutations in Myelodysplastic Syndromes", *New England Journal of Medicine*, 364(26):2496-2506 (2011).
Kita-Sasai, Y. et al., "International prognostic scoring system and TP53 mutations are independent prognostic indicators for patients with myelodysplastic syndrome", *British Journal of Haematology*, 115(2):309-312 (2001).
Padua, R.A. et al., "RAS, FMS and p53 mutations and poor clinical outcome in myelodysplasias: a 10-year follow-up", *Leukemia*, 12(6):887-892 (1998).
Paquette, R., "N-ras Mutations Are Associated With Poor Prognosis and Increased Risk of Leukemia in Myelodysplastic Syndrome", *Blood*, 82(2):590-599 (1993).
Langemeijer, S.M.C. et al., "Acquired mutations in TET2 are common in myelodysplastic syndromes", *Nature Genetics*, 41(7):838-842 (2009).
Thol, F. et al., "IDH1 mutations in patients with myelodysplastic syndromes are associated with an unfavorable prognosis", *Haematologica*, 95(10):1668-1674 (2010).
Yamagata, T.: "Low-Level Expression of ETV6/TEL in Patients with Myelodysplastic Syndrome", *International Journal of Hematology*, 86(3):282 (2007).
Australian Examination Report issued in Australian Patent Application No. 2012271386 dated Jun. 30, 2016.
Takaira, et al., "A Study of Karyotype in Myelodysplastic Syndrome with 5q-," Journal of Chromosome and Gene Analysis, May 2009, vol. 27, No. 1, pp. 35-41.
Mitani, et al., "Pathology of MDS Syndromes Associated with Gene Abnormalities," 2009, vol. 50, No. 10, pp. 1325-1331.
Notice of Reasons for Rejections, cited in corresponding Japanese Patent Application No. 2014-516047, dated Apr. 13, 2016 (6 pages).

* cited by examiner

*Primary Examiner* — Jehanne S Sitton
(74) *Attorney, Agent, or Firm* — Melissa Hunter-Ensor; Leslie Serunian; Greenberg Traurig, LLP

(57) ABSTRACT

Somatic non-silent mutations on selected biomarkers are reliable indicators for the overall survival of Myelodysplastic Syndrome subjects.

31 Claims, 50 Drawing Sheets

| Karyotype | -7/del(7q) (alone or +1) | del(20q) | del(5q) | +8 | Complex | Normal | Other | p-value |
|---|---|---|---|---|---|---|---|---|
| N | 10 | 18 | 22 | 24 | 57 | 255 | 46 | |
| At least 1 Mutation | 7 (70) | 11 (61) | 8 (36) | 13 (54) | 32 (56) | 133 (52) | 20 (43) | 0.44 |
| No Mutation | 3 (30) | 7 (39) | 14 (64) | 11 (46) | 25 (44) | 122 (48) | 26 (57) | |
| TET2+ | 1 (10) | 2 (11) | 3 (14) | 5 (21) | 3 (5) | 68 (27) | 7 (15) | 0.005 |
| TP53+ | 0 (0) | 0 (0) | 1 (5) | 0 (0) | 26 (46) | 5 (2) | 1 (2) | <0.001 |
| EZH2+ | 0 (0) | 2 (11) | 1 (5) | 2 (8) | 0 (0) | 20 (8) | 3 (7) | 0.23 |

|                      | N (%)     |           |           |          |         |
|----------------------|-----------|-----------|-----------|----------|---------|
| Age Group            | <55 yrs.  | 55-64 yrs | 65-74 yrs.| ≥75 yrs. | p-value |
| N                    | 49        | 88        | 179       | 123      |         |
| At least 1 Mutation  | 16 (33)   | 45 (51)   | 94 (53)   | 71 (58)  | 0.02    |
| No Mutation          | 33 (67)   | 43 (49)   | 85 (47)   | 52 (42)  |         |
| No Mut/Normal Karyo  | 17 (35)   | 28 (33)   | 48 (27)   | 29 (24)  | 0.07    |
| Other                | 31 (65)   | 58 (67)   | 128 (73)  | 93 (76)  |         |

FIG. 7C  *RUNX1*  ENST00000300305  NM_001754.4
FIG. 7D  *TP53*  ENST00000445888  NM_000546.4
FIG. 7E  *EZH2*  ENST00000320356  NM_004456.3
FIG. 7F  *ETV6*  ENST00000266427  NM_001987.4
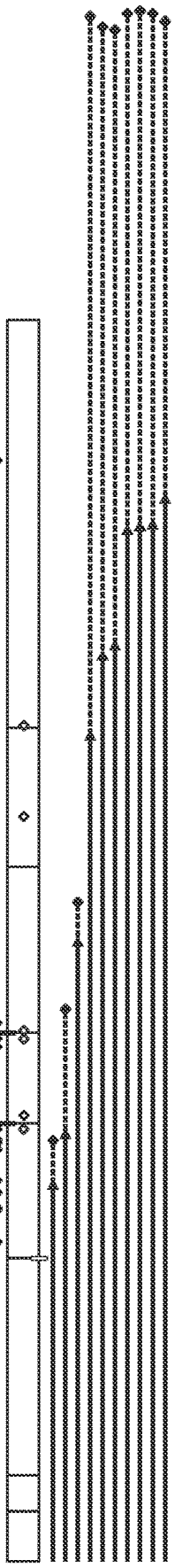
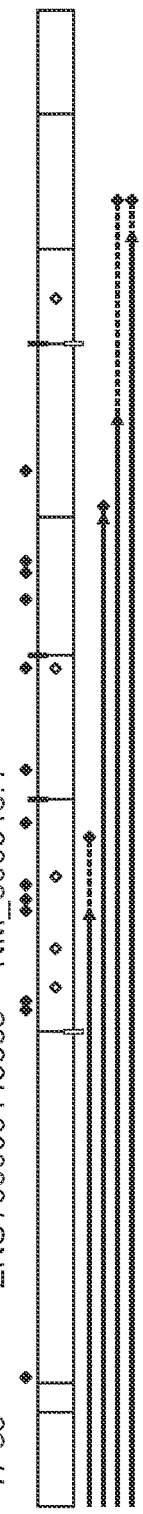
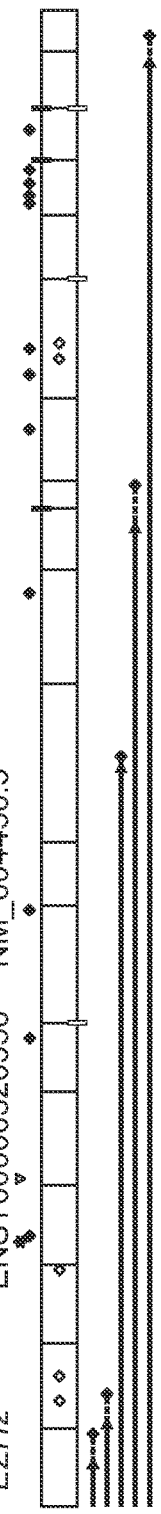

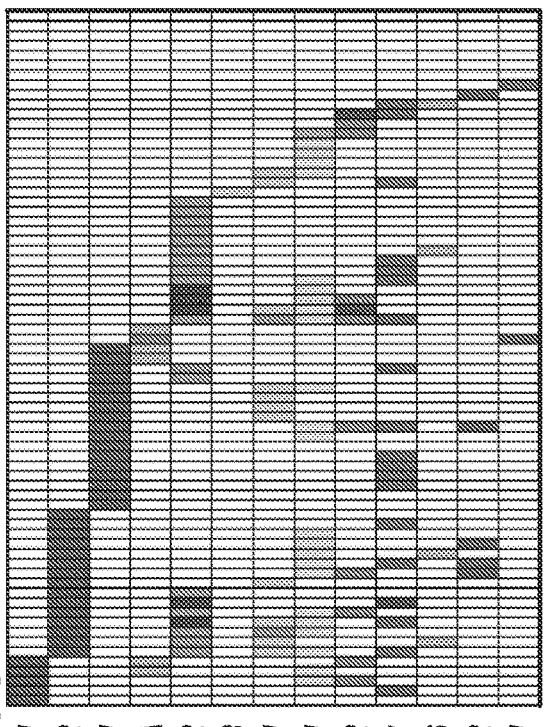
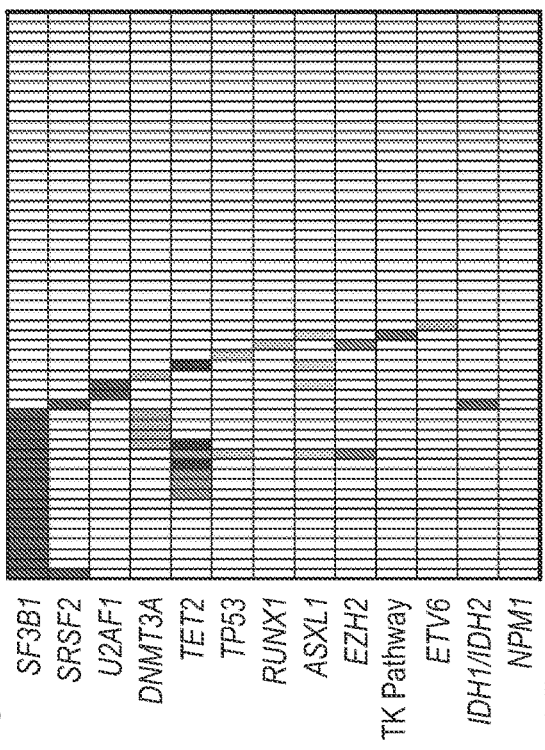
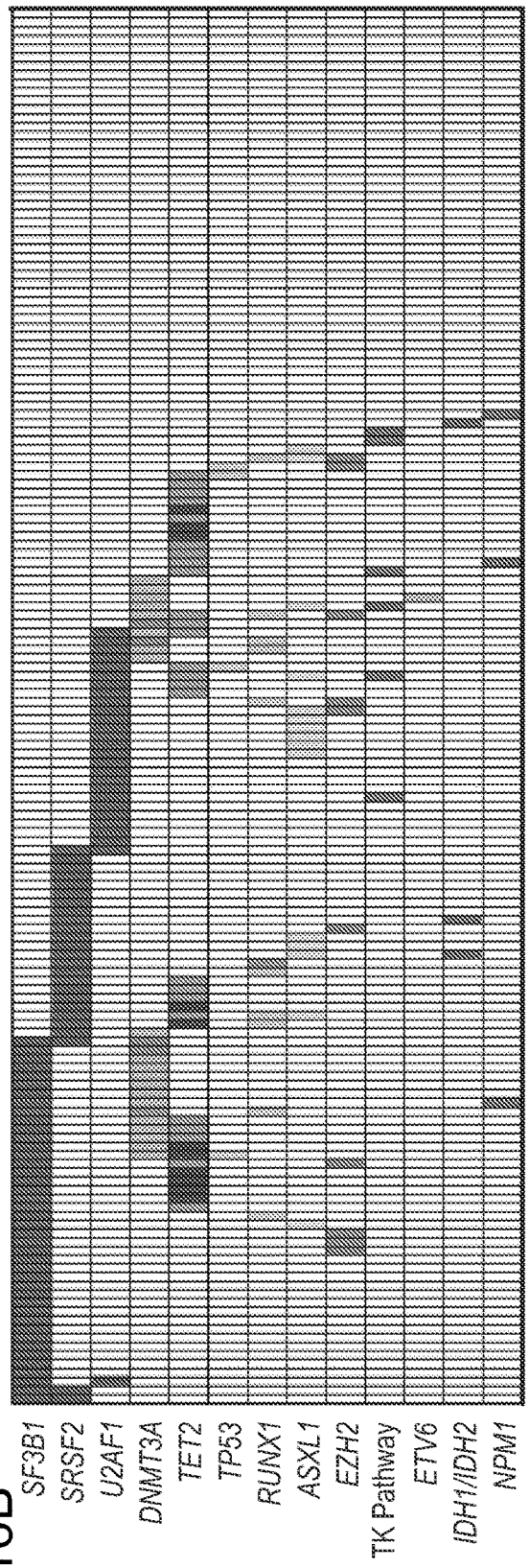
FIG. 16A
FIG. 16B
FIG. 16C

MUTATION SIGNATURES FOR PREDICTING THE SURVIVABILITY OF MYELODYSPLASTIC SYNDROME SUBJECTS

RELATED APPLICATIONS

This application is a national stage application, filed under 35 U.S.C. § 371, of International Application No. PCT/US2012/042734, filed on Jun. 15, 2012 which claims the benefit of U.S. provisional application No. 61/498,497, filed Jun. 17, 2011, the contents of which is incorporated herein by reference in its entirety.

GOVERNMENT INTEREST

This invention was made with government support under R01 DK087992 and R01 HL082945 and awarded by the National Institutes of Health and P01 CA108631 and 3K12 CA087723 awarded by the National Cancer Institute. The United States government has certain rights in the invention.

FIELD OF THE INVENTION

This invention relates to method of predicting the survivability of myelodysplastic syndrome subjects.

BACKGROUND OF THE INVENTION

Myelodysplastic syndromes (MDS) are a heterogeneous group of clonal hematologic disorders characterized by ineffective hematopoiesis and dysplasia. It is a hematological disorder in which genomic abnormalities accumulate in a hematopoietic stem cell leading to peripheral cytopenias of varying degrees of severity, as a consequence of multilineage differentiation impairment, and, in the early phases, bone marrow (BM) apoptosis. Morbidity and mortality in the disease results from cytopenias or transformation to acute myeloid leukemia, which may both lead to serious infectious diseases, anemia or hemorrhage caused by dysfunction and reduction of blood cells. There are associated cytogenetic abnormalities, including deletions of chromosomes 5, 7, amongst others.

The diagnosis of MDS currently requires a multidisciplinary approach involving hematologic, morphologic and cytogenetic analyses, and may be difficult to render, owing to the fact that at least 50% of patients present with one or fewer cytopenias and only about 50% of patients demonstrate cytogenetic abnormalities. The choice of therapies used to treat MDS heavily depends on disease severity and the risk of progression to more advanced disease. The ability to accurately predict prognosis is therefore an essential component of patient care. Currently used prognostic scoring systems consider karyotypic abnormalities and certain clinical features to stratify MDS patients into risk groups. Some karyotypic abnormalities, such as deletion of chromosome 5q, help establish prognosis and can be associated with a specific clinical phenotype.[1] However, more than 50% of MDS patients have a normal karyotype, and patients with identical chromosomal abnormalities remain clinically heterogeneous.[2,3] Single gene mutations are not currently employed in prognostic scoring systems, but are likely to be key drivers of clinical phenotypes and overall survival (OS).[4-6] Understanding the clinical impact of mutations in different genes could improve the prediction of prognosis for patients with MDS and inform selection of specific therapies.

SUMMARY OF THE INVENTION

The present invention relates in part to the discovery that mutations of certain biological markers (referred to herein as "SIGNATURES") are present in hematological disorders, such as MDS, which indicates a risk of having a lower overall survival and more aggressive progression of the disease.

Accordingly, the present invention provides a method with a predetermined level of predictability for assessing overall survival (increased or decreased) in a subject suffering from myelodysplastic syndromes (MDS). Risk of having a decreased overall survival in the subject is determined by detecting the presence of one or more mutations in any one or more genes selected from ETV6, EZH2, RUNX1, ASXL1, DNMT3A, SRSF2, U2AF1 and SF3B. The presence of one or more detected non-silent mutations in one gene indicates a decreased overall survival of the subject when compared to a subject without these mutations. The presence of one or more mutations in both TET2 and SF3B1 indicates an increased overall survival of the subject when compared to a subject without only a TET2 mutation. The presence of one or more mutations in both DNMT3 and SF3B1 indicates an increased overall survival of the subject when compared to a subject without only a DNMT3 mutation. When the subject has RARS type MDS and one or mutations in SF3B1 indicates an increased overall survival of the subject when compared to a subject without the mutation In another aspect, the invention provides a method of diagnosing MDS or a risk of having MDS in a subject. The presence of one or more mutations on two or more genes selected from Table 6; or one or more mutations on any one or more genes selected from ETV6, EZH2, RUNX1, ASXL1, DNMT3A, SRSF2, U2AF1 and SF3B indicates that the subject has MDS or a risk of developing MDS.

In a further aspect, the invention provides a method with a predetermined level of predictability for monitoring the effectiveness of treatment or selecting a treatment regimen for MDS by determining the mutant allele frequency in two or more genes selected from Table 6, or in any one or more genes selected from ETV6, EZH2, RUNX1, ASXL1, DNMT3A, SRSF2, U2AF1 and SF3B over a period of time. Samples can be obtained from the subject before, during or after treatment.

The present invention also provides a method with a predetermined level of predictability for assessing the progression of MDS in a subject by determining the mutant allele frequency in two or more genes selected from Table 6, or in any one or more genes selected from ETV6, EZH2, RUNX1, ASXL1, DNMT3A, SRSF2, U2AF1 and SF3B over a period of time.

By mutant allele frequency is meant the frequency of occurrence of a given mutant allele (e.g., a sequence containing a mutation) in given sample.

A SIGNATURE includes, for example genes listed in Table 6. One, two, three, four, five, ten or more SIGNATURES are detected. In some embodiments at least two SIGNATURES selected from genes listed in Table 6 are detected. Preferably, ETV6, EZH2, RUNX1, ASXL1, DNMT3A, SRSF2, U2AF1 and SF3B are detected. Optionally, the methods of the invention further include measuring at least one standard parameters associated with a hematological disorder, such as MDS. A standard parameter is for example IPSS score.

The mutation of SIGNATURE nucleic acids is detected any method known in the art, such as for example, Sanger sequencing, Next-Generation genomic sequencing and/or Mass spectrometry genotyping. The nucleic acid sample is isolated from bone marrow or blood of the subject.

The biological sample is any bodily tissue or fluid that contains DNA. Preferably, the sample is bone marrow. The subject is preferably a mammal The mammal can be, e.g., a human, non-human primate, mouse, rat, dog, cat, horse, or cow.

The subject has a hematological disorder, such as MDS. In some aspects the sample is taken for a subject that has previously been treated for MDS. Alternatively, the sample is taken from the subject prior to being treated for MDS.

In various embodiments the assessment/monitoring is achieved with a predetermined level of predictability. By predetermined level of predictability is meant that that the method provides an acceptable level of clinical or diagnostic accuracy. Clinical and diagnostic accuracy is determined by methods known in the art.

The present invention further provides a kit comprising a plurality of detection reagents that detect the corresponding genes selected from Table 6 or a kit comprising reagents for the detection of one or more genes selected from E ETV6, EZH2, RUNX1, ASXL1, DNMT3A, SRSF2, U2AF1 and SF3B and instructions for using the kit. The kit can further comprises reagents for detecting TP53.

The invention also provides an MDS expression profile containing a pattern of mutations of one or more selected from E ETV6, EZH2, RUNX1, ASXL1, DNMT3A, SRSF2, U2AF1 and SF3B. Also included is a machine readable media containing the MDS expression profiles according to the invention Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIGS. 7A-7F shows the location and type of mutations within gene products. These figures show where amino acid altering mutations begin in each of six gene products. The gene product is shown as blue rectangles joined at exon boundaries. The mutation types are indicated by symbols described in the legend shown in panel A. (A) Stop codon and frameshift mutations predicted to truncate the TET2 gene product occur throughout its length. Missense and splice site mutations are clustered in one of two highly conserved C-terminus domains associated with the catalytic activity of TET2. Nearly a quarter of patients had two or more distinct mutations in TET2 suggesting biallelic abnormalities. Mitotic recombination leading to copy-neutral loss of heterozygosity has been seen recurrently in TET2-mutated MDS samples. Together, these patterns of mutation are consistent with a loss of function of this gene. (B) Mutations of ASXL1 are almost exclusively stop codons and frameshifts predicted to prematurely truncate its protein product. The bulk of these mutations occur in the terminal exon and are therefore, unlikely to induce nonsense-mediated decay. Mutated ASXL1 genes may produce abnormal proteins that retain their N-terminal domains which could lead to a gain-of-function or dominant-negative activity. (C) The RUNX1 protein contains two functionally important regions, a more proximal RUNT DNA binding domain and a more distal protein interaction domain. In frame mutations of RUNX1 are clustered in the RUNT domain. Similar mutations have been shown to produce proteins with dominant negative activity. Frameshift, nonsense, and splice site mutations appear to spare the proximal portion of the gene, although beyond a loss of normal activity, the functional impact of these mutations is unclear. (D) As with RUNX1, mutations of TP53 mostly spared the proximal portion of the gene. Several patients had two distinct TP53 mutations or a single mutation and loss of chromosome 17p where the TP53 gene resides. Most of the missense mutations we identified occurred in the central DNA binding domain and have previously been associated with a loss of function. (E) Mutations of EZH2 spanned the length of the gene. Several missense mutations clustered in the C-terminal SET domain responsible for methyltransferase activity. This pattern is consistent with a loss of function as the selection driver for EZH2 mutations. (F) Most of the ETV6 mutations we identified occur in the sterile alpha motif domain responsible for dimerization with other ETV6 molecules or other ets proteins.

DETAILED DESCRIPTION OF THE INVENTION

Figure 1:
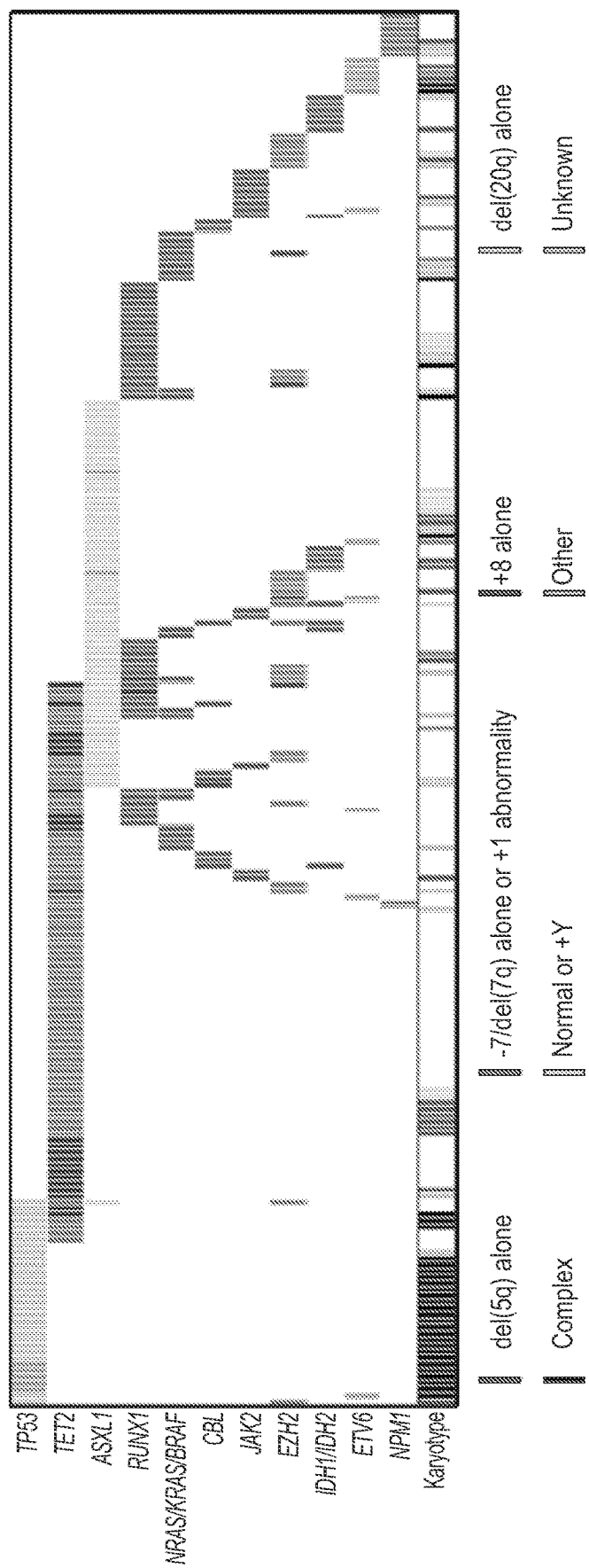
FIG. 1 shows the distribution of mutations and cytogenetic abnormalities. Mutations in the 11 most frequently mutated gene groups are shown by colored bars. Each column represents one of the 223 patient samples that had at least one mutation in one of the genes listed. Darker bars indicate samples with two or more distinct mutations in that gene group. The karyotype of each sample carrying a mutation is shown with a colored bar in the bottom row.

This invention is related to the identification of SIGNATURES that when somatically mutated associated with adverse prognosis for subjects with hematological disorders, such as myelodysplastic syndromes (MDS), acute myelogenous leukemia (AML), Acute lymphoblastic leukemia (ALL), Chronic lymphocytic leukemia (CLL), Chronic myelogenous leukemia (CML), or at risk of developing hematological disorders. These SIGNATURES are independent of existing clinical or molecular risk factors.

The prognostic significance of some mutations in MDS has previously been reported, but prior studies have generally examined small sample sets, and were limited to the analysis of one or a small number of genes, or focused exclusively on a particular subtype of MDS. To distinguish the independent contributions of mutations to clinical phenotype and OS, a large set of MDS patient samples for somatic mutations in a broad spectrum of cancer-associated genes were examined.

The invention provides methods for assessing a risk of a overall survival (e.g., increased or decreased) in a subject suffering from hematological disorders, such as myelodysplastic syndromes (MDS) by the detection of one or more mutations on any one or more Signature genes. These signatures genes are also useful for monitoring subjects undergoing treatments and therapies for MDS and for selecting or modifying therapies and treatments that would be efficacious in subjects having MDS, wherein selection and use of such treatments and therapies slow the progression of the tumor, or substantially delay or prevent its onset, or reduce or prevent the incidence of MDS.

Definitions

"SIGNATURES" in the context of the present invention encompasses, without limitation nucleic acids, together with their polymorphisms, mutations, variants, modifications, subunits, fragments, and other analytes or sample-derived measures. SIGNATURES can also include mutated nucleic acids.

Individual SIGNATURES are summarized in Table 6 and are collectively referred to herein as, inter alia, "MDS-associated genes", "MDS-associated nucleic acids", "SIGNATURE genes", or "SIGNATURE nucleic acids".

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

"FN" is false negative, which for a disease state test means classifying a disease subject incorrectly as non-disease or normal.

"FP" is false positive, which for a disease state test means classifying a normal subject incorrectly as having disease.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value." Non-limiting examples of "formulas" include sums, ratios, and regression operators, such as coefficients or exponents, biomarker value transformations and normalizations (including, without limitation, those normalization schemes based on clinical parameters, such as gender, age, or ethnicity), rules and guidelines, statistical classification models, and neural networks trained on historical populations. Of particular use is linear and non-linear equations and statistical classification analyses to determine the relationship between mutations of SIGNATURES nucleic acids detected in a subject sample and the subject's risk of having a lower overall survival or developing a hematological disorder, such as MDS. In panel and combination construction, of particular interest are structural and synactic statistical classification algorithms, and methods of risk index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, among others. Other techniques may be used in survival and time to event hazard analysis, including Cox, Weibull, Kaplan-Meier and Greenwood models well known to those of skill in the art. Many of these techniques are useful either combined with a SIGNATURE selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art.

A "health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome. The sum, across all predicted outcomes, of the product of the predicted population size for an outcome multiplied by the respective outcome's expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

For diagnostic (or prognostic) interventions of the invention, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (a.k.a., zero predicted subject outcome misclassifications or FP and FN), which all performance measures will favor over imperfection, but to differing degrees.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's non-analyte clinical parameters.

"Clinical parameters" or "risk factor" encompasses all non-sample or non-analyte biomarkers of subject health status or other characteristics, such as, without limitation, age (Age), ethnicity (RACE), gender (Sex), family history (FamHX), International Prognostic Scoring System (IPSS) score, karyotype, blast proportion or cytopenia.

"Negative predictive value" or "NPV" is calculated by TN/(TN+FN) or the true negative fraction of all negative test results. It also is inherently impacted by the prevalence of the disease and pre-test probability of the population intended to be tested.

See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test. Often, for binary disease state classification approaches using a continuous diagnostic test measurement, the sensitivity and specificity is summarized by Receiver Operating Characteristics (ROC) curves according to Pepe et al, "Limitations of the Odds Ratio in Gauging the Performance of a Diagnostic, Prognostic, or Screening Marker," Am. J. Epidemiol 2004, 159 (9): 882-890, and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), 4$^{th}$ edition 1996, W.B. Saunders Company, pages 192-199; and Zweig et al., "ROC Curve Analysis An Example Showing The Relationships Among Serum Lipid And Apolipoprotein Concentrations In Identifying Subjects With Coronary Artery Disease," Clin. Chem., 1992, 38(8): 1425-1428. An alternative approach using likelihood functions, odds ratios, information theory, predictive values, calibration (including goodness-of-fit), and reclassification measurements is summarized according to Cook, "Use and Misuse of the Receiver Operating Characteristic Curve in Risk Prediction," Circulation 2007, 115: 928-935.

Finally, hazard ratios and absolute and relative risk ratios within subject cohorts defined by a test are a further measurement of clinical accuracy and utility. Multiple methods are frequently used to defining abnormal or disease values, including reference limits, discrimination limits, and risk thresholds.

"Analytical accuracy" refers to the reproducibility and predictability of the measurement process itself, and may be summarized in such measurements as coefficients of variation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC, time to result, shelf life, etc. as relevant.

"Positive predictive value" or "PPV" is calculated by TP/(TP+FP) or the true positive fraction of all positive test results. It is inherently impacted by the prevalence of the disease and pre-test probability of the population intended to be tested.

"Sensitivity" is calculated by TP/(TP+FN) or the true positive fraction of disease subjects.

"Specificity" is calculated by TN/(TN+FP) or the true negative fraction of non-disease or normal subjects.

"Risk" in the context of the present invention, relates to the probability that an event will occur over a specific time period and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1−p) where p is the probability of event and (1−p) is the probability of no event) to no-conversion.

"Risk evaluation" or "evaluation of risk" in the context of the present invention encompasses making a prediction of the probability, odds, or likelihood that an event or disease state may occur. Risk evaluation can also comprise prediction of future clinical parameters, traditional laboratory risk factor values, or other indices of hematological disorders, such as MDS, either in absolute or relative terms in reference to a previously measured population. The methods of the present invention may be used to make continuous or categorical measurements of the risk of MDS thus diagnosing and defining the risk spectrum of a category of subjects defined as being at risk for hematological disorders.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

A "mutated gene" or "mutation" or "functional mutation" refers to an allelic form of a gene, which is capable of altering the phenotype of a subject having the mutated gene relative to a subject which does not have the mutated gene. The altered phenotype caused by a mutation can be corrected or compensated for by certain agents. If a subject must be homozygous for this mutation to have an altered phenotype, the mutation is said to be recessive. If one copy of the mutated gene is sufficient to alter the phenotype of the subject, the mutation is said to be dominant. If a subject has one copy of the mutated gene and has a phenotype that is intermediate between that of a homozygous and that of a heterozygous subject (for that gene), the mutation is said to be co-dominant. The term "mutation" means any base pair change in the nucleic acid sequence whether it changes the protein's structure or function or has no effect compared to wild type sequence. The term "germline mutation", as used herein, indicates a deleterious alteration in one gene allele which is present in every nucleous containing cell of the body. The term "somatic mutation" refers to a deleterious alteration in at least one gene allele that is not found in every cell of the body, but is found only in isolated cells. A characteristic of the somatic mutations as used herein is, that they are restricted to particular tissues or even parts of tissues or cells within a tissue and are not present in the whole organism harbouring the tissues or cells. Examples of somatic mutations include mutations produced by mismatch incorporations of nucleotides during replication of the genomic DNA in the course of the cell division cycle of proliferating cells. In some aspects of the present invention, mutations of genes listed in Table 6 are detected in nucleic acids isolated from bone marrow.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene.

A "sample" in the context of the present invention is a biological sample isolated from a subject and can include, by way of example and not limitation, bone marrow, tissue biopsies, whole blood, serum, plasma, blood cells, endothelial cells, circulating tumor cells, lymphatic fluid, ascites fluid, interstitial fluid (also known as "extracellular fluid" and encompasses the fluid found in spaces between cells, including, inter alia, gingival cevicular fluid), cerebrospinal fluid (CSF), saliva, mucous, sputum, sweat, urine, or any other secretion, excretion, or other bodily fluids.

A "subject" in the context of the present invention is preferably a mammal. The mammal can be a human, non-human primate, mouse, rat, dog, cat, horse, or cow, but are not limited to these examples. Mammals other than humans can be advantageously used as subjects that represent animal models of tumor metastasis. A subject can be male or female. A subject can be one who has been previously diagnosed or identified as having hematological disorders, such as MDS, and optionally has already undergone, or is undergoing, a therapeutic intervention for the disease. Alternatively, a subject can also be one who has not been previously diagnosed as having hematological disorders, such as MDS. For example, a subject can be one who exhibits one or more risk factors for hematological disorders, such as MDS.

"Overall survival (OS)" indicates the percentage of people in a study or treatment group who are alive for a given period of time after diagnosis, when the precise cause of death is not specified. The OS in this invention is measured from the time of sample collection to time of death from any cause; patients last known to be alive were censored at that time. OS curves were constructed using the method of Kaplan and Meier and compared using the log-rank test. All P values were based on 2-sided tests. OS is also evaluated for all patients using unadjusted and adjusted Cox proportional hazard regression modeling; models were adjusted for IPSS risk group at the time of sample collection.

The terms "nucleic acid," "polynucleotide," and "oligonucleotide" are used interchangeably and refer to a deoxyribonucleotide or ribonucleotide polymer in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties. In general, an analogue of a particular nucleotide has the same base-pairing specificity; i.e., an analogue of A will base-pair with T.

Methods and Uses of the Invention

The methods disclosed herein are used with subjects at risk for developing MDS, or other subjects with hematological disorders, such as those with Acute lymphoblastic leukemia (ALL), Acute myelogenous leukemia (AML), Chronic lymphocytic leukemia (CLL), or Chronic myelogenous leukemia (CML) or other types of hematological disorders and subjects undergoing treatment and/or therapies for MDS or other types of hematological disorders. The methods of the present invention can be used to assess a risk of a overall survival (OS) (i.e., increased or decreased) in a subject suffering from myelodysplastic syndromes (MDS). The methods of the present invention can also be used to monitor or select a treatment regimen for a subject who has MDS and other types of hematological disorders, and to screen subjects who have not been previously diagnosed as having MDS or other types of hematological disorders, such as subjects who exhibit risk factors for MDS. Preferably, the methods of the present invention are used to identify and/or diagnose subjects who are asymptomatic for MDS and other types of hematological disorders. "Asymptomatic" means not exhibiting the traditional signs and symptoms. More preferably, the present invention provides a method for assessing a risk of a decreased overall survival in a subject suffering from MDS who is predicted to have intermediate to high survival rate by other risk factors, such as IPSS score, karyotype, and/or age.

A risk of a decreased overall survival in a subject suffering from MDS or other types of hematological disorders can be determined by detecting in the nucleic acid sample from the subject the presence of one or more mutations on any one of the genes selected from ETV6, EZH2, RUNX1, ASXL1, DNMT3A, SRSF2, U2AF1 and SF3B1, wherein the presence of the mutation indicates a overall decreased survival of said subject when compared to a subject without said mutation.

The presence of one or more detected non-silent mutations in one gene indicates a decreased overall survival of the subject when compared to a subject without these mutations. The presence of one or more mutations in both TET2 and SF3B1 indicates an increased overall survival of the subject when compared to a subject without only a TET2 mutation. The presence of one or more mutations in both DNMT3 and SF3B1 indicates an increased overall survival of the subject when compared to a subject without only a DNMT3 mutation. When the subject has RARS type MDS and one or mutations in SF3B1 indicates an increased overall survival of the subject when compared to a subject without the mutation A subject having MDS and other types of hematological disorders can be identified by detecting the presence of one or more mutations on any two or more genes selected from Table 6 or one or more mutations on any one or more genes selected from ETV6, EZH2, RUNX1, ASXL1, DNMT3A, SRSF2, U2AF1 and SF3B1, wherein the presence of any one or more mutations indicate that the subject has MDS or a predisposition thereto.

The progression of MDS and other types of hematological disorders, or effectiveness of a treatment regimen can be monitored by determining the mutant allele frequency in two or more genes selected from Table 6 or the mutant allele frequency in any one or more genes selected from ETV6, EZH2, RUNX1, ASXL1, DNMT3A, SRSF2, U2AF1 and SF3B1 over time and comparing the mutant allele frequency of one or more genes comprising at least one mutation. For example, a first sample can be obtained prior to the subject receiving treatment and one or more subsequent samples are taken after or during treatment of the subject. MDS or other type of hematological disorders is considered to be progressive (or, alternatively, the treatment does not prevent progression) if the mutant allele frequency in mutant gene(s) increase over time, whereas MDS or other types of hematological disorders is not progressive if the mutant allele frequency in mutant gene(s) remains constant over time. For example, the methods of the invention can be used to discriminate the aggressiveness/and or accessing the stage of MDS. This will allow patients to be stratified into high or low risk groups and treated accordingly. For example, MDS patients with predicted lower overall survival could be treated with more aggressive therapies, such as treatment with Azacytidine (Vidaza®), Decitabine (Dacogen®), Lenalidomide (Revlimid), or bone marrow transplantation.

Additionally, treatments or therapeutic regimens for use in subjects having MDS or other types of hematological disorders, or subjects at risk for developing MDS or other types of hematological disorders can be selected based on the mutant allele frequency of the mutant gene(s) in samples obtained from the subjects. Two or more treatments or therapeutic regimens can be evaluated in parallel to determine which treatment or therapeutic regimen would be the most efficacious for use in a subject to delay onset, or slow progression of MDS or other types of hematological disorders.

By mutant allele frequency is meant the frequency of mutant allele present in the sample. Mutant allele frequency is determined by methods known in the art. For example copy number is determined by real time polymerase chain reaction, single nucleotide polymorphism (SNP) arrays, or interphase fluorescent in situ hybridization (FISH) analysis.

By "efficacious", it is meant that the treatment leads to a decrease in the mutant allele frequency in SIGNATURE genes. Assessment of the risk factors disclosed herein can be achieved using standard clinical protocols. Efficacy can be determined in association with any known method for diagnosing, identifying, or treating a hematological disorder.

Information regarding a treatment decision for a MDS patient can be achieved by obtaining information on one or more mutations on any one of SIGNATURE genes in a sample from the patient, and selecting a treatment regimen that prevents or reduces MDS in the patient if the mutant allele frequency in SIGNATURE genes is altered in a clinically significant manner.

The present invention also comprises a kit with a detection reagent that binds to one or more SIGNATURE nucleic acids. Also provided by the invention is an array of detection reagents, e.g., oligonucleotides that can bind to one or more SIGNATURE nucleic acids. The kit also includes one or more reagents for detecting the mutation on one or more SIGNATURE genes, for example primers for Mass spectrometry genotyping and one or more reagents for determining the mutant allele frequency in one or more mutated SIGNATURE genes in a sample from a subject.

Methods of evaluating the mutant allele frequency in a particular gene or chromosomal region are well known to those of skill in the art and include Hybridization-based Assays and Amplification-based Assays.

Hybridization-Based Assays

Hybridization-based assays include, but are not limited to, traditional "direct probe" methods such as Southern Blots or In Situ Hybridization (e.g., FISH), and "comparative probe" methods such as Comparative Genomic Hybridization (CGH). The methods can be used in a wide variety of formats including, but not limited to substrate—(e.g. membrane or glass) bound methods or array-based approaches as described below.

In situ hybridization assays are well known (e.g., Angerer (1987) Meth. Enzymol 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes are typically labeled, e.g., with radioisotopes or fluorescent reporters. The preferred size range is from about 200 bp to about 1000 bases, more preferably between about 400 to about 800 bp for double stranded, nick translated nucleic acids.

In some applications it is necessary to block the hybridization capacity of repetitive sequences. Thus, human genomic DNA or Cot-1 DNA is used to block nonspecific hybridization.

In Comparative Genomic Hybridization methods a first collection of (sample) nucleic acids (e.g. from a possible tumor) is labeled with a first label, while a second collection of (control) nucleic acids (e.g. from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number.

Other Hybridization protocols suitable for use with the methods of the invention are described, e.g., in Albertson (1984) EMBO J. 3: 1227-1234; Pinkel (1988) Proc. Natl. Acad. Sci. USA 85: 9138-9142; EPO Pub. No. 430,402; Methods in Molecular Biology, Vol. 33: In Situ Hybridization Protocols, Choo, ed., Humana Press, Totowa, N.J. (1994), etc.

The methods of this invention are particularly well suited to array-based hybridization formats. Arrays are a multiplicity of different "probe" or "target" nucleic acids (or other compounds) attached to one or more surfaces (e.g., solid, membrane, or gel). The multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) Genome Res. 7: 606-614; Jackson (1996) Nature Biotechnology 14:1685; Chee (1995) Science 274: 610; WO 96/17958.

Arrays, particularly nucleic acid arrays, can be produced according to a wide variety of methods well known to those of skill in the art. For example, in a simple embodiment, "low density" arrays can simply be produced by spotting (e.g. by hand using a pipette) different nucleic acids at different locations on a solid support (e.g. a glass surface, a membrane, etc.).

This simple spotting, approach has been automated to produce high density spotted arrays (see, e.g., U.S. Pat. No. 5,807,522). This patent describes the use of an automated system that taps a microcapillary against a surface to deposit a small volume of a biological sample. The process is repeated to generate high density arrays. Arrays can also be produced using oligonucleotide synthesis technology. Thus, for example, U.S. Pat. No. 5,143,854 and PCT patent publication Nos. WO 90/15070 and 92/10092 teach the use of light-directed combinatorial synthesis of high density oligonucleotide arrays.

A spotted array can include genomic DNA, e.g. overlapping clones that provide a high resolution scan of the amplicon corresponding to the region of interest. Amplicon nucleic acid can be obtained from, e.g., MACs, YACs, BACs, PACs, Pls, cosmids, plasmids, inter-Alu PCR products of genomic clones, restriction digests of genomic clone, cDNA clones, amplification (e.g., PCR) products, and the like.

The array nucleic acids are derived from previously mapped libraries of clones spanning or including the target sequences of the invention, as well as clones from other areas of the genome, as described below. The arrays can be hybridized with a single population of sample nucleic acid or can be used with two differentially labeled collections (as with an test sample and a reference sample).

Many methods for immobilizing nucleic acids on a variety of solid surfaces are known in the art. A wide variety of organic and inorganic polymers, as well as other materials, both natural and synthetic, can be employed as the material for the solid surface. Illustrative solid surfaces include, e.g., nitrocellulose, nylon, glass, quartz, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition, substances that form gels can be used. Such materials include, e.g., proteins (e.g., gelatins), lipopolysaccharides, silicates, agarose and polyacrylamides. Where the solid surface is porous, various pore sizes may be employed depending upon the nature of the system.

Detection of a hybridization complex may require the binding of a signal generating complex to a duplex of target and probe polynucleotides or nucleic acids. Typically, such binding occurs through ligand and anti-ligand interactions, such as between a ligand-conjugated probe and an anti-ligand conjugated with a signal.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

Methods of optimizing hybridization conditions are well known to those of skill in the art (see, e.g., Tijssen (1993) Laboratory Techniques in Biochemistry and Molecular Biology, Vol. 24: Hybridization With Nucleic Acid Probes, Elsevier, N.Y.).

Amplification-Based Assays

In another embodiment, amplification-based assays can be used to measure mutant allele frequency. In such amplification-based assays, the nucleic acid sequences act as a template in an amplification reaction (e.g. Polymerase Chain Reaction (PCR). In a quantitative amplification, the amount of amplification product will be proportional to the amount of template in the original sample. Comparison to appropriate (e.g. healthy tissue) controls provides a measure of the mutant allele frequency of the desired target nucleic acid sequence. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) PCR Protocols, A Guide to Methods and Applications, Academic Press, Inc. N.Y.).

Other suitable amplification methods include, but are not limited to ligase chain reaction (LCR) (see Wu and Wallace (1989) Genomics 4: 560, Landegren et al. (1988) Science 241: 1077, and Barringer et al. (1990) Gene 89: 117); transcription amplification (Kwoh et al. (1989) Proc. Natl. Acad. Sci. USA 86: 1173); and self-sustained sequence replication (Guatelli et al. (1990) Proc. Nat. Acad. Sci. USA 87: 1874).

Methods of detecting somatic mutations of a particular gene or chromosomal region are well known to those of skill in the art and include Mass spectrometry genotyping and Next-generation pyrosequencing. A variety of methods are available for detecting the presence of mutations in an individual gene or chromosome. Advancements in this field have provided accurate, easy, and inexpensive large-scale genotyping. Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR. Several of the methods known in the art for detecting specific single nucleotide polymorphisms are summarized below. The method of the present invention is understood to include all available methods.

For mutations that produce premature termination of protein translation, the protein truncation test (PTT) offers an efficient diagnostic approach (Roest, et. al., (1993) *Hum. Mol. Genet.* 2:1719-21; van der Luijt, et. al., (1994) *Genomics* 20:1-4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize 5' and 3' to at least one allele of one SIGNATURE gene listed in Table 6 under conditions such that hybridization and amplification of the allele occurs, and (iv) detecting the amplification product. These detection schemes are especially useful for the detection of nucleic acid molecules if such molecules are present in very low numbers.

In some aspects of the present invention, any of a variety of sequencing reactions known in the art can be used to directly sequence the allele. Exemplary sequencing reactions include those based on techniques developed by Maxim and Gilbert ((1977) Proc. Natl Acad Sci USA 74:560) or Sanger (Sanger et al (1977) Proc. Nat. Acad. Sci USA 74:5463). It is also contemplated that any of a variety of automated sequencing procedures may be utilized when performing the subject assays (see, for example Biotechniques (1995) 19:448), including sequencing by mass spectrometry (see, for example PCT publication WO 94/16101; Cohen et al. (1996) Adv Chromatogr 36:127-162; and Griffin et al. (1993) Appl Biochem Biotechnol 38:147-159). It will be evident to one of skill in the art that, for certain embodiments, the occurrence of only one, two or three of the nucleic acid bases need be determined in the sequencing reaction. For instance, A-track or the like, e.g., where only one nucleic acid is detected, can be carried out.

Diagnostic and Prognostic Indications of the Invention

The invention allows the prognosis and diagnosis of a hematological disorder such as MDS, among other types. The risk of having a lower overall survival in a subject suffering from a disease such as MDS can be determined by detecting one or more mutations on any one or more genes selected from ETV6, EZH2, RUNX1, ASXL1, DNMT3A, SRSF2, U2AF1 and SF3B1, in a test sample. Subjects identified as having a risk of a decreased overall survival can optionally be selected to receive more aggressive treatment regimens, such as administration of Azacytidine (Vidaza®), Decitabine (Dacogen®), Lenalidomide (Revlimid), or having bone marrow transplantation to delay, reduce or prevent subject's progression of the disease.

The present invention may be used to diagnose a subject by detecting one or more mutations on two or more genes selected from Table 6; or one or more mutations on any one or more genes selected from ETV6, EZH2, RUNX1, ASXL1, DNMT3A, SRSF2, U2AF1 and SF3B1.

The mutation of the SIGNATURE genes can be detected by Next-Generation sequencing or Mass spectrometry genotyping. The presence of one or more non-silent mutations on any one or more genes selected from ETV6, EZH2, RUNX1, ASXL1, DNMT3A, SRSF2, U2AF1 and SF3B1 indicates the risk of a decreased overall survival in the subject suffering from a hematological disorder, such as MDS.

The mutant allele frequency in the mutated SIGNATURE genes allows for the course of treatment of a hematological disorder, such as MDS to be monitored. This method, a biological sample can be provided from a subject undergoing treatment regimens, e.g. drug treatment for MDS. If desired, biological samples are obtained from the subject at various time points before, during, or after treatment.

The mutant allele frequency in the mutated SIGNATURE genes can be determined by any method known in the art, for example, real time polymerase chain reaction, single nucleotide polymorphism (SNP) arrays, or interphase fluorescent in situ hybridization (FISH) analysis.

The present invention can also be used to screen patient or subject populations in any number of settings. For example, a health maintenance organization, public health entity or school health program can screen a group of subjects to identify those requiring interventions, as described above, or for the collection of epidemiological data. Insurance companies (e.g., health, life or disability) may screen applicants in the process of determining coverage or pricing, or existing clients for possible intervention. Data collected in such population screens, particularly when tied to any clinical progression to conditions like cancer or metastatic events, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. Patent Application No. 2002/0038227; U.S. Patent Application No. US 2004/0122296; U.S. Patent Application No. US 2004/0122297; and U.S. Pat. No. 5,018,067. Such systems can access the data directly from internal data storage or remotely from one or more data storage sites as further detailed herein.

A machine-readable storage medium can comprise a data storage material encoded with machine readable data or data arrays which, when using a machine programmed with instructions for using said data, is capable of use for a variety of purposes, such as, without limitation, subject information relating to a hematological disorder, such as MDS risk factors over time or in response drug therapies. Mutations of SIGNATURE genes and the mutant allele frequency in SIGNATURE genes with at least one mutation of the invention and/or the resulting evaluation of risk from those biomarkers can implemented in computer programs executing on programmable computers, comprising, inter alia, a processor, a data storage system (including volatile and non-volatile memory and/or storage elements), at least one input device, and at least one output device. Program code can be applied to input data to perform the functions described above and generate output information. The output information can be applied to one or more output devices, according to methods known in the art. The computer may be, for example, a personal computer, microcomputer, or workstation of conventional design.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein. The health-related data management system of the invention may also be considered to be implemented as a computer-readable storage medium, configured with a computer program, where the storage medium so configured causes a computer to operate in a specific and predefined manner to perform various functions described herein.

Differences in the genetic makeup of subjects can result in differences in their relative abilities to metabolize various drugs, which may modulate the symptoms or risk factors of hematological disorder, such as MDS. Subjects that have MDS, or at risk for developing MDS can vary in age, ethnicity, and other parameters. Accordingly, use of the SIGNATURES disclosed herein, both alone and together in combination with known genetic factors for drug metabolism, allow for a pre-determined level of predictability that a putative therapeutic or prophylactic to be tested in a selected subject will be suitable for treating or preventing cancer or a metastatic event in the subject.

The aforementioned methods of the invention can be used to evaluate or monitor the progression and/or improvement of subjects who have been diagnosed with a hematological disorder, such as MDS, and who have undergone drug treatment.

Performance and Accuracy Measures of the Invention

The performance and thus absolute and relative clinical usefulness of the invention may be assessed in multiple ways as noted above. Amongst the various assessments of performance, the invention is intended to provide accuracy in clinical diagnosis and prognosis. The accuracy of a diagnostic or prognostic test, assay, or method concerns the ability of the test, assay, or method to distinguish between subjects having MDS or at risk for a lower overall survival, is based on whether the subjects have a non-silent mutation on one or more SIGNATURE genes listed in Table 6. In some embodiment, one or more mutations on only one SIGNATURE gene can provide a statistically significant assessment of the risk. As noted below, and without any limitation of the invention, achieving statistical significance, and thus the preferred analytical, diagnostic, and clinical accuracy, does not always require combinations of several SIGNATURES be used together. Mathematical algorithms are not always required in order to achieve a statistically significant index.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points. Use of statistics such as AUC, encompassing all potential cut point values, is preferred for most categorical risk measures using the invention, while for continuous risk measures, statistics of goodness-of-fit and calibration to observed results or other gold standards, are preferred.

By predetermined level of predictability it is meant that the method provides an acceptable level of clinical or diagnostic accuracy. Using such statistics, an "acceptable degree of diagnostic accuracy", is herein defined as a test or assay (such as the test of the invention for determining the clinically significant presence of mutations of SIGNATURE genes, which thereby indicates the presence of MDS and/or a risk of having a lower survival rate) in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.75, 0.80, desirably at least 0.85, more desirably at least 0.875, preferably at least 0.90, more preferably at least 0.925, and most preferably at least 0.95.

Alternatively, the methods predict the presence or absence of a hematological disorder, such as MDS, or response to therapy with at least 75% accuracy, more preferably 80%, 85%, 90%, 95%, 97%, 98%, 99% or greater accuracy.

The predictive value of any test depends on the sensitivity and specificity of the test, and on the prevalence of the condition in the population being tested. This notion, based on Bayes' theorem, provides that the greater the likelihood that the condition being screened for is present in an individual or in the population (pre-test probability), the greater the validity of a positive test and the greater the likelihood that the result is a true positive. Thus, the problem with using a test in any population where there is a low likelihood of the condition being present is that a positive result has limited value (i.e., more likely to be a false positive). Similarly, in populations at very high risk, a negative test result is more likely to be a false negative.

As a result, ROC and AUC can be misleading as to the clinical utility of a test in low disease prevalence tested populations (defined as those with less than 1% rate of occurrences (incidence) per annum, or less than 10% cumulative prevalence over a specified time horizon). Alternatively, absolute risk and relative risk ratios as defined elsewhere in this disclosure can be employed to determine the degree of clinical utility. Populations of subjects to be tested can also be categorized into quartiles by the test's measurement values, where the top quartile (25% of the population) comprises the group of subjects with the highest relative risk for developing a hematological disorder, and the bottom quartile comprising the group of subjects having the lowest relative risk for developing a hematological disorder. Generally, values derived from tests or assays having over 2.5 times the relative risk from top to bottom quartile in a low prevalence population are considered to have a "high degree of diagnostic accuracy," and those with five to seven times the relative risk for each quartile are considered to have a "very high degree of diagnostic accuracy." Nonetheless, values derived from tests or assays having only 1.2 to 2.5 times the relative risk for each quartile remain clinically useful are widely used as risk factors for a disease; such is the case with total cholesterol and for many inflammatory biomarkers with respect to their prediction of future metastatic events. Often such lower diagnostic accuracy tests must be combined with additional parameters in order to derive meaningful clinical thresholds for therapeutic intervention, as is done with the aforementioned global risk assessment indices.

A health economic utility function is an yet another means of measuring the performance and clinical value of a given test, consisting of weighting the potential categorical test outcomes based on actual measures of clinical and economic value for each. Health economic performance is closely related to accuracy, as a health economic utility function specifically assigns an economic value for the benefits of correct classification and the costs of misclassification of tested subjects. As a performance measure, it is not unusual to require a test to achieve a level of performance which results in an increase in health economic value per test (prior to testing costs) in excess of the target price of the test.

In general, alternative methods of determining diagnostic accuracy are commonly used for continuous measures, when a disease category or risk category (such as those attic risk for having a metastatic event) has not yet been clearly defined by the relevant medical societies and practice of medicine, where thresholds for therapeutic use are not yet established, or where there is no existing gold standard for diagnosis of the pre-disease. For continuous measures of risk, measures of diagnostic accuracy for a calculated index are typically based on curve fit and calibration between the predicted continuous value and the actual observed values (or a historical index calculated value) and utilize measures such as R squared, Hosmer-Lemeshow P-value statistics and confidence intervals. It is not unusual for predicted values using such algorithms to be reported including a confidence interval (usually 90% or 95% CI) based on a historical observed cohort's predictions, as in the test for risk of future breast cancer recurrence commercialized by Genomic Health, Inc. (Redwood City, Calif.).

In general, by defining the degree of diagnostic accuracy, i.e., cut points on a ROC curve, defining an acceptable AUC value, and determining the acceptable ranges in relative mutant allele frequency s in SIGNATURES genes with at least one mutation of the invention allows for one of skill in the art to use mutations on SIGNATURE genes to identify, diagnose, or prognose subjects with a pre-determined level of predictability and performance.

One skilled in the art will note that the above listed SIGNATURES come from a diverse set of physiological and biological pathways, including many which are not commonly accepted to be related to hematological disorders. These groupings of different SIGNATURES, even within those high significance segments, may presage differing signals of the stage or rate of the progression of the disease. Such distinct groupings of SIGNATURES may allow a more biologically detailed and clinically useful signal from the SIGNATURES as well as opportunities for pattern recognition within the SIGNATURES algorithms combining the multiple SIGNATURES signals.

One or more, two or more of the listed SIGNATURES can be detected in the practice of the present invention. For example, two (2), three (3), four (4), five (5), ten (10), fifteen (15), or more SIGNATURES can be detected.

In some aspects, all 20 SIGNATURES listed herein can be detected. Preferred ranges from which the number of SIGNATURES can be detected include ranges bounded by any minimum selected from between one and 20, particularly two, four, five, ten, twenty, fifty or more.

Kits

The invention also includes reagents for detecting mutations of SIGNATURE genes and reagents for determining the mutant allele frequency in SIGNATURE genes with at least one non-silent mutation, such as, nucleic acids that specifically identify one or more SIGNATURE nucleic acids by having homologous nucleic acid sequences, such as oligonucleotide sequences, complementary to a portion of the SIGNATURE nucleic acids packaged together in the form of a kit. The oligonucleotides can be fragments of the SIGNATURE genes. For example the oligonucleotides can be 200, 150, 100, 50, 25, 10 or less nucleotides in length. The kit may contain in separate container or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit. The assay may for example be in the form of a Northern hybridization or a sandwich ELISA as known in the art. Alternatively, the kit contains a nucleic acid substrate array comprising one or more nucleic acid sequences.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents, patent applications, and other references cited herein are hereby incorporated by reference. Genbank and NCBI submissions indicated by accession number cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

EXAMPLES

Example 1: General Methods

Patient Samples

Whole bone marrow aspirate and buccal swab samples from MDS patients were obtained from Rush University Medical Center, the University of Massachusetts Medical Center, and the MD Anderson Cancer Center. Samples were acquired from consenting patients between 1994 and 2008 under protocols approved by the Institutional Review Board at each institution. DNA was isolated and whole genome amplified (Qiagen, Valencia, Calif.). Amplified DNA was used for mutation discovery. Patient demographics are detailed in Table 1 below. The IPSS risk group was recalculated at the time a sample was collected. Survival analysis confirmed the prognostic validity of this recalculation in our sample set (Table 2). The median follow-up was 4.44 years (95% CI 4.12, 6.19) during which time 332 patients died and 107 were censored at the last known date alive.

TABLE 1

Patient Characteristics and Association with Median Survival

| | N (%) | Median Survival years (95% CI) | p-value† |
|---|---|---|---|
| Age | | | |
| <55 yrs. | 49 (11) | 3.14 (2.54, 7.44) | 0.003 |
| 55-64 yrs. | 88 (20) | 2.02 (1.29, 2.72) | |
| 65-74 yrs. | 179 (41) | 1.83 (1.47, 2.14) | |
| ≥75 yrs. | 123 (28) | 1.44 (1.05, 1.86) | |
| Sex | | | |
| Female | 133 (30) | 2.14 (1.71, 2.83) | 0.10 |
| Male | 306 (70) | 1.72 (1.40, 2.03) | |
| FAB | | | |
| RA | 197 (45) | 2.62 (2.13, 3.12) | <0.001 |
| RARS | 47 (11) | 4.16 (1.60, 5.19) | |
| RAEB-I | 105 (24) | 1.40 (1.07, 1.86) | |
| RAEB-II | 55 (13) | 0.95 (0.76, 1.22) | |
| RAEB-t | 34 (8) | 1.11 (0.61, 1.47) | |
| Unknown | 1 (<1) | NA | |
| IPSS | | | |
| Low | 110 (25) | 4.23 (3.14, 5.55) | <0.001 |
| Int1 | 185 (42) | 1.86 (1.61, 2.24) | |
| Int2 | 101 (23) | 0.95 (0.73, 1.22) | |
| High | 32 (7) | 0.79 (0.48, 1.11) | |
| Unknown | 11 (3) | NA | |
| Karyotype | | | |
| Good | 310 (71) | 2.18 (1.86, 2.59) | <0.001 |
| Intermediate | 55 (13) | 1.37 (0.84, 1.86) | |
| Poor | 67 (15) | 0.87 (0.58, 1.27) | |
| Unknown | 7 (1) | NA | |
| Karyotype | | | |
| −7/del(7q) isolated or +1 | 10 (2) | 0.73 (0.07, 1.05) | <0.001 |
| del(20q) isolated | 18 (4) | 1.32 (0.88, 1.98) | |
| del(5q) isolated | 22 (5) | 1.67 (1.02, 4.16) | |
| +8 isolated | 24 (5) | 1.40 (0.79, 2.14) | |
| Complex | 57 (13) | 1.10 (0.58, 1.70) | |
| Normal | 255 (58) | 2.40 (2.11, 2.72) | |
| Other | 46 (10) | 1.31 (0.78, 2.11) | |
| Unknown | 7 (1) | NA | |
| Blast % | | | |
| <5% | 247 (56) | 2.65 (2.24, 3.14) | <0.001 |
| 5-10% | 112 (26) | 1.34 (0.96, 1.71) | |
| 11-20% | 61 (14) | 1.06 (0.77, 1.26) | |
| 21-30% | 18 (4) | 1.15 (0.61, 1.48) | |
| Unknown | 1 (<1) | NA | |
| Hemoglobin (g/dl) | | | |
| <8.0 | 46 (10) | 1.22 (0.70, 1.98) | 0.002 |
| 8.0-9.99 | 175 (40) | 1.51 (1.11, 1.88) | |
| 10.0-11.99 | 145 (33) | 2.14 (1.70, 2.59) | |
| ≥12.0 | 64 (15) | 3.05 (2.03, 6.28) | |
| Unknown | 9 (2) | NA | |
| Absolute Neutrophil Count (cells/μL) | | | |
| <500 | 58 (13) | 1.47 (0.88, 1.93) | 0.001 |
| 500-1,499 | 145 (33) | 1.59 (1.11, 2.14) | |
| 1,500-9,999 | 203 (46) | 2.54 (2.02, 2.89) | |
| ≥10,000 | 8 (2) | 0.91 (0.14, 3.33) | |
| Unknown | 25 (6) | NA | |
| Platelets (per μL) | | | |
| <50,000 | 123 (28) | 1.07 (0.79, 1.36) | <0.001 |
| 50,000-149,000 | 168 (38) | 1.82 (1.40, 2.14) | |
| 150,000-449,999 | 119 (27) | 3.18 (2.54, 4.89) | |
| ≥450,000 | 20 (5) | 3.73 (1.46, 8.65) | |
| Unknown | 9 (2) | NA | |

A total of 31 patients were reported to have therapy-related MDS. Since the IPSS has not been validated in this subgroup, and it is difficult to be certain which patients with an exposure history truly have therapy-related MDS, we assigned an IPSS risk group to all patients. Only 10 patients in our sample set underwent stem-cell transplantation. Details of other potential treatments are not known for all patients. However, a large proportion of patients died before the FDA approval of therapies proven to extend overall survival of patients with MDS. Of the 332 patients that are known to have died during the follow up period, 167 (50.3%) died prior to the date of azacitidine approval (May 19, 2004), 201 (63.3%) died prior to the date of decitabine approval (May 2, 2006), and 193 (58.1%) died prior to the date of lenalidomide approval (Dec. 27, 2005). Therefore, many of patients examined in this study are unlikely to have received potentially life prolonging treatment.

TABLE 2

Determination of International Prognostic Scoring System (IPSS) Risk Groups. Each of three prognostic variables is assigned a score as outlined in the table below. The sum of these scores is used to determine the IPSS risk group.

International Prognostic Scoring System

| | Score Value | | | | |
|---|---|---|---|---|---|
| Prognostic Variable | 0 | 0.5 | 1.0 | 1.5 | 2.0 |
| Bone Marrow Blast Percentage (%) | <5 | 5-10 | | 11-20 | 21-30 |
| Karyotype Category* | Good | Intermediate | Poor | | |
| Number of Cytopenias | 0 or 1 | 2 or 3 | | | |

*Karyotype Categories
Good: normal, −Y, del(5q), del(20q)
Intermediate: other (not good or poor)
Poor: chromosome 7 anomalies or complex (≥3 abnormalities)

| IPSS Risk Groups | Total Score |
|---|---|
| Low | 0 |
| Intermediate-1 | 0.5-1.0 |
| Intermediate-2 | 1.5-2.0 |
| High | ≥2.5 |

Mass Spectrometry Genotyping

Genotyping of 953 mutations representing 111 genes was performed with iPlex (Sequenom, San Diego, Calif.) extension chemistry and mass spectrometer detection on amplified DNA as previously described using the complete set of OncoMap assays.[19,20] This technique was chosen for its ability to identify in high-throughput, those recurrent oncogene mutations limited to well-characterized locations. All candidate mutations identified by mass spectrometric genotyping were validated with redesigned assays in unamplified or independently amplified DNA from the same individual using homogenous Mass-Extend (hME) chemistry as described previously.[21] This technique can reliably detect mutations present at a frequency of 10% or greater.

DNA Sequencing

Next-generation pyrosequencing of PCR-amplified exons of TET2, RUNX1, TP53, CDKN2A, PTEN, NPM1-Exon 11, and CBL-Exons 8 and 9 was performed using the sequencing platform from 454 Life Sciences (Branford, Conn.). Known single nucleotide polymorphisms (SNPs), intronic polymorphisms more than 6 bases from a splice junction, and silent mutations were excluded from further analysis. ASXL1, EZH2, KDM6A, IDH1 exon 4, IDH2 exon 4, and ETV6 were analyzed by Sanger sequencing.

Figures 4A, 4B:
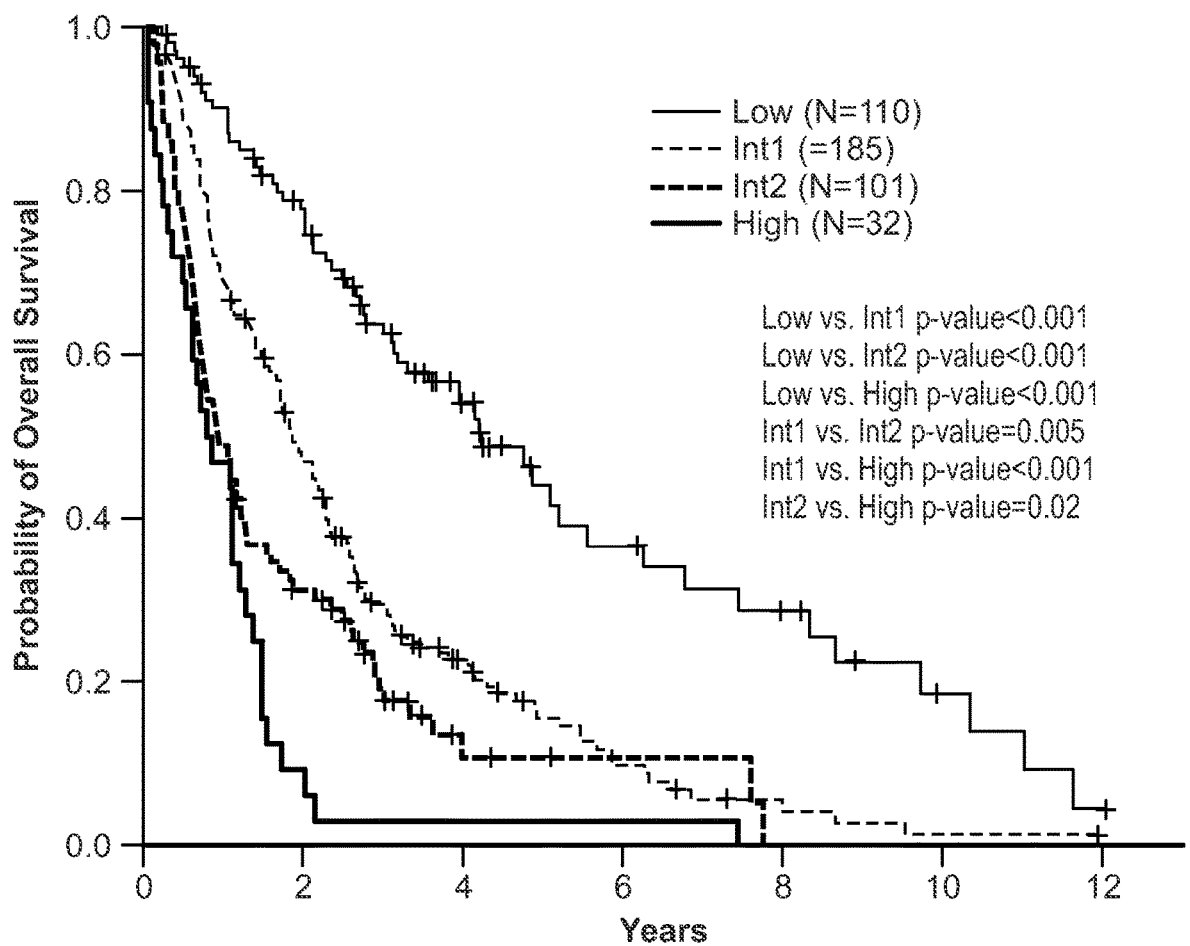
FIG. 4 shows the IPSS classification and association with overall survival. IPSS risk group was determined at the time of sample collection and compared to the original IPSS classification for each patient. Panel A: 73 patients had their IPSS risk group change upon reclassification. Only 2 patients moved more than one category (1 from Int2 to Low and 1 from Low to Int2). Panel B is a Kaplan-Meier survival plot comparing the overall survival of patients based on their reclassified IPSS. Pairwise comparisons confirm that survival of each group is significantly different from every other group.
Figures 5A, 5B:
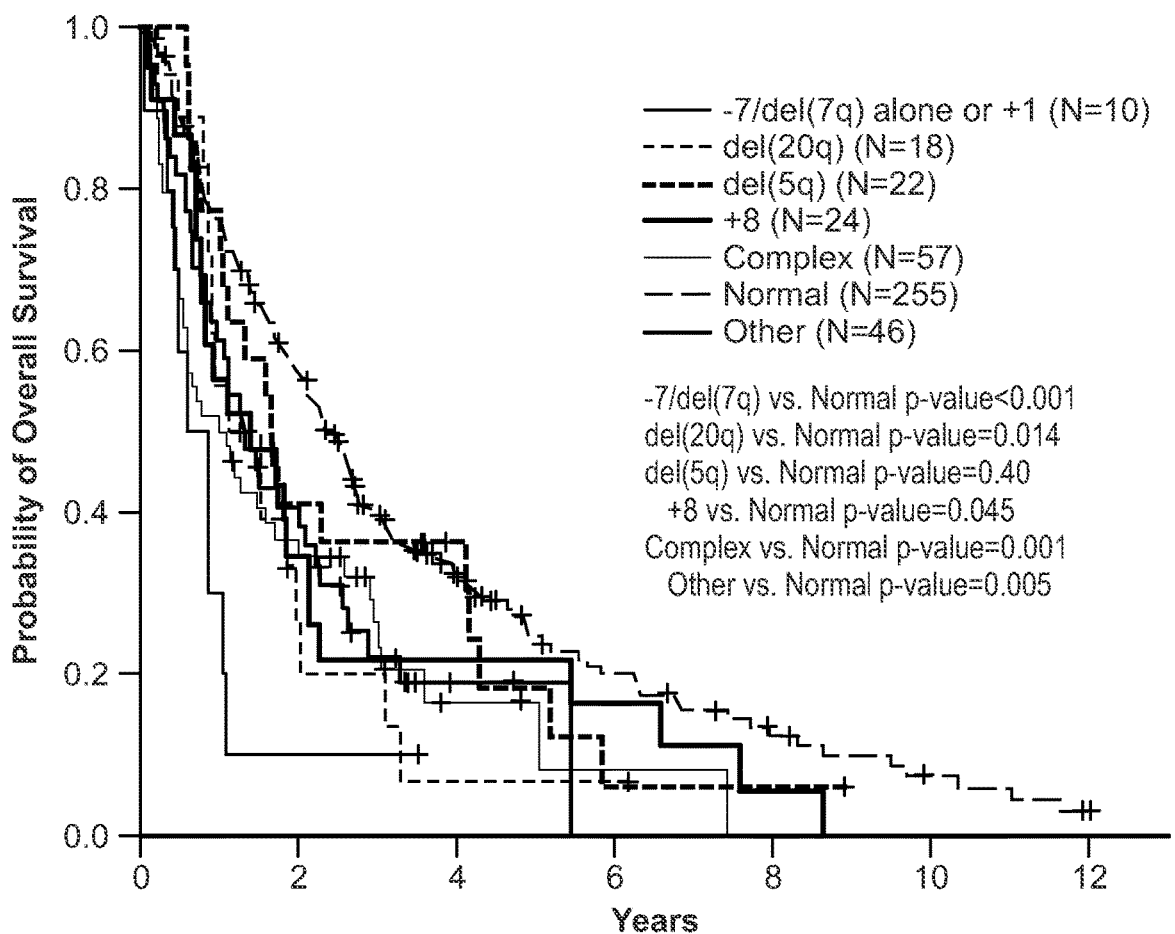
FIG. 5 shows the association of karyotype with mutations and overall survival. Panel A shows the distribution and frequency of karyotype abnormalities by mutation status. Panels B and C are Kaplan-Meier survival curves illustrating the overall survival of patients based on karyotype and karyotype group as defined in the IPSS at the time of sample collection.
Figure 5C:
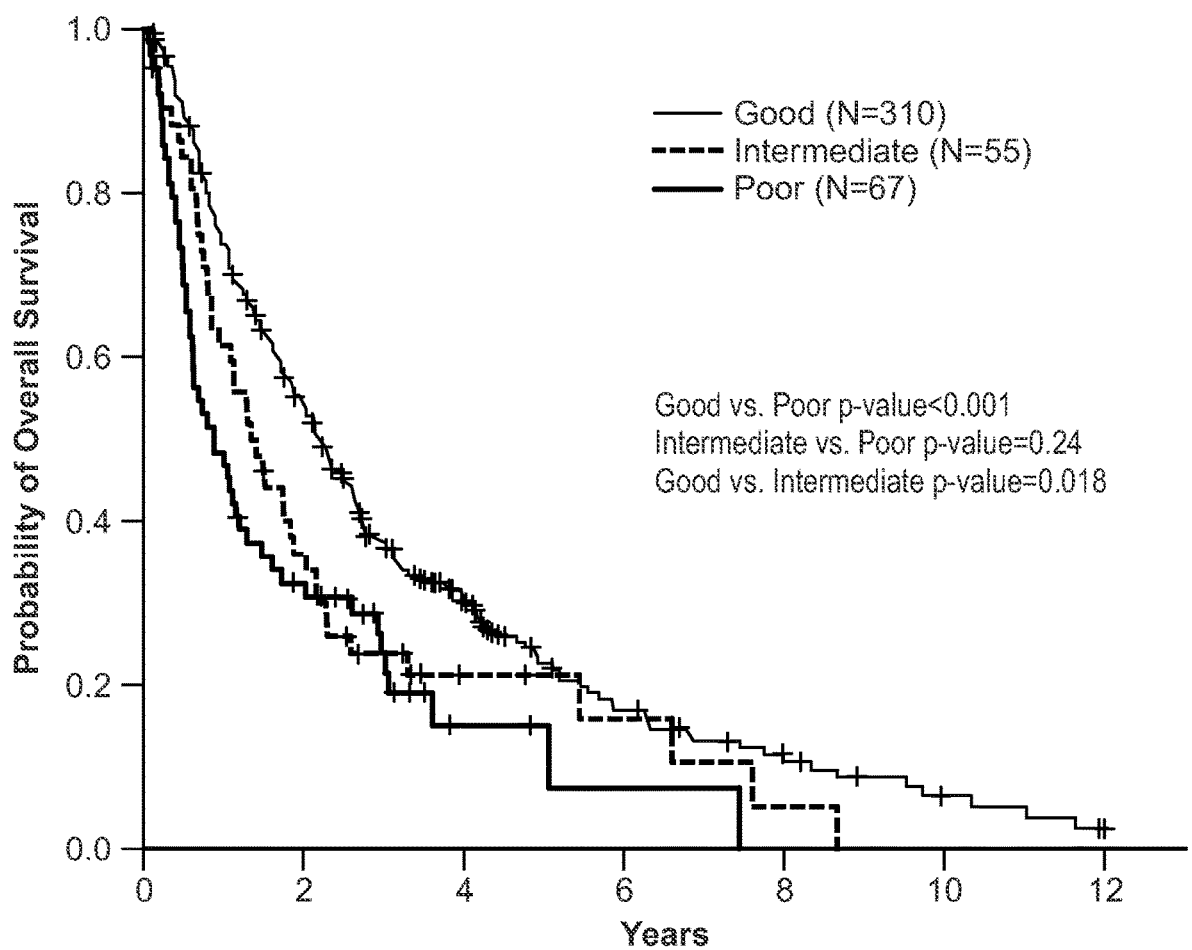
Figures 6A, 6B:
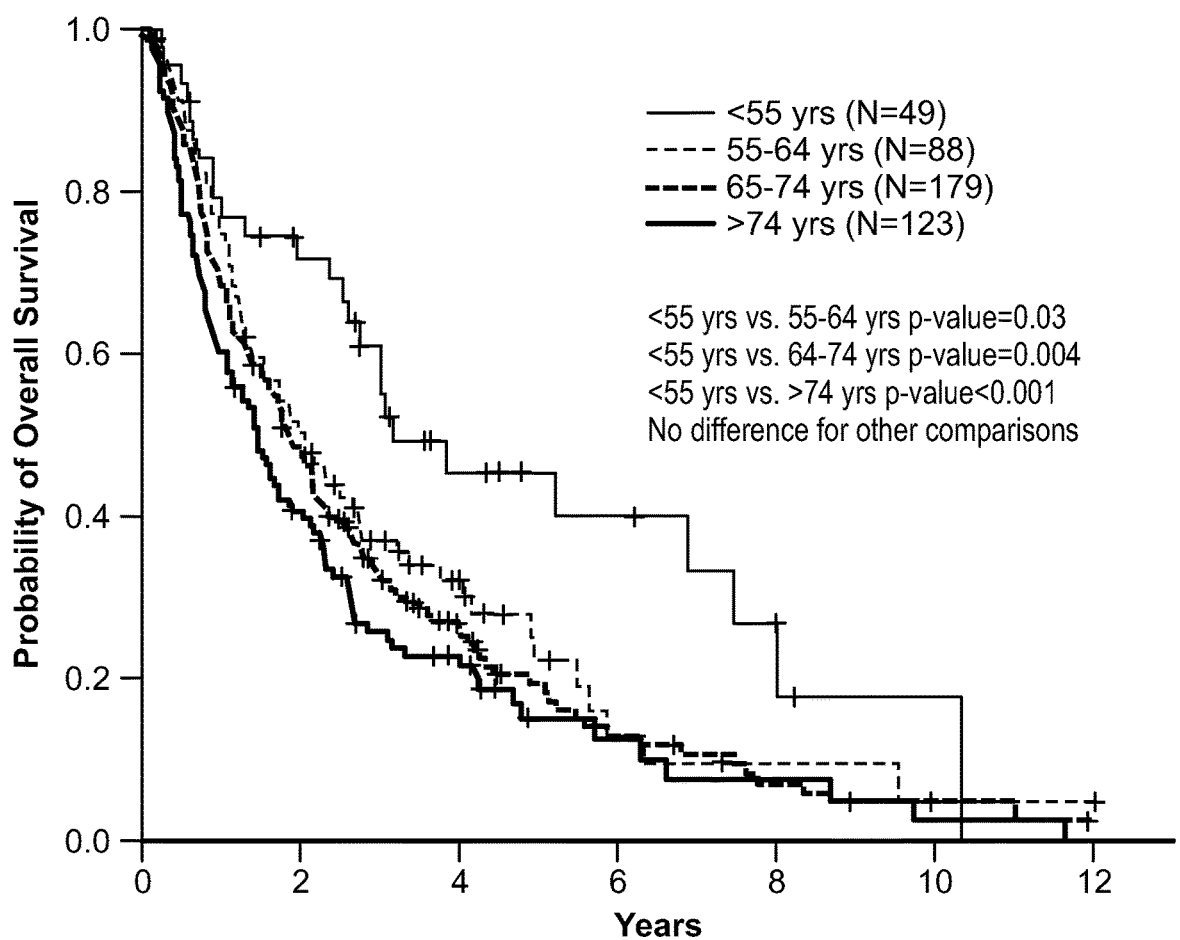
FIG. 6 shows the association of age with mutations and overall survival. Panel A shows the distribution and frequency of mutation and karyotype status by patient age. Panel B is a Kaplan-Meier survival curve illustrating the overall survival of patients based on age group at the time of sample collection. Pairwise comparisons demonstrate that the survival of patients aged less than 55 is significantly different from that in every other age group, but that the survival of patients in these older age groups is not significantly different from each other.
Figure 7A:
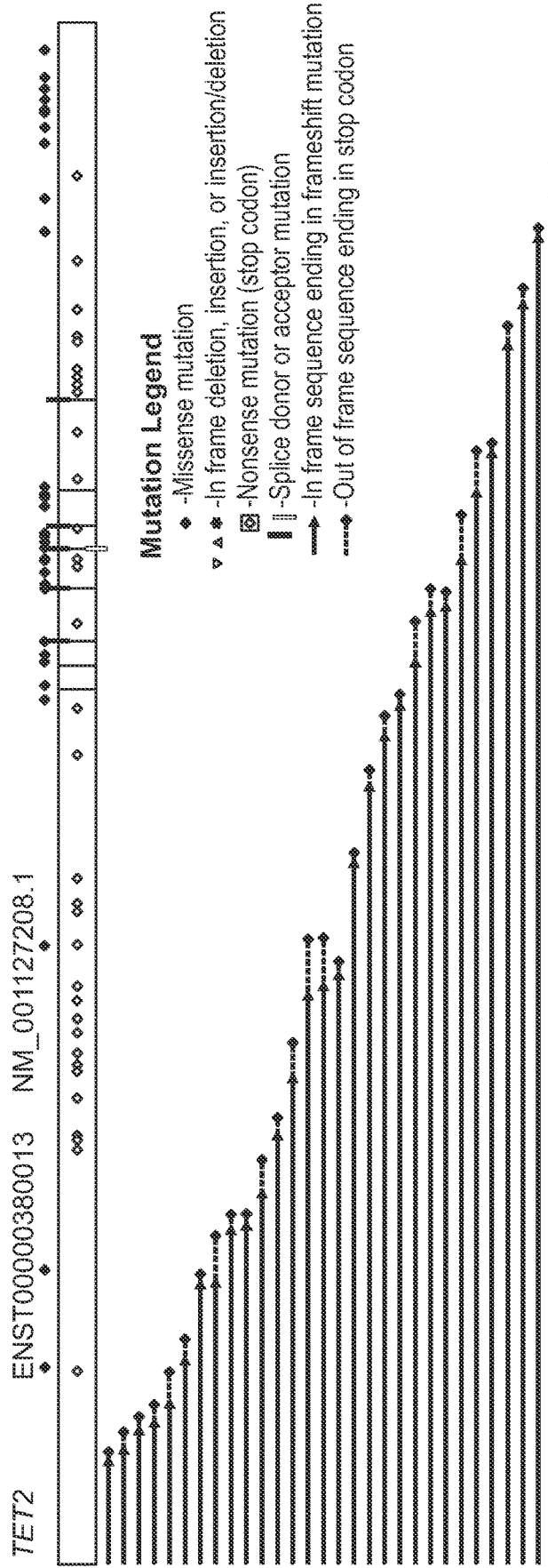
Figure 7B:
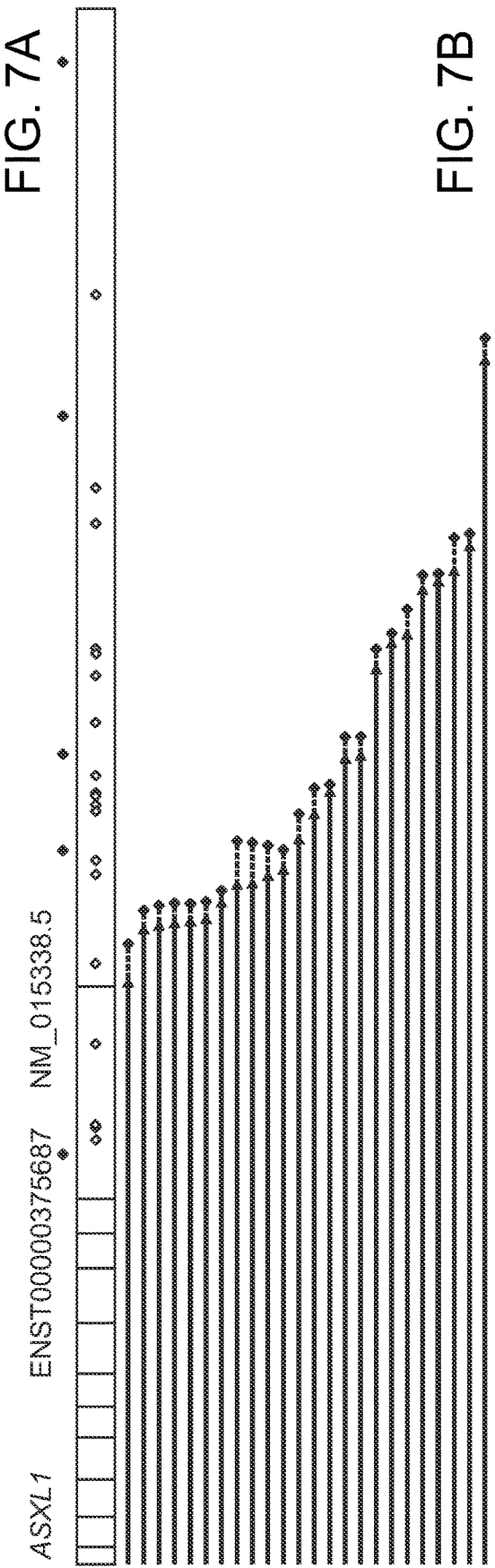

Candidate mutations detected in whole genome amplified DNA were validated using unamplified DNA (FIG. 4 and FIG. 7). IPSS risk group was determined at the time of sample collection and compared to the original IPSS classification for each patient. As shown in FIG. 4, 73 patients had their IPSS risk group change upon reclassification. Only 2 patients moved more than one category (1 from Int2 to Low and 1 from Low to Int2). FIG. 4B is a Kaplan-Meier survival plot comparing the overall survival of patients based on their reclassified IPSS. Pairwise comparisons confirm that survival of each group is significantly different from every other group.

Sanger DNA Sequencing and Analysis: Target regions in individual patient samples were PCR amplified techniques and sequenced using standard techniques, yielding 95.9% of all trimmed reads with an average quality score of 20 or more. Chromatogram data was analyzed with Mutation Surveyor v3.30 (State College, Pa.). All traces were visually inspected to identify and confirm mutation candidates.

454 DNA Sequencing and Analysis: Pools of 4 or 5 samples were combined prior to PCR amplification of target regions. Candidate mutations were called using the GS Amplicon Variant Analyzer Software and filtered for a frequency of 2% or greater. Candidate insertions and single base deletions were called by analyzing each individual aligned read and removing variants present at less than 2% frequency or predominantly in one direction. All candidate mutations were manually reviewed to confirm alignment. Mutations discovered in bidirectional reads with at least 5 reads in one direction were selected for validation by hME or Sanger sequencing.

Germline Mutation Analysis

Matched buccal DNA was available for 219 (49.9%) of the 439 samples analyzed in this study. Mutations listed in the database of single nucleotide polymorphisms (dbSNP) build 130, previously published as germline, or present in the buccal sample from any patient in our cohort were considered to be germline mutations and excluded from further analysis (Table 3).

Single Nucleotide Polymorphism (SNP) Array

DNA from 75 MDS patient samples was prepared and hybridized to Affymetrix Genome-Wide Human SNP 6.0 Array GeneChip microarrays according to the manufacturer's protocols (Affymetrix, Santa Clara, Calif.). Copy number variants were detected using the Ultrasome aberration caller (Nilsson et al. Ultrasome: efficient aberration caller for copy number studies of ultra-high resolution. Bioinformatics 2009; 25:1078-9)

Statistical Analysis

Patient characteristics were compared between groups using the Fishers exact test for categorical data, the Jonckheere-Terpstra test for ordered categorical data, and the Wilcoxon rank-sum test for continuous data (Conover W J. Practical nonparametric statistics. 3rd ed. New York: Wiley; 1999). Overall survival (OS) was measured from the time of sample collection to time of death from any cause; patients last known to be alive were censored at that time. OS curves were constructed using the method of Kaplan and Meier and compared using the log-rank test. All P values were based on 2-sided tests. For the univariate analyses of the association of clinical characteristics with each of the 18 mutations a $P \leq 0.01$ was considered statistically significant, to reflect the multiplicity of clinical features of the individual patient. For all other assessments, nominal p-values are presented.

OS was evaluated for all patients using unadjusted and adjusted Cox proportional hazard regression modeling; models were adjusted for IPSS risk group at the time of sample collection. The prognostic significance of each mutation was determined using step-up models evaluated using the −2 Log likelihood statistic (Collett D. Modelling survival data in medical research. 2nd ed. Boca Raton, Fla.: Chapman & Hall/CRC; 2003). The full model including mutational status and IPSS risk was compared to the null model including only IPSS risk using the difference in −2 Log likelihood and tested using a chi-square distribution with the appropriate degrees of freedom. Candidate explanatory variables in the stepwise Cox regression modeling included age (categorized as <55 vs. ≥55 years), IPSS risk, sex, and the 13 mutations with ≥1% frequency (of the 18 examined as potential prognostic features). The same final model was obtained using a forward variable selection procedure. The categories for age were determined using a recursive partitioning algorithm based on OS. SAS version 9.2 and R version 2.8.0 were used for all analyses.

Figure 8:
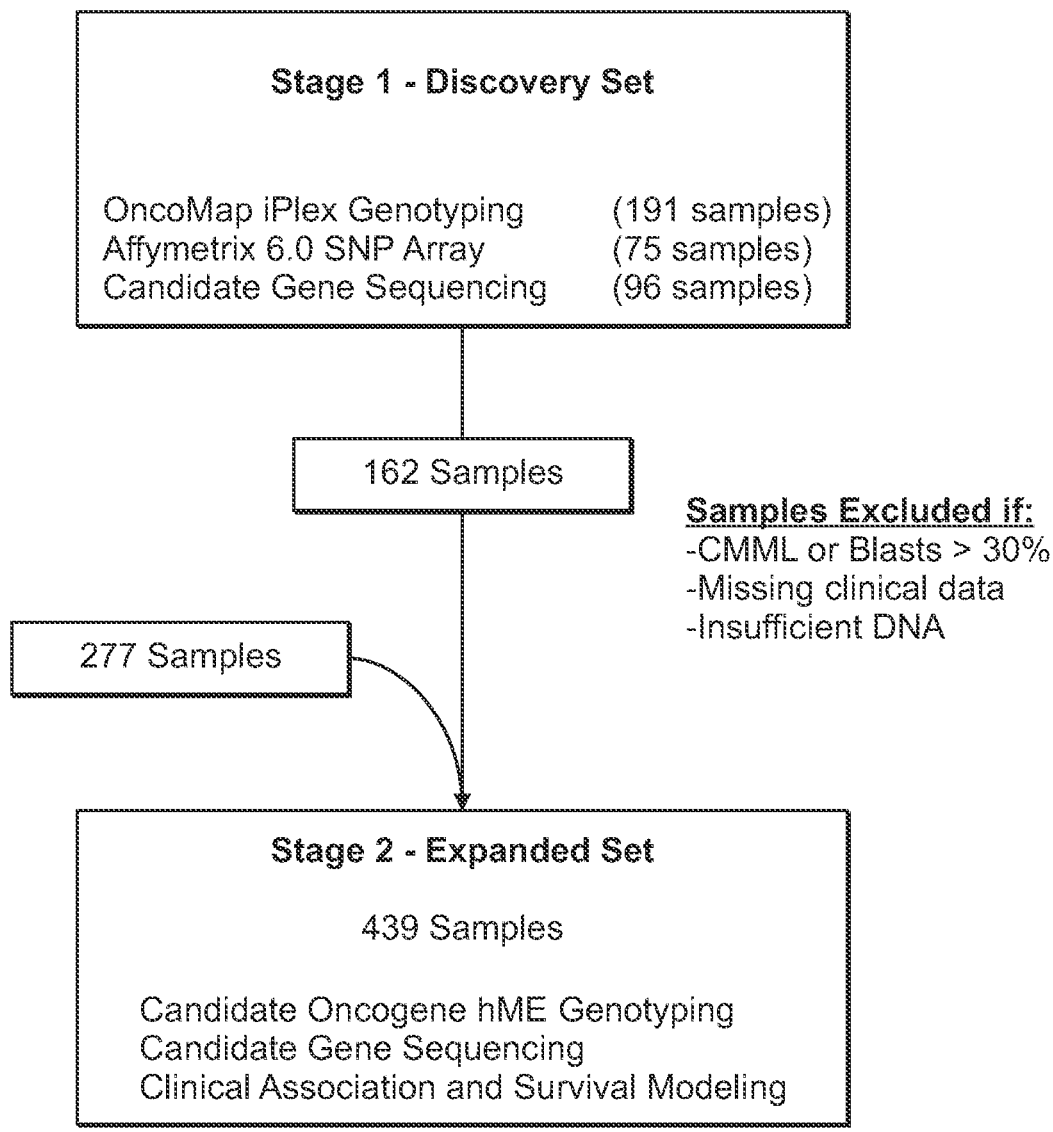
FIG. 8 is a diagram of two-stage study design.

Example 2: Mutations in Myelodysplastic Syndromes are Independent Predictors of Overall Survival and are Associated with Clinical Features Identification of Novel Somatic Mutations in MDS To identify mutations that alter the morbidity and mortality of patients with MDS, we performed a genetic analysis of a large, clinically annotated collection of bone marrow aspirates from MDS patients. We first performed a deep genetic analysis of a subset of samples to define a set of mutations in MDS, and subsequently analyzed all of the genes with validated mutations in our full sample set, as illustrated in the schema in FIG. 8.

Using mass spectrometric genotyping, we surveyed 191 MDS samples for 953 recurrent mutations in 111 cancer-associated genes.[20] We identified and validated mutations in 10 genes: NRAS, KRAS, BRAF, JAK2, GNAS, FLNB, MET, EGFR, CDH1 and PTPN11. Genotyping of germline DNA from buccal swabs demonstrated that mutations in each gene were somatic except for those in MET (E168D, 3 cases), EGFR (T790M, 1 case), and CDH1 (A617T, 3 cases). No germline sample was available for the sole patient with a mutation in FLNB (R566Q). These studies therefore confirmed somatic mutations in five genes (NRAS, KRAS, BRAF, JAK2, PTPN11) known to be mutated in MDS and discovered recurrent mutations in GNAS that have not been previously reported in hematologic malignancies.

Figure 9:
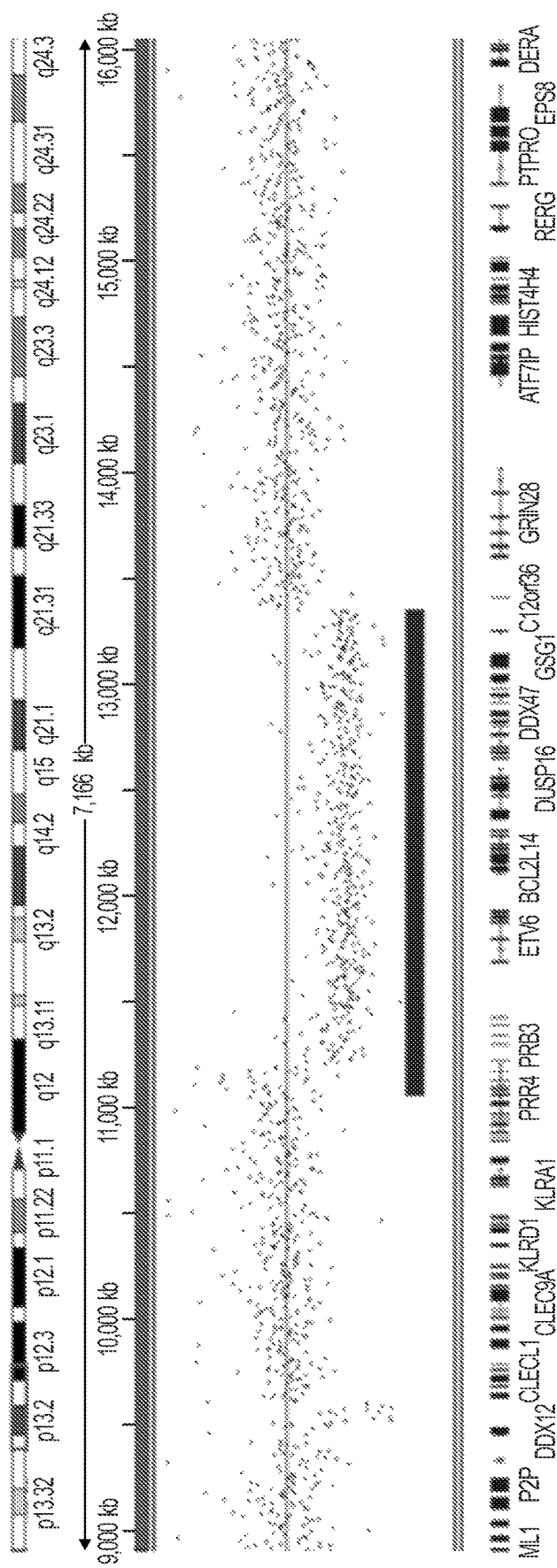
FIG. 9 shows that copy number results from an MDS bone marrow sample genotyped on an Affymetrix 6.0 SNP array demonstrates an interstitial 2.3 megabase deletion on chromosome 12p that includes the ETV6 gene locus.
Figure 10A:
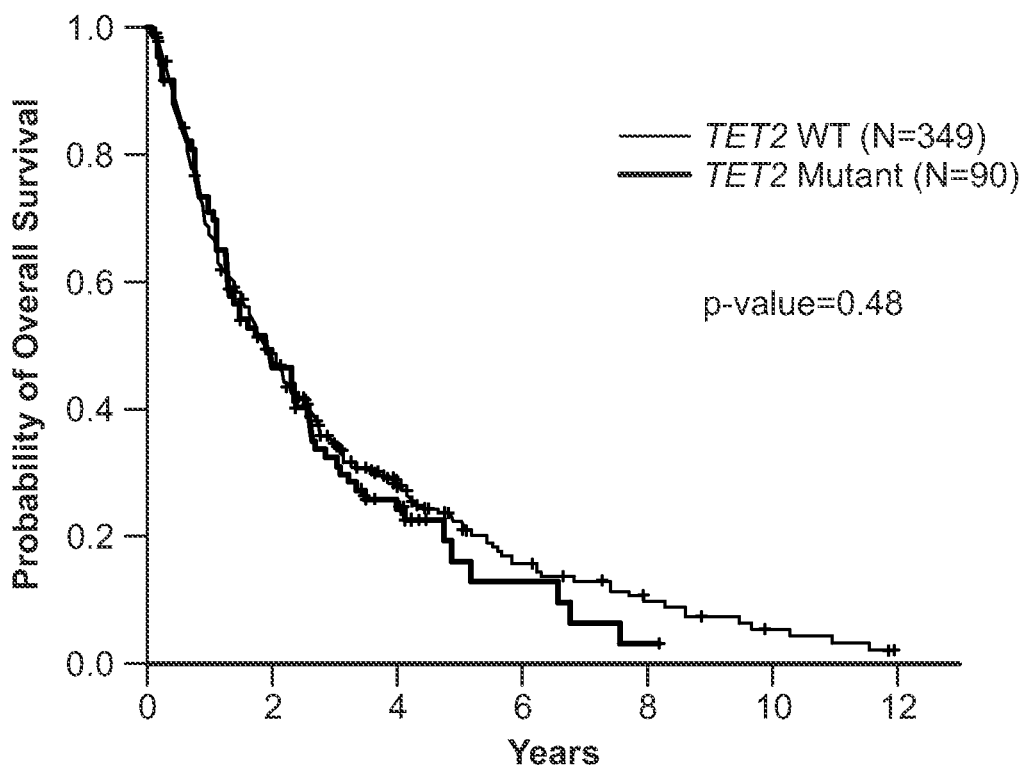
FIGS. 10A-10M show Kaplan-Meier survival curves for mutations. Each panel shows the proportion of surviving patients with a given mutation (red line) compared to patients without that mutation (black line). The numbers of unmutated vs. mutated cases are shown in parentheses, respectively. The log-rank p-value is provided comparing the survival of the two groups in each panel.
Figure 10B:
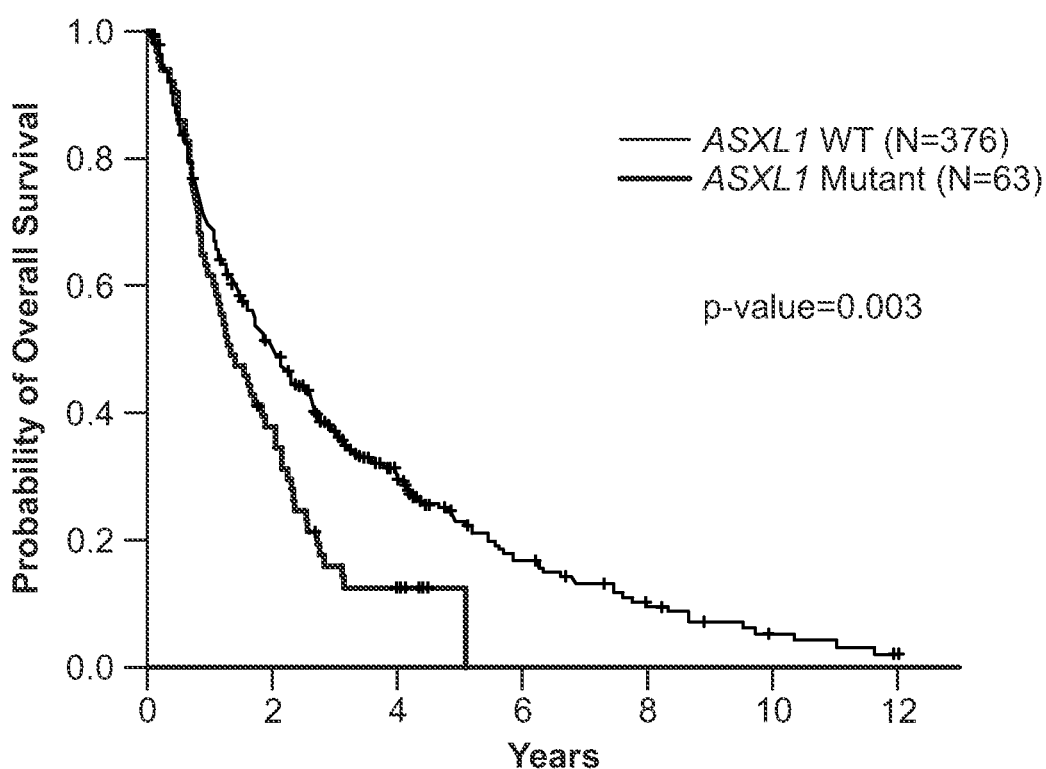
Figure 10C:
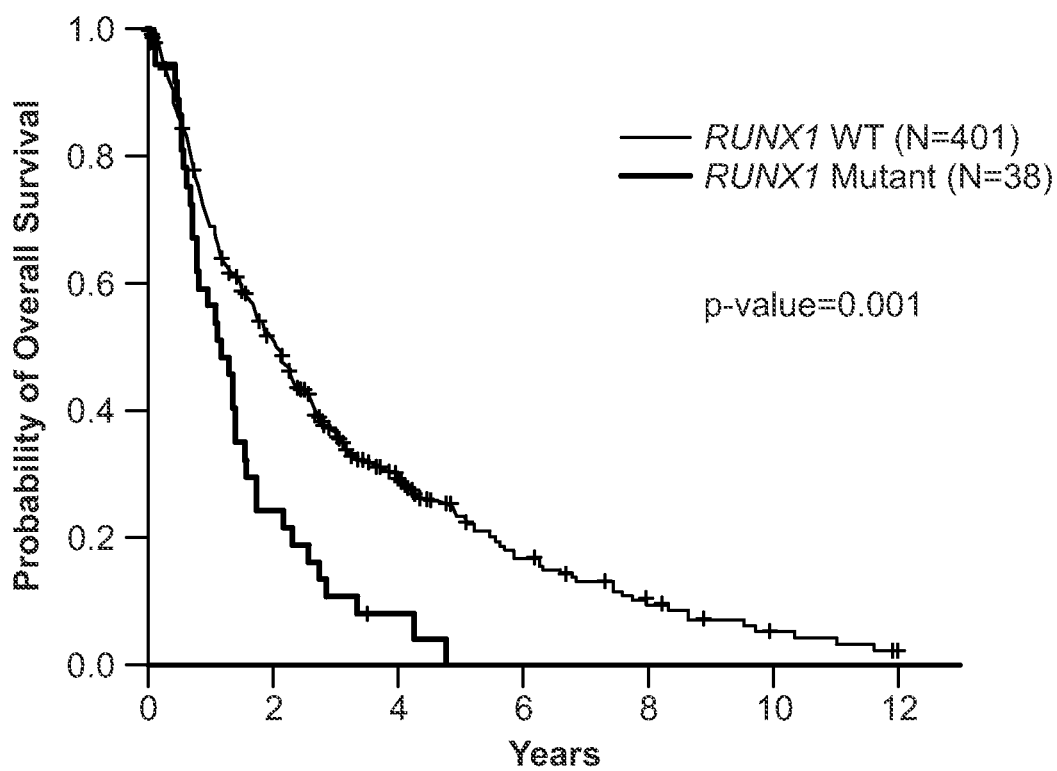
Figure 10D:
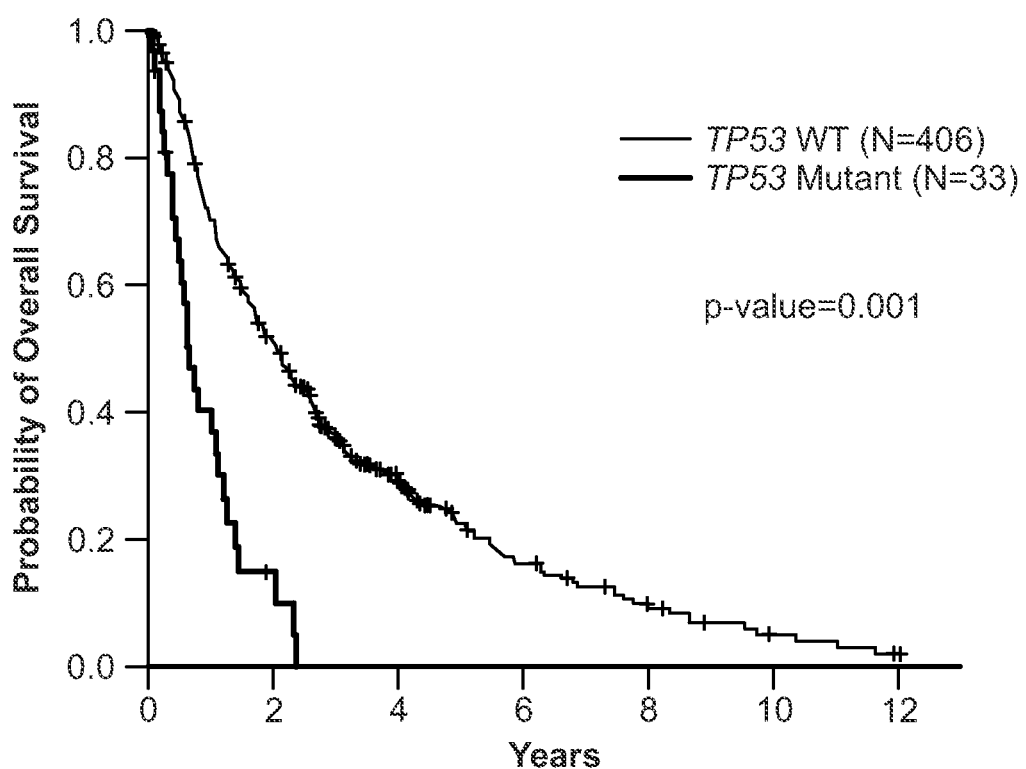
Figure 10E:
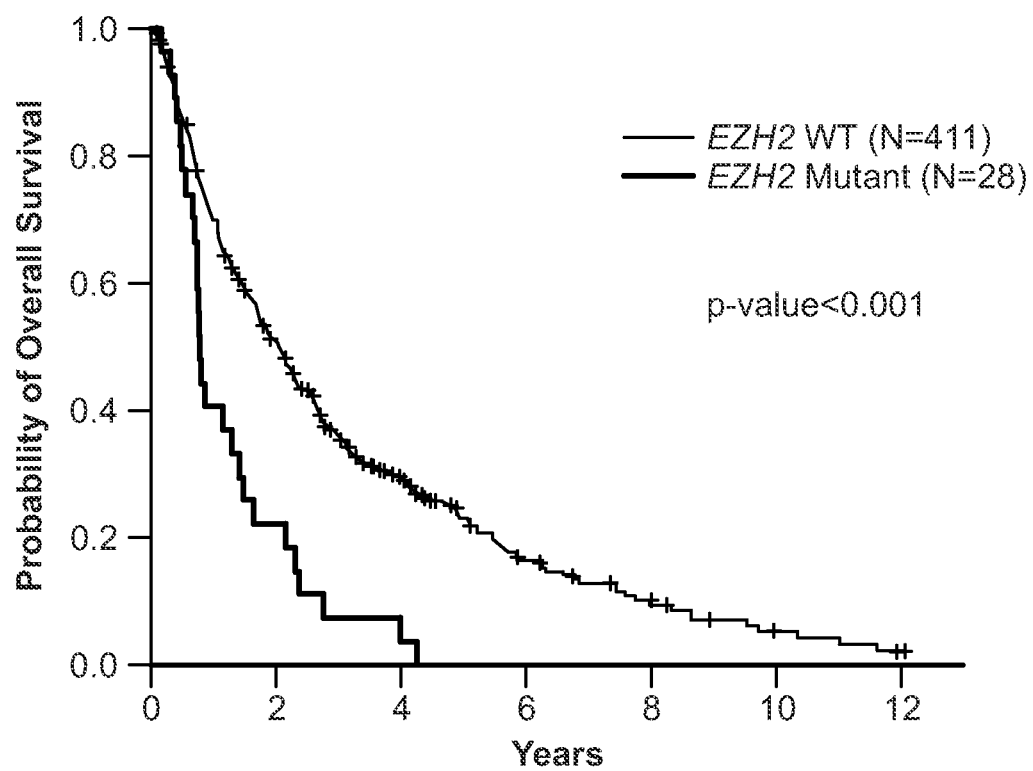
Figure 10F:
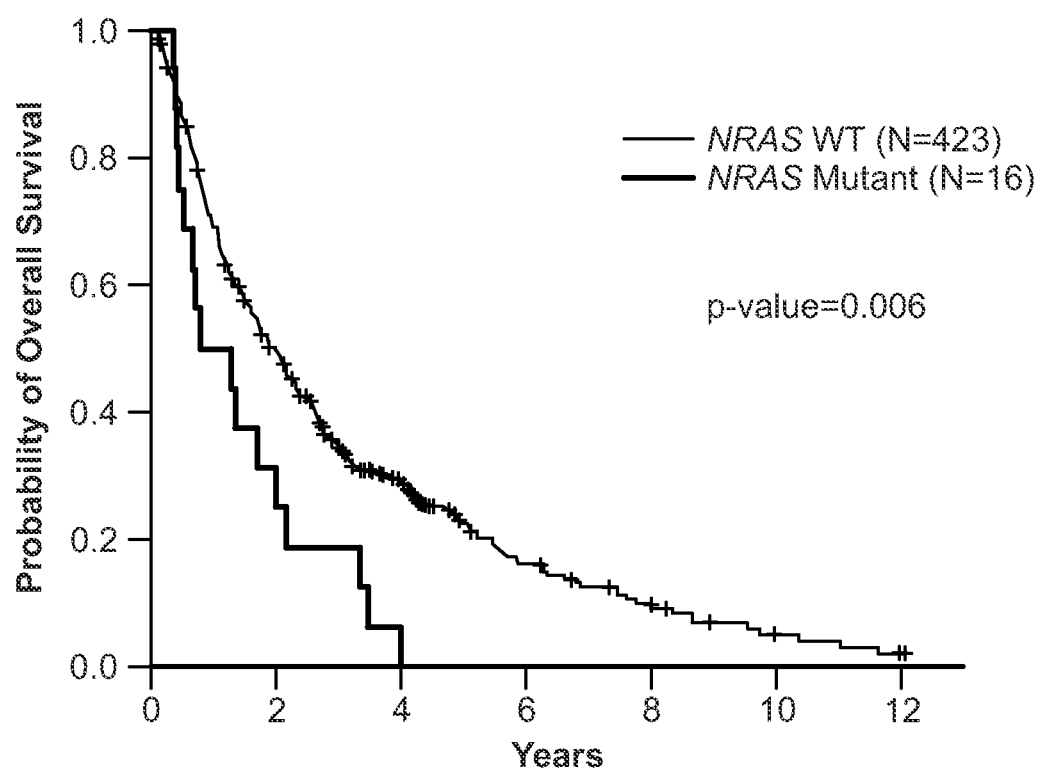
Figure 10G:
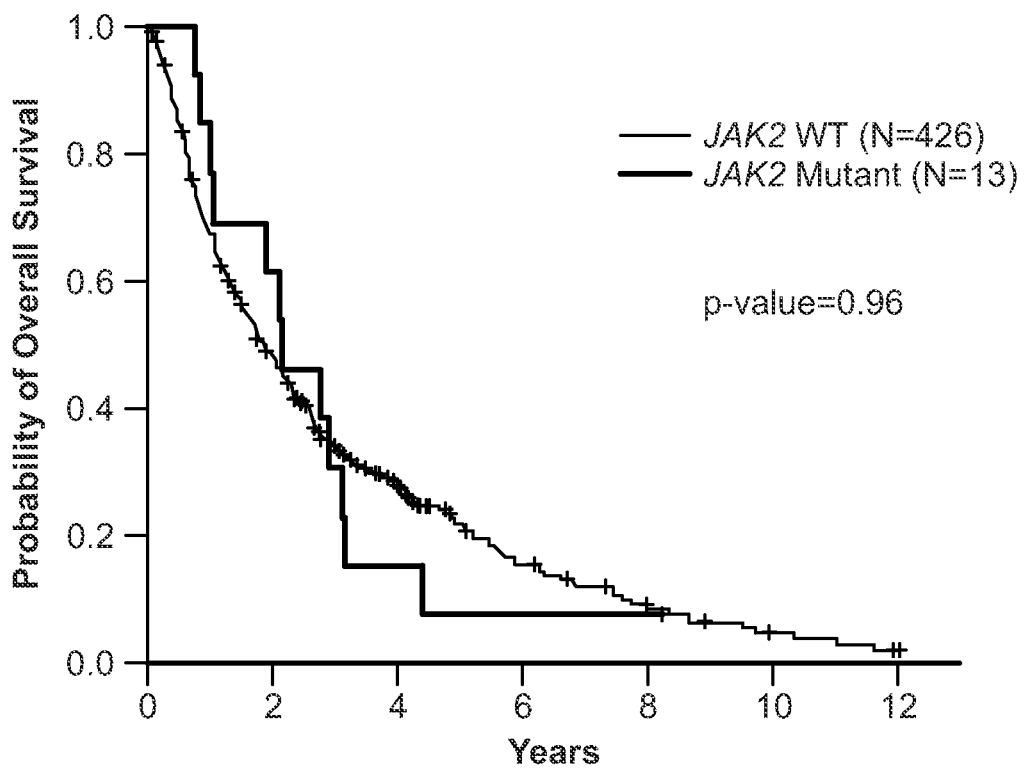
Figure 10H:
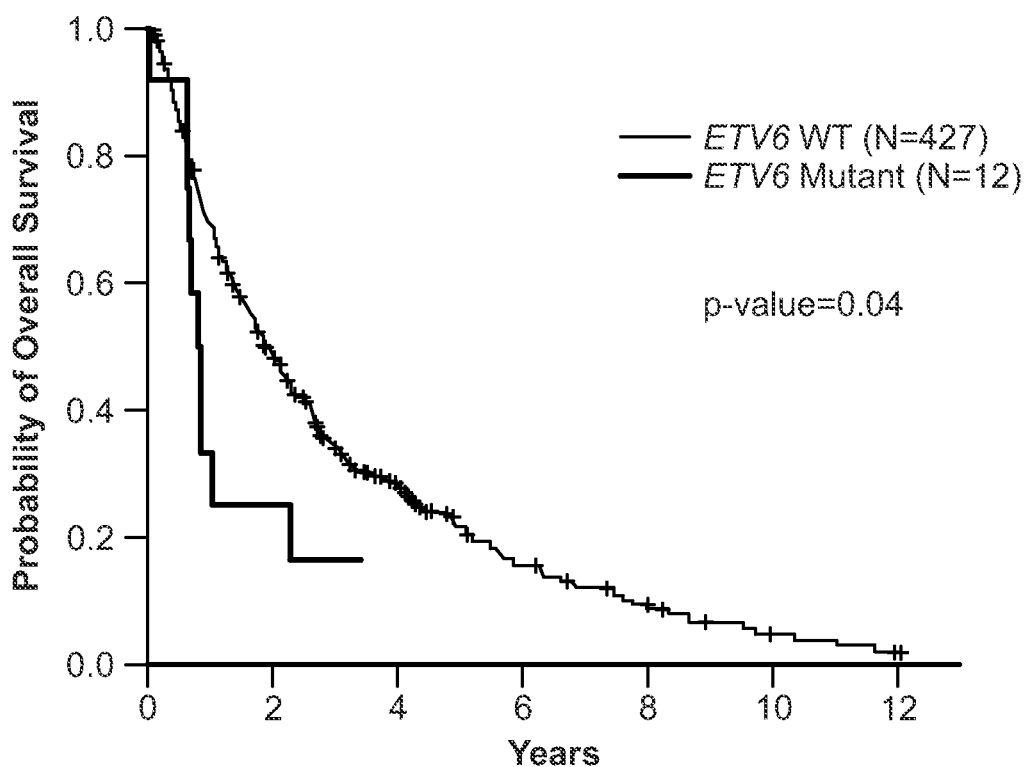
Figure 10I:
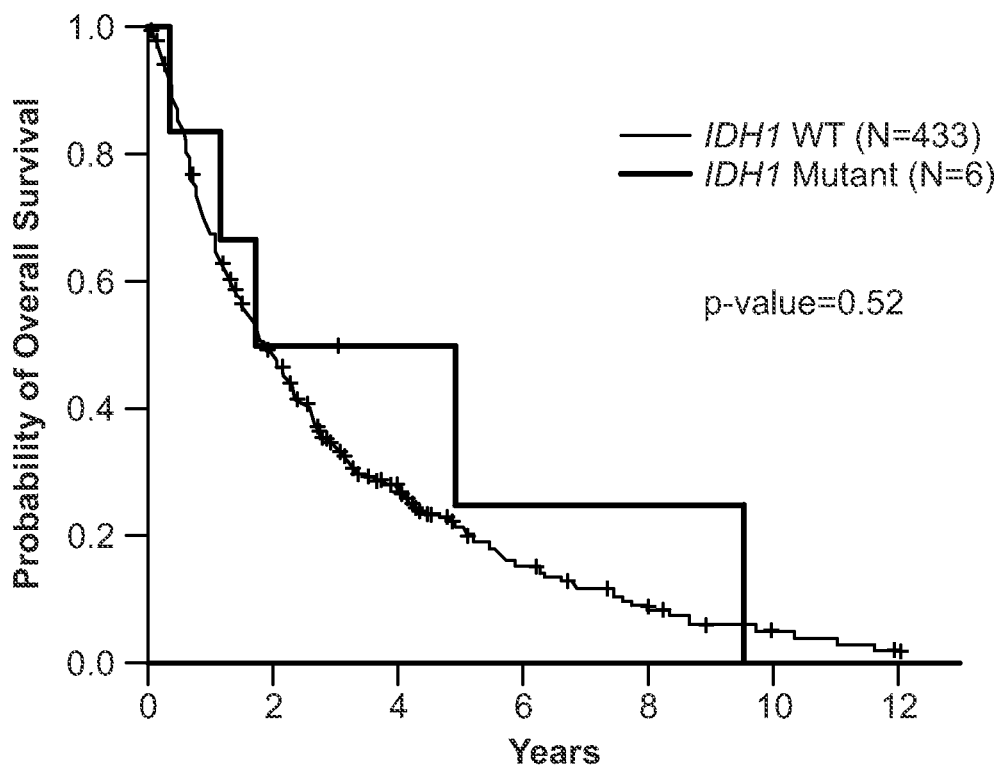
Figure 10J:
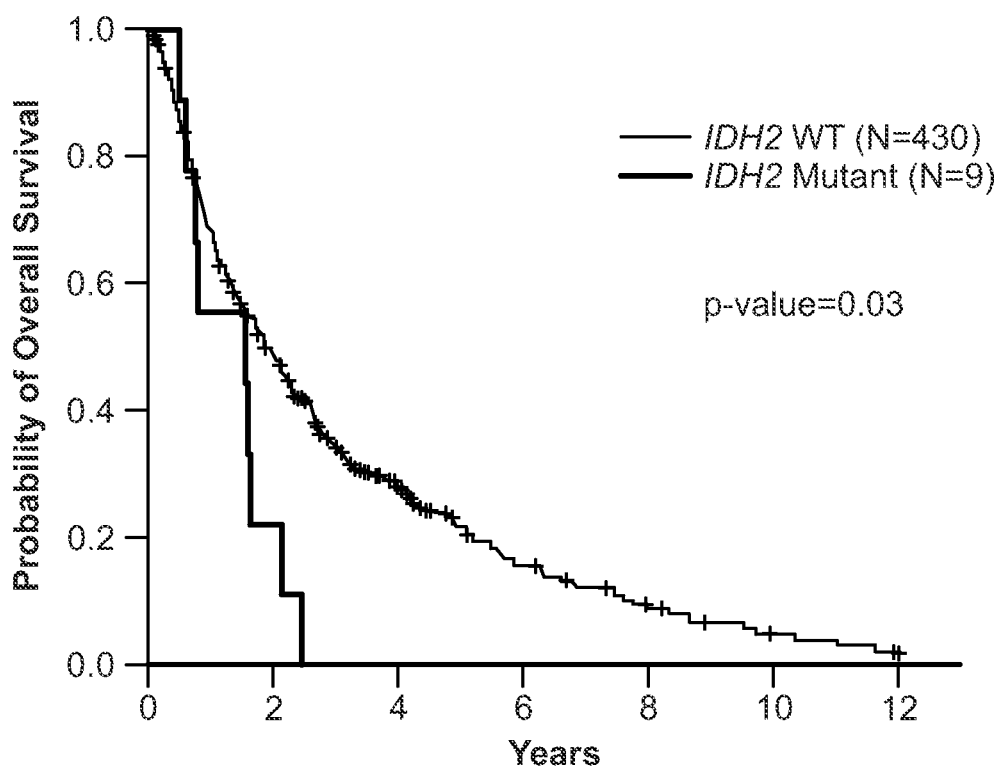
Figure 10K:
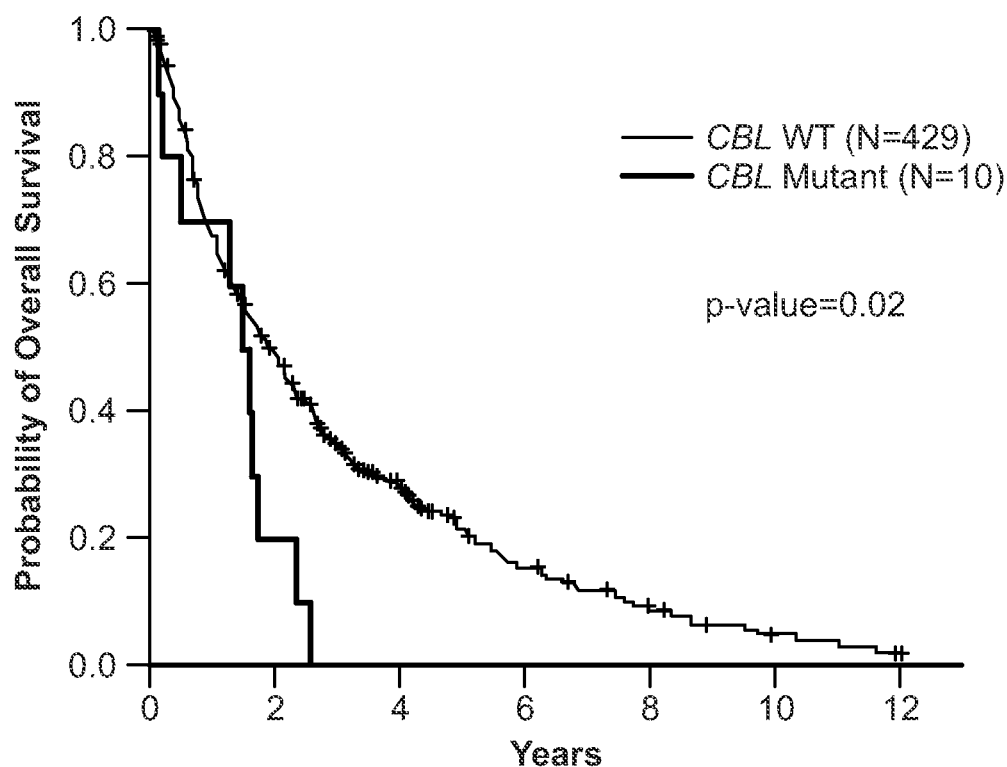
Figure 10L:
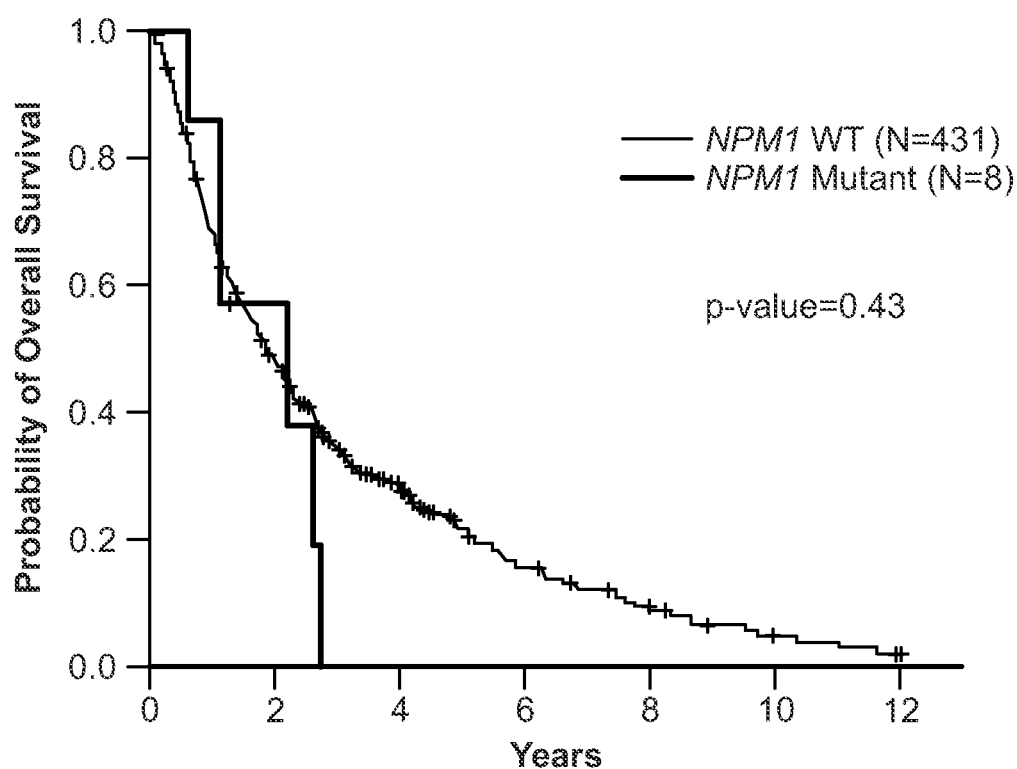
Figure 10M:
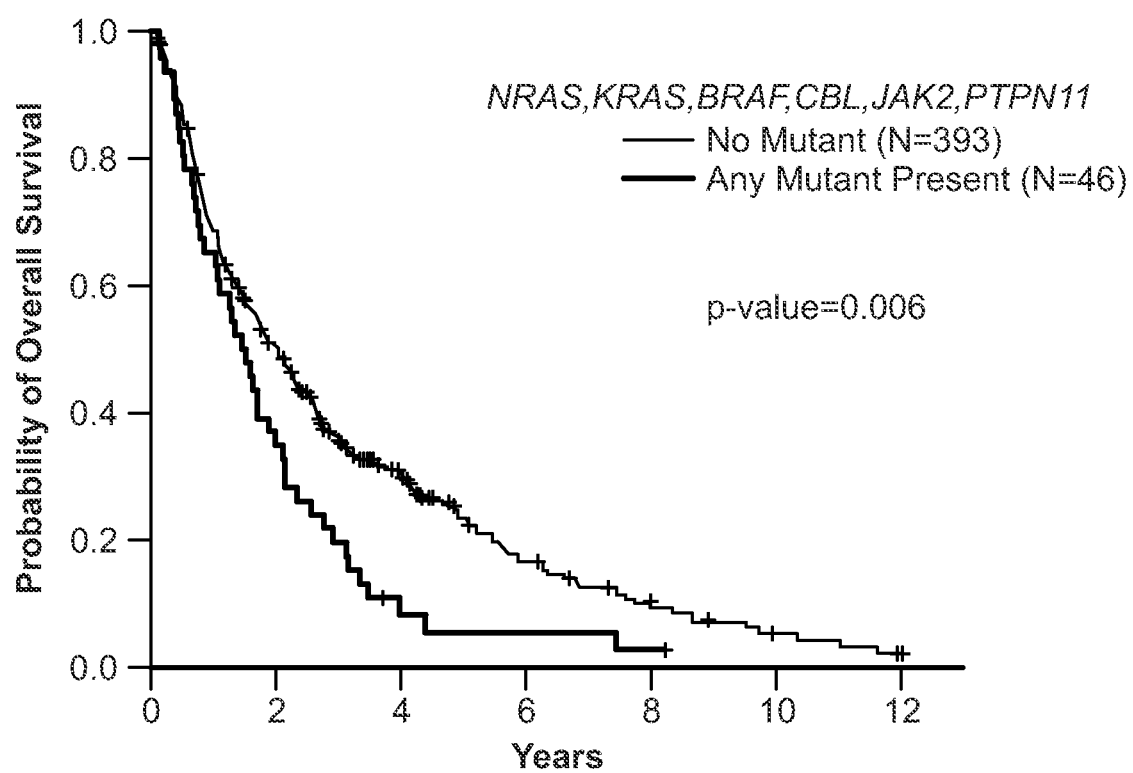

We performed genome-wide analysis of copy number changes using Affymetrix 6.0 SNP arrays in a 75 patient sample subset. In addition to the known cytogenetic abnormalities, we identified a single case with a focal deletion encompassing ETV6 (TEL), a gene that is recurrently involved in translocations in acute leukemia but not known to be mutated in MDS (FIG. 9). Subsequent sequencing of this gene in other samples revealed several point mutations confirmed to be somatic by examination of matched buccal swab DNA.

Survey of Mutations in 439 MDS Samples

To examine the clinical impact of mutations in MDS, we evaluated all genes identified above, plus a set of 13 genes previously reported to be mutated in hematologic malignancies in samples from 439 patients with demographics representative of the general population of patients with MDS (Table 1). At the time their bone marrow aspirate was collected, this group had a median age of 70 years and included 70% males, 66% with lower IPSS risk, 58% with normal cytogenetics, and 13% with complex cytogenetics, all values comparable to those reported in published epidemiologic studies.[22-24, 2]

We identified mutations in 18 genes in our set of 439 MDS samples (Table 6). At least one mutation was present in 226 samples (51.5%). Abnormalities of KDM6A (UTX) were found in three samples, but these missense mutations could not be confirmed as somatic and are not included in the totals listed above.

The frequency of coexisting somatic mutations can yield insights into the molecular circuitry of a cancer. Mutations of two or more genes were present in 79 (18.0%) samples (FIG. 1, Table 4). As has been reported previously, mutations of genes involved in tyrosine signaling pathways (JAK2, CBL, and NRAS/KRAS/BRAF) were largely mutually exclusive. TET2 mutations, in contrast, overlapped with lesions in nearly every other mutated gene, suggesting that TET2 mutations have a pathogenic role that is at least partially independent of other abnormalities.

Associations Between Mutations and OS

Abnormalities in seven genes were significantly associated with poor OS in univariate analyses (Table 6, FIG. 10). Mutations in six genes, ASXL1, RUNX1, TP53, EZH2, CBL and ETV6 were significant predictors of poor OS after adjusting for IPSS risk group and were found in 74 out of 255 patients (29.0%) with normal cytogenetics.

Associations of Mutations with Cytogenetics and Cytopenias

The prognostic significance of point mutations in MDS may be driven by association of these mutations with risk factors including karyotype, blast proportion, and cytopenias captured by existing clinical risk scores such as the IPSS. We therefore compared the clinical characteristics of patients with each mutation to patients without the respective lesion.

The mutated genes most strongly associated with a specific karyotype group were TET2 and TP53. Mutations of TET2 were overrepresented in samples with normal cytogenetics (p=0.005, Table 5), while TP53 mutations were strongly associated with complex cytogenetics (p<0.001). Eight of the 33 (24.2%) TP53 mutant samples had abnormalities of chromosome 17 (p<0.0001), suggesting that combined mutation and chromosomal loss frequently cooperate to abrogate wild type TP53 activity. In contrast, mutations of the EZH2 gene, which lies on the distal portion of chromosome 7q, were not associated with 7q deletions.

Figure 2A:
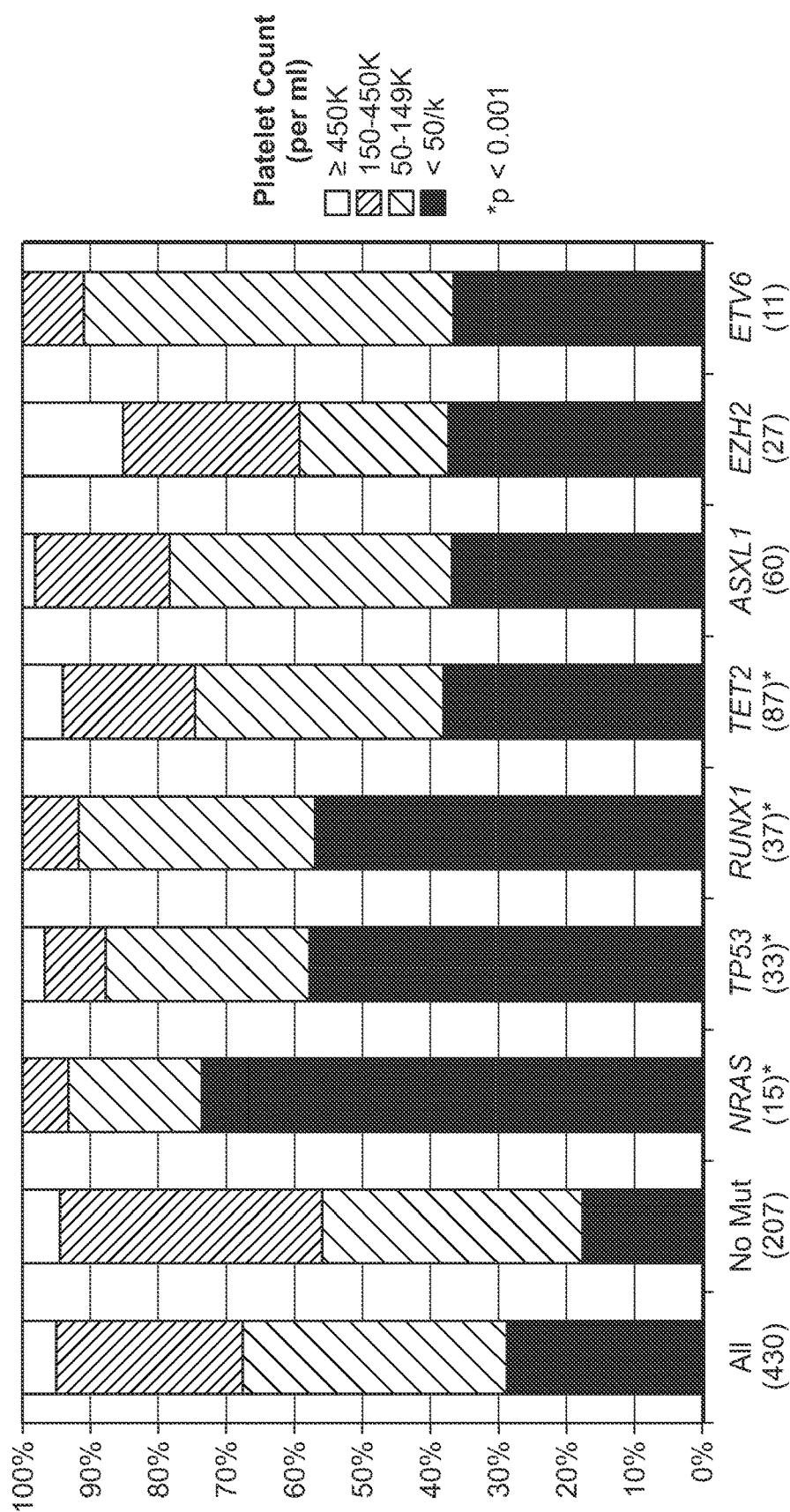
FIGS. 2A-2C show mutation associations with cytopenias and bone marrow blast percentage. The proportion of patients in each clinical parameter group is plotted by mutation status. The numbers in parentheses indicate the number of cases for which the measure was known. Statistical comparisons were made between cases with a particular mutation to those without it.
Figure 2B:
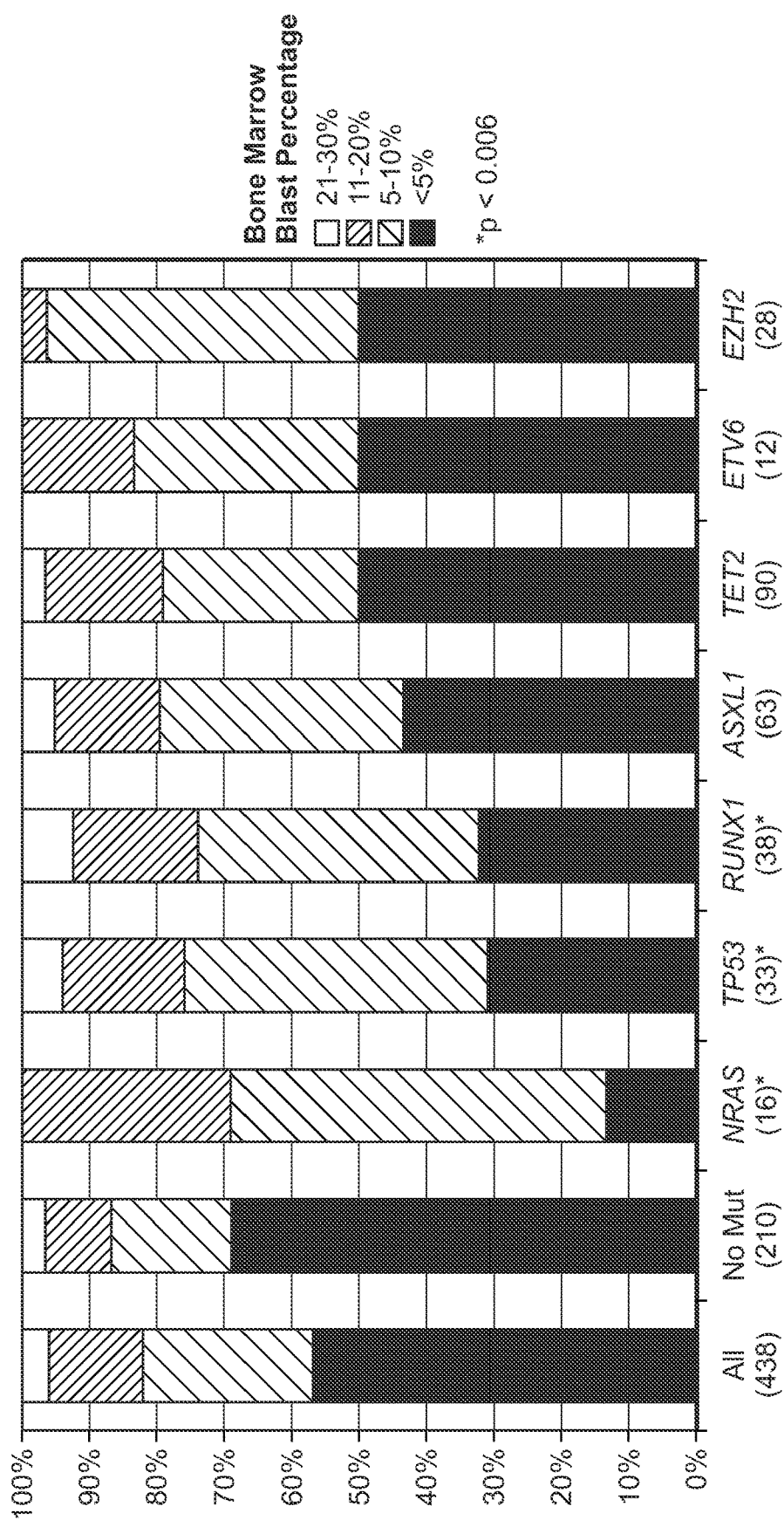
Figure 2C:
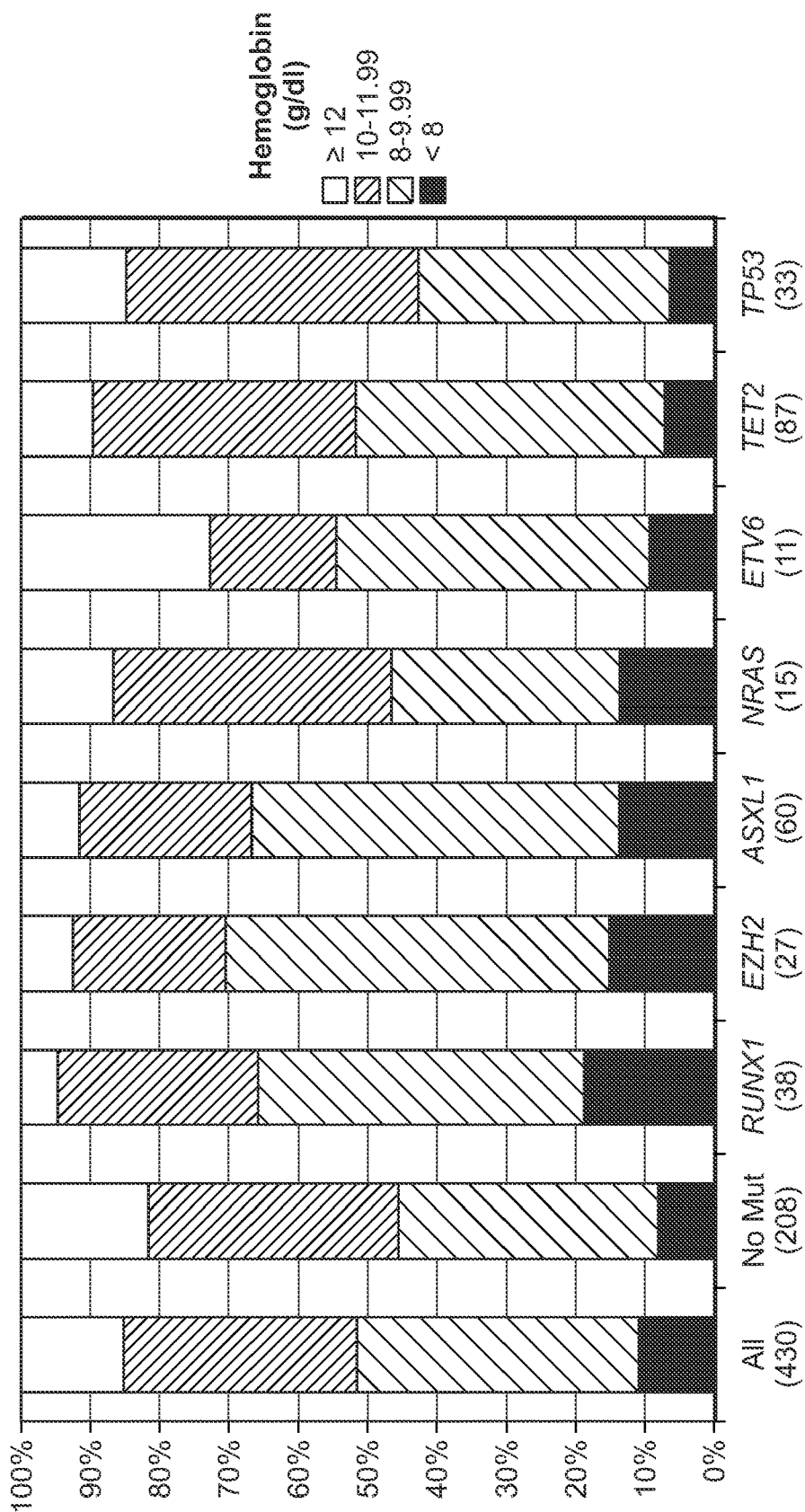
Figure 3A:
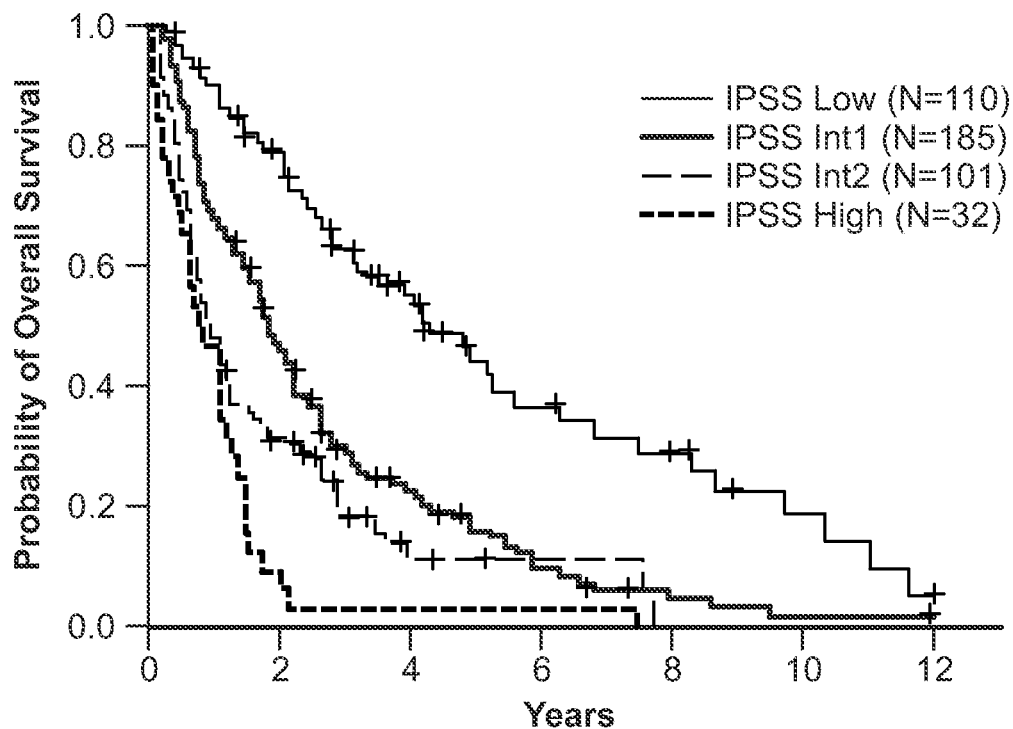
FIG. 3 shows the association of prognostic mutations with overall survival stratified by IPSS risk group. Panel A shows the OS of patients within each IPSS risk group. Panel B shows the OS of patients with mutations in one or more prognostic genes (TP53, EZH2, ETV6, RUNX1, or ASXL1) compared to the OS of patients with no such mutations. Panels C-F show the OS of patients with and without prognostic mutations for each IPSS risk group. In panels C-E, the OS curve for patients in the next highest IPSS risk group is included for the purpose of comparison. In panel F, the comparator curve is that of patients in the Int2 IPSS risk group. The p-value in each panel represents a log-rank comparison of OS between those patients with prognostic mutations and those without for the given IPSS group.
Figure 3B:
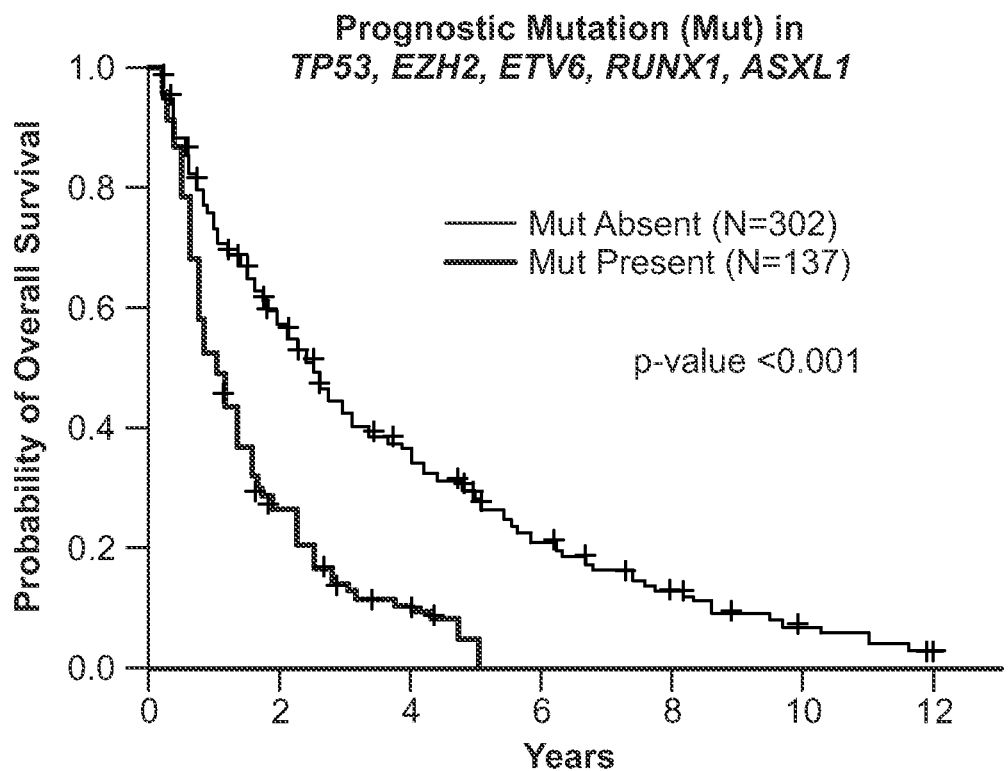
Figure 3C:
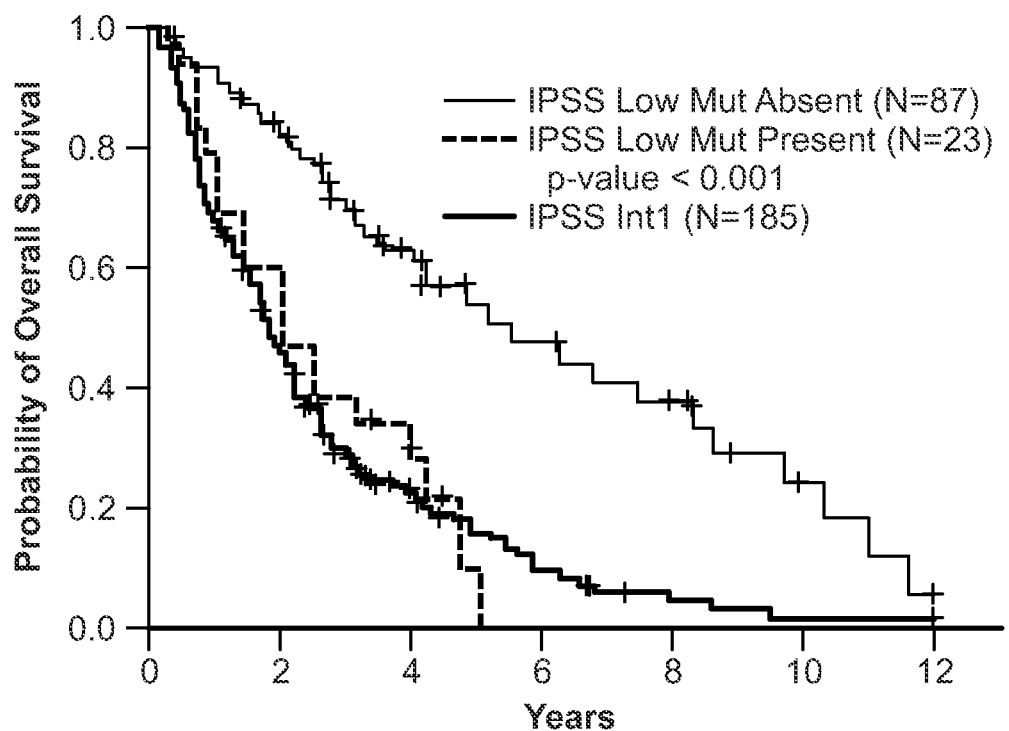
Figure 3D:
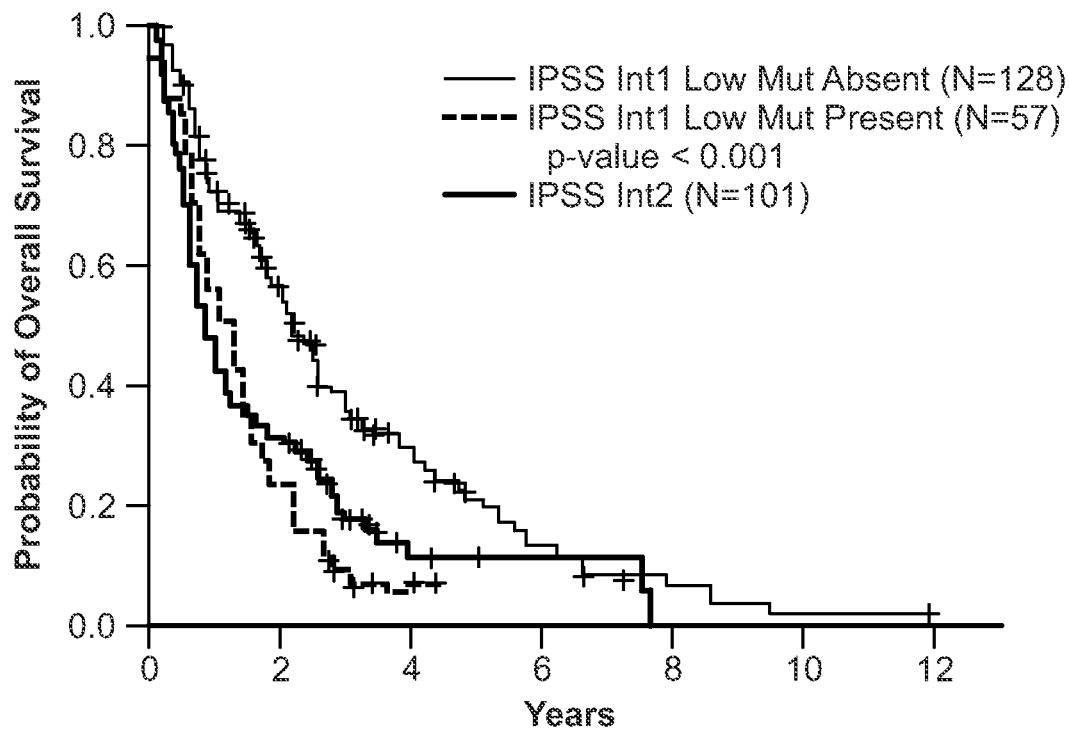
Figure 3E:
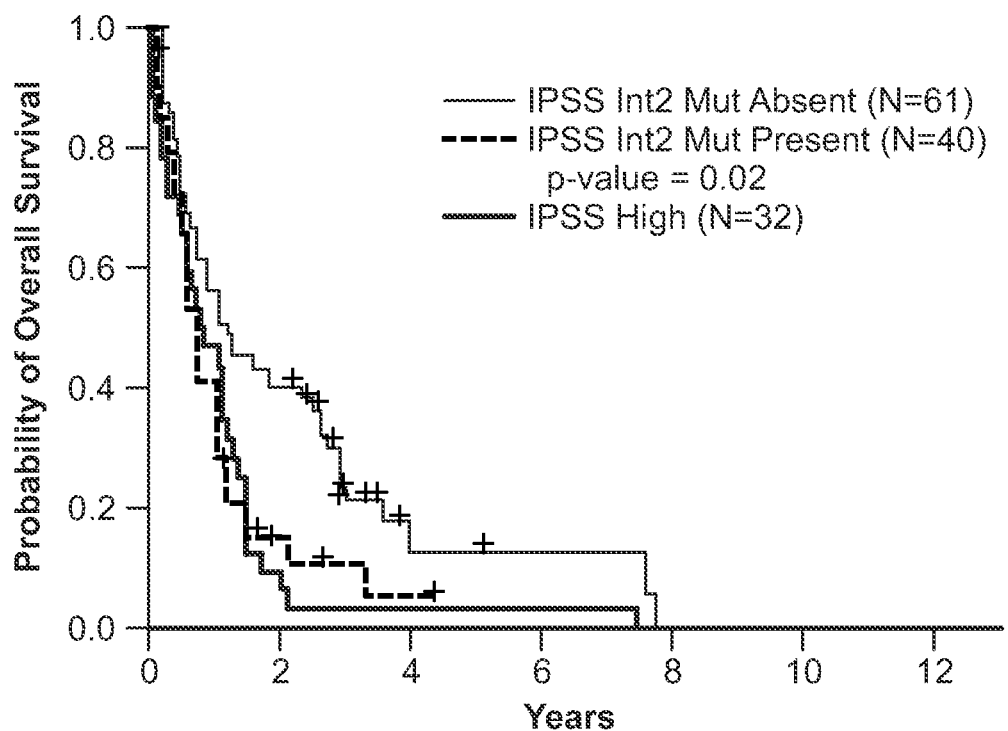
Figure 3F:
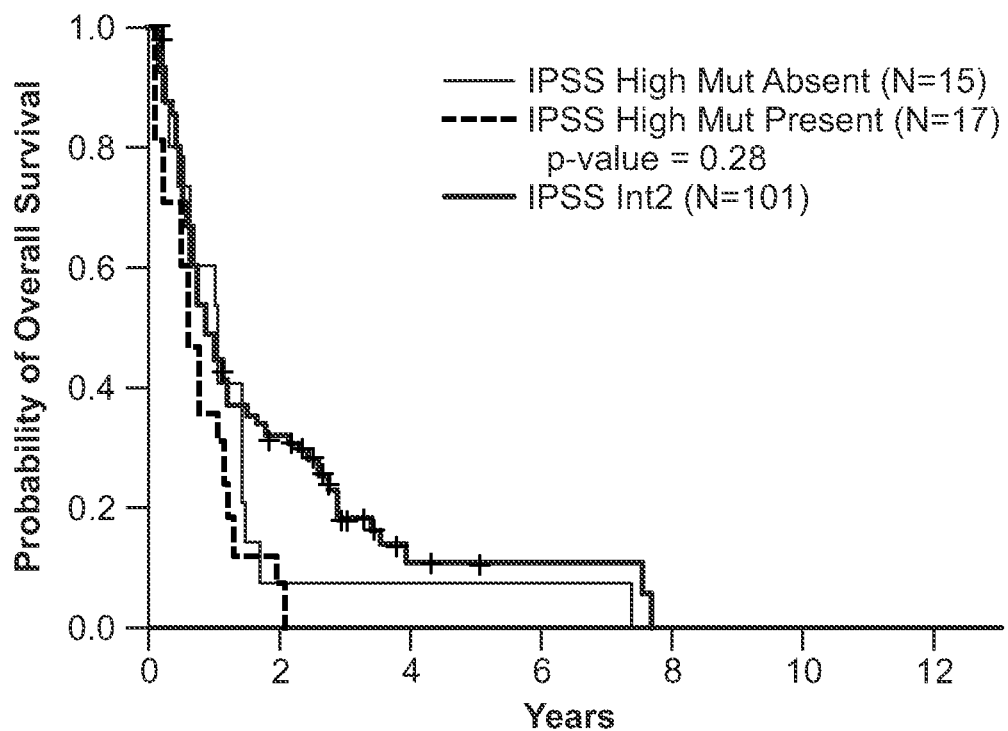

MDS is characterized by ineffective hematopoiesis and impaired differentiation leading to peripheral blood cytopenias, but the contribution of specific genotypes to particular cytopenias is unknown. We observed that mutations of RUNX1, TP53, and NRAS were each strongly associated with severe thrombocytopenia (FIG. 2A, p<0.001 for each gene). Patients with mutations of these genes were also more likely to have an elevated blast percentage (FIG. 2B), but had no difference in the degree of neutropenia or anemia (FIG. 2C). These findings demonstrate how the association of some mutations with poor survival may be indirectly captured by the IPSS due to their associations with cytopenias, blast percentage, and karyotype.

Multivariable Survival Model

Mutations in multiple genes were associated with OS in univariate analyses (Table 6). However, these mutations often co-occur with each other and several were associated with established prognostic markers. To determine the relative contribution of mutation status to OS, we generated a multivariable Cox model using a stepwise variable selection procedure incorporating age, sex, IPSS, and mutation status for the 13 most frequently mutated genes identified in this study. As expected, patient age and IPSS risk group were strongly associated with OS (Table 7).

Mutations in TP53, EZH2, ETV6, RUNX1, and ASXL1 emerged as independent predictors of survival. Mutation of NRAS, which has previously been reported as a marker of poor prognosis, did not retain its association with survival in this model likely due to strong associations between oncogenic NRAS mutations and components of the IPSS. EZH2 mutations, which were not associated with known prognostic markers, retained their high hazard ratio in the model. This analysis indicates that evaluation of mutation status for TP53, EZH2, ETV6, RUNX1, and ASXL1 would add the most information to existing prognostic scores in patients with MDS.

One approach to the integration of mutations into the IPSS would be to include a variable for mutations in one or more of these 5 prognostic genes (FIG. 3). In all but the highest risk patients, these mutations are associated with an OS comparable to that of patients in the next highest IPSS risk group.

Remarks

In a broad survey of mutations in 439 MDS primary samples, we identified point mutations in 18 genes, including two (ETV6 and GNAS) that have not previously been reported as mutated in this disorder. We found that several of these genetic lesions correlate strongly with important features of clinical phenotype, including specific cytopenias, blast percentage, cytogenetic abnormalities, and OS. In a multivariable analysis including clinical parameters and other mutations, TP53, EZH2, ETV6, RUNX1, and ASXL1 mutations were each independently associated with decreased OS. Mutations in one or more of these genes were present in 137 of the 439 (31.2%) patients. These findings indicate that mutations in specific genes help explain the clinical heterogeneity of MDS and that the identification of these abnormalities would improve the prediction of prognosis in MDS patients, aiding the selection of appropriate therapies.

Analyzing copy number alterations with SNP arrays and oncogene mutations by high throughput genotyping, we identified novel mutations in ETV6 and GNAS. Rare ETV6 translocations have been described in MDS, and mutations have been identified in AML, but to our knowledge, ETV6 mutations have not been previously reported in MDS.[25,26] We also identified 3 cases with activating mutations of amino acid R201 in GNAS, the gene encoding the $G_{S\alpha}$-subunit of the heterotrimeric GS-protein complex. Identical somatic activating mutations of GNAS have been identified in several solid tumor types, but not in hematologic malignancies.[27-30] More generally, our data supports the finding that activating mutations of oncogenes are relatively infrequent in MDS. Our survey of over 900 mutations in 111 cancer-associated genes identified only 6 mutated oncogenes, present in fewer than 10% of patient samples.

Prognostically significant somatic mutations occurred in patients of all risk groups. Most patients with an EZH2 or ASXL1 mutations had low or intermediate-1 IPSS risk (86% and 73%, respectively). EZH2 mutations carried a high hazard ratio of death, 2.13 (95% CI 1.36-3.33), and were strongly associated with decreased OS in the stepwise, multivariable model (p<0.001) that included age, sex, IPSS risk group and the presence of other mutations. Mutations of ASXL1 carried an hazard ratio of 1.38 (95% CI1.00-1.89) but, as the second most commonly mutated gene identified in this study, contributed additional adverse risk to the greatest number of patients. Therefore, lower-risk MDS patients with EZH2 and ASXL1 mutations may require more aggressive treatment than would be predicted by the IPSS.

Figure 11A:
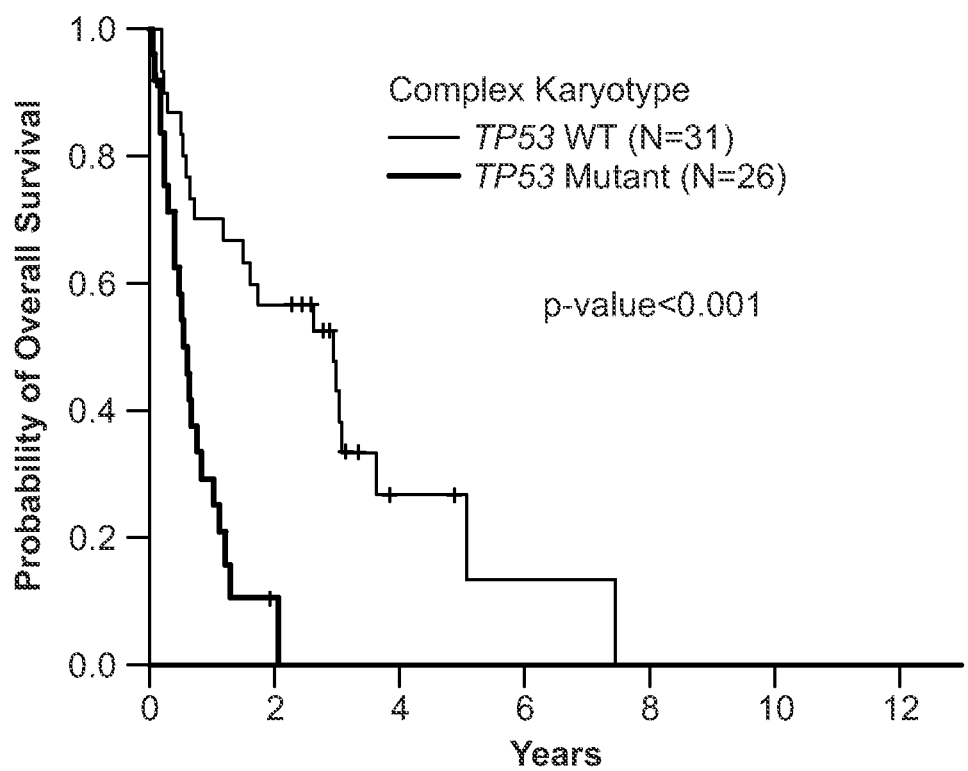
FIG. 11 shows the survival of patients with complex cytogenetics or higher risk IPSS groups stratified by TP53 mutation status. (A) Patients with complex cytogenetics and TP53 mutation have significantly shorter overall survival than patients with complex cytogenetics and no TP53 mutation. (B) Patients with increased IPSS risk and TP53 mutation have significantly shorter overall survival than patients with increased IPSS risk and no TP53 mutation.
Figure 11B:
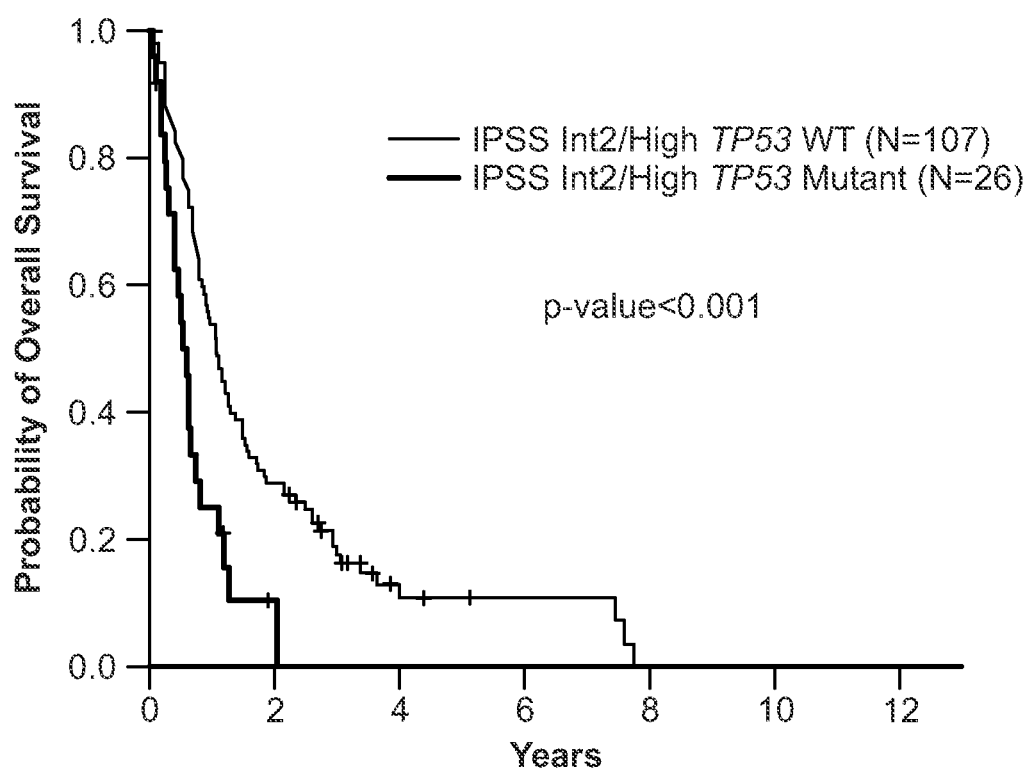

In contrast, TP53 mutations were mainly observed in patients with intermediate-2 and high IPSS risk (79%), and were strongly associated with thrombocytopenia, elevated blast proportion, and complex cytogenetics. Even though these measures are integrated into the IPSS, TP53 mutations remained strongly associated with shorter OS after adjusting for IPSS risk group (p<0.001), indicating that these mutations adversely impact survival through additional means (FIG. 11). Furthermore, patients with mutant TP53 and complex cytogenetics had a paucity of mutations in other genes, suggesting that this group could be considered a distinct molecular subclass of MDS with a unique pathogenic mechanism.

Figure 12A:
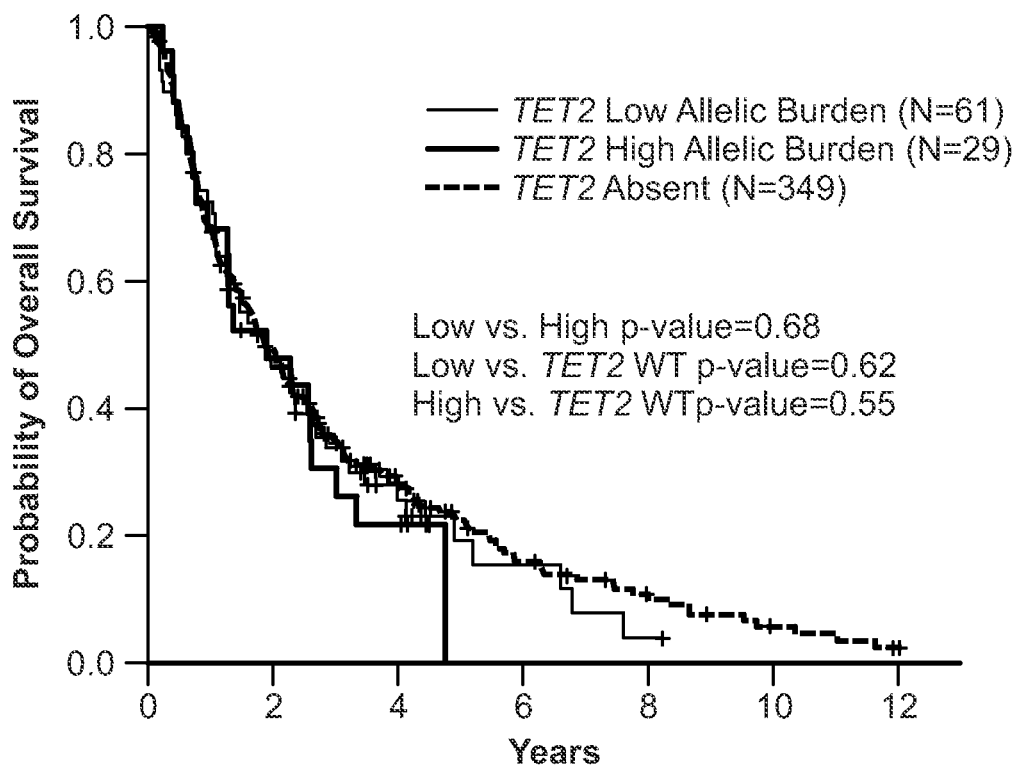
FIG. 12 shows the survival of patients with TET2 mutations stratified by mutant allele burden and prognostic risk. (A) The overall survival of patients with more than two TET2 mutations or a single TET2 mutation present at twice the frequency of the wild type allele (red line) is compared to the survival of patients with a single TET2 mutation and lower mutant allele burden (blue line) and to the survival of patients without a TET2 mutation (black line). The proportion of mutant alleles in each sample was determined by dividing the area of the mutant allele peak identified in hME by the sum of the areas of the mutant and wild type allele peaks. (B) The survival of patients in four groups are compared: Low or Int-1 IPSS risk group and TET2 mutation present (black line), Low or Int-1 IPSS risk group and no TET2 mutation (green line), Int-2 or High IPSS risk group and TET2 mutation present (red line), and Int-2 or High IPSS risk group and no TET2 mutation (blue line). Pairwise comparisons show no significant differences based on TET2 mutation status in either the lower or higher risk groups.
Figure 12B:
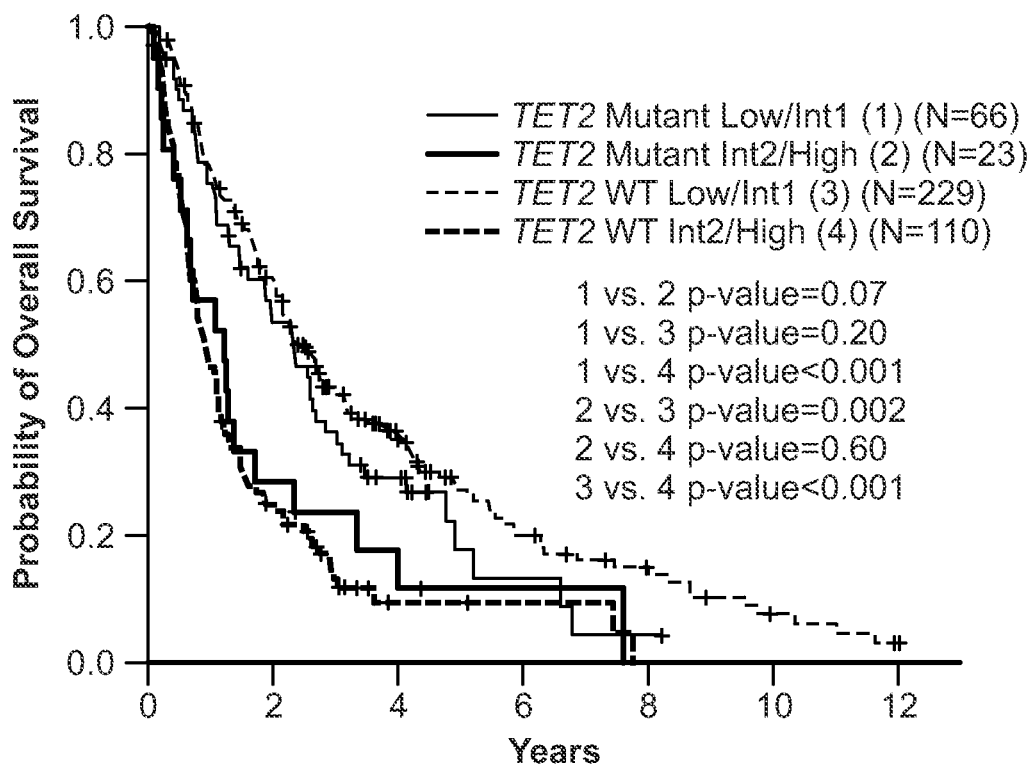
Figure 13A:
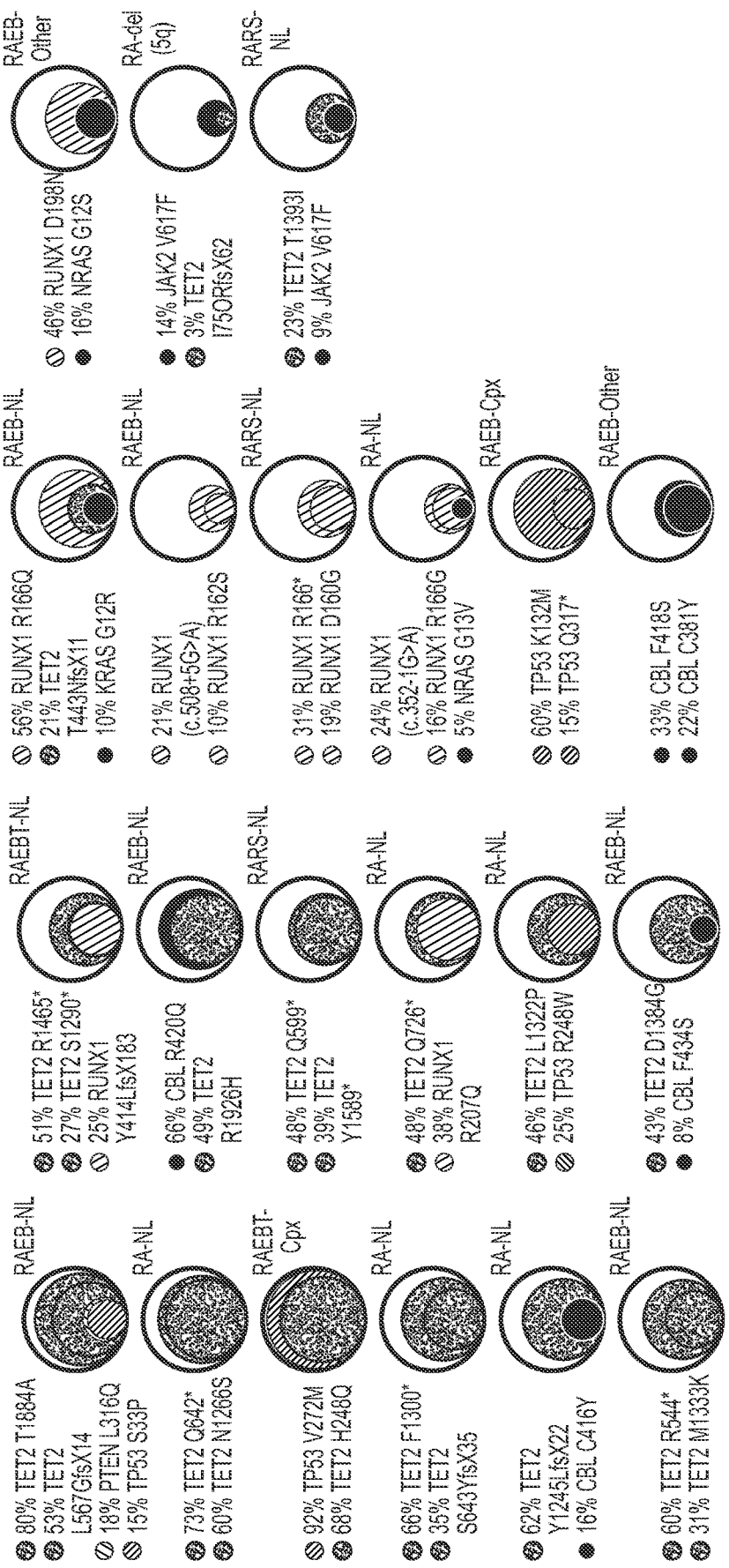
FIGS. 13A-13B show the mutant allele frequencies in individual samples. Mutant allele frequencies in individual samples with two or more mutated genes validated by quantitative mass spectroscopic genotyping are shown. This includes most co-mutated cases of TET2, RUNX1, TP53, CBL, PTEN, NRAS, KRAS, JAK2, and NPM1. The area of each colored circle indicates the allele frequency of the given mutation. The text box to the left of the circles lists the frequency and nature of each mutation in order of decreasing allele frequency. The FAB class and karyotype for each sample is shown to the right of the circles (NL=normal karyotype, Cpx=complex, +8=Trisomy 8, Other=other abnormalities not explicitly included in the IPSS). No mutated gene is consistently present with the greatest allele frequency.
Figure 13B:
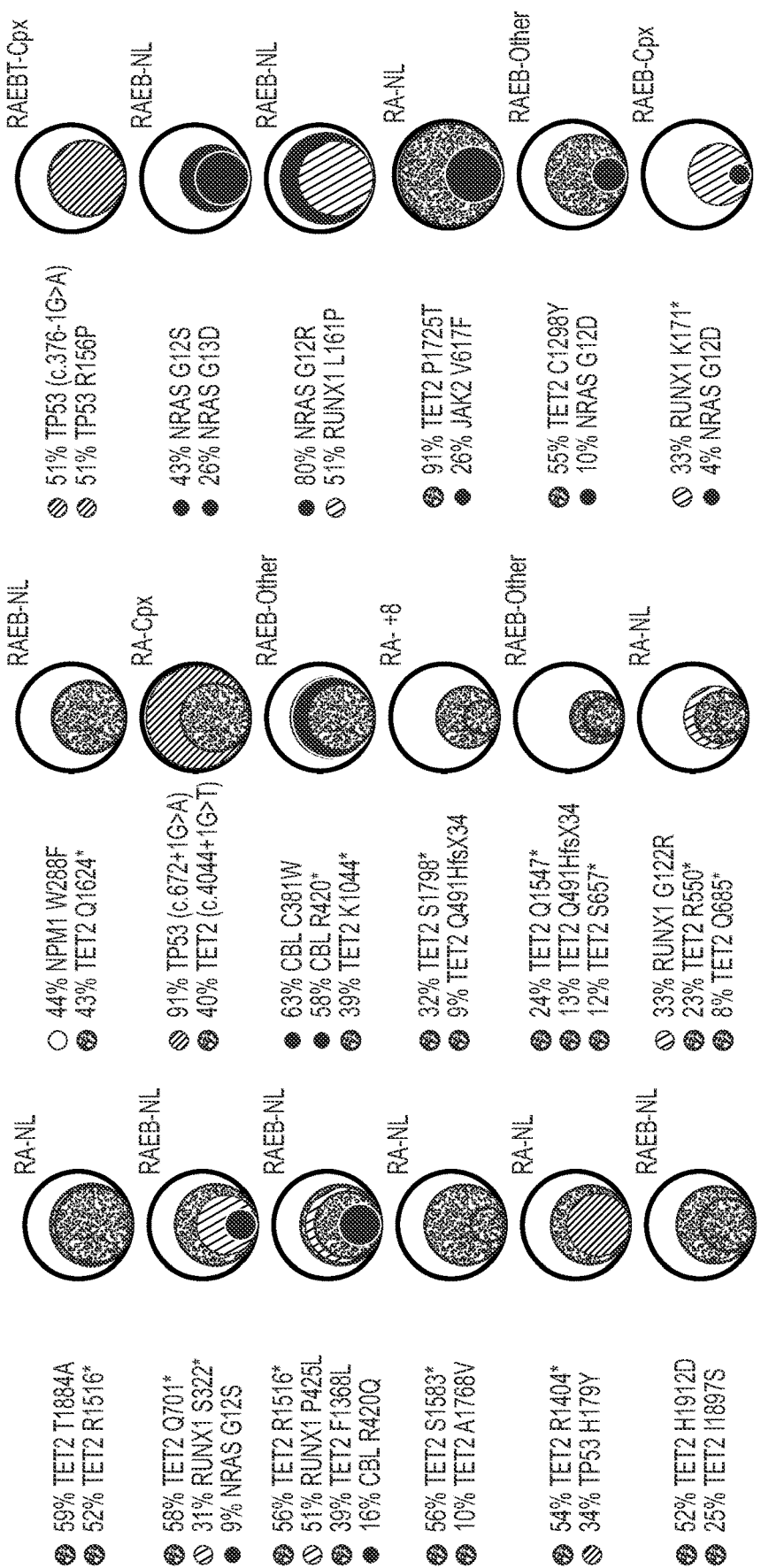

TET2 mutations were the most prevalent genetic abnormality identified in our sample set. These mutations were not strongly associated with clinical measures such as cytopenias and blast proportion, consistent with the finding that TET2 mutations occur in diverse myeloid malignancies including myeloproliferative neoplasms that are not characterized by defects in hematopoietic differentiation. Over one quarter (25.6%) of samples with TET2 mutations had two distinct mutations in this gene, suggesting that biallelic loss of wild type TET2 contributes to MDS pathogenesis in a subset of cases. In contrast to previous reports with smaller sample sets, neither monoallelic nor biallelic mutations were associated with IPSS risk or OS (FIG. 12).[11,31] Furthermore, analysis of mutant allele burden in samples with mutations of TET2 and other genes show that TET2 mutations are not always present at the greatest frequency which would be expected if they were exclusively early pathogenic events (FIG. 13). TET2 mutations were not exclusive of abnormalities in other epigenetic regulators such as ASXL1 and EZH2. 32-34 Mutations in these genes had different associations with clinical phenotypes, including OS, suggesting that these chromatin modifying genes drive distinct and additive aspects of cellular transformation to MDS. Each of the prognostically significant mutations likely alters the biology and phenotype of MDS in unique ways, as is the case for cytogenetic abnormalities, with complex interactions between combinations of genetic and epigenetic lesions. Nevertheless, a simplified prognostic scoring scheme has great clinical utility. One approach would be to include one additional variable into the IPSS, in which mutation in any of the genes with independent prognostic significance increases the score to the next risk level.

As we demonstrate here, somatic mutations in several genes are associated with distinct effects on cytopenias, blast proportion, the likelihood of co-occurrence with other molecular lesions, and OS. Clinically, it will soon be possible to detect a broad range of point mutations in peripheral blood with sensitive genotyping methods, which will not only improve prognostication in MDS, but facilitate the diagnosis of these disorders, evaluation of disease progression, and monitoring of response to treatment. The integration of mutation assessment into diagnostic classification and prognostic scoring systems has the potential to parse diverse MDS into a set of discrete diseases with more consistent clinical phenotypes, prognosis, and responses to therapy.

Example 3: Validation of the LR-PSS

Figure 14A:
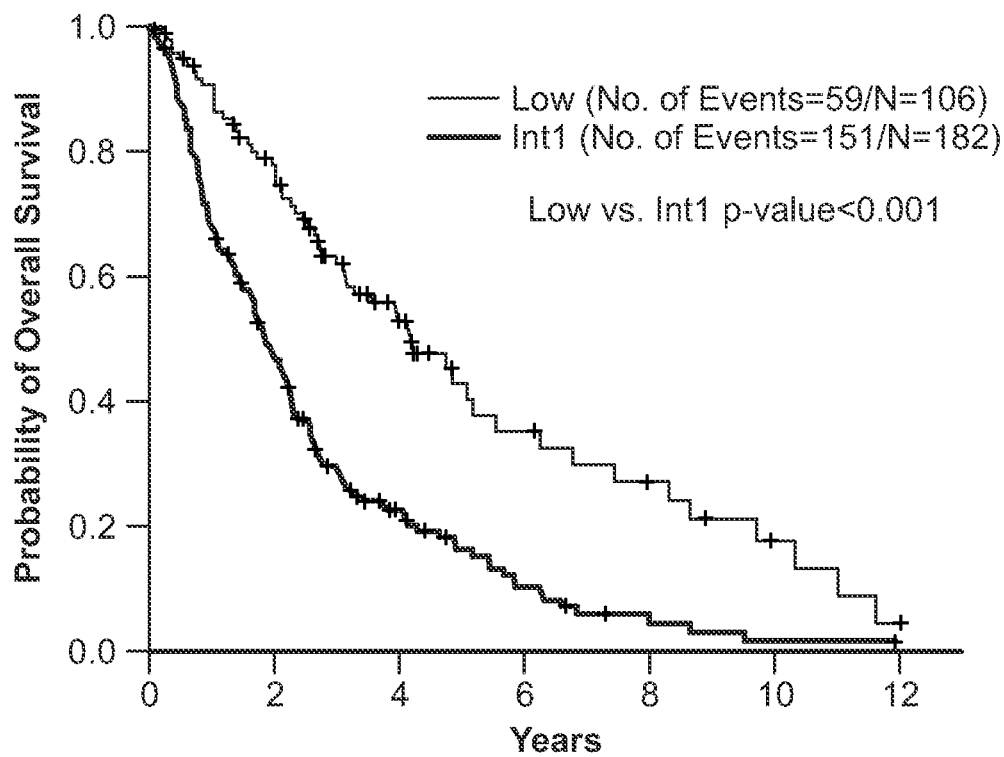
FIG. 14 shows the validation of the LR-PSS in a well-annotated cohort of 288 patients with Low or Intermediate-1 IPSS risk MDS and clinical characteristics representative of lower risk MDS patients described in epidemiologic studies. A) Kaplan-Meier survival curves for 288 patients with Low and Intermediate-1 IPSS Risk. B) Kaplan-Meier survival curves for the same patients assigned to Categories 1-3 by the LR-PSS. Overall survival was calculated from the time of sample collection to the time of death from any cause.
Figure 14B:
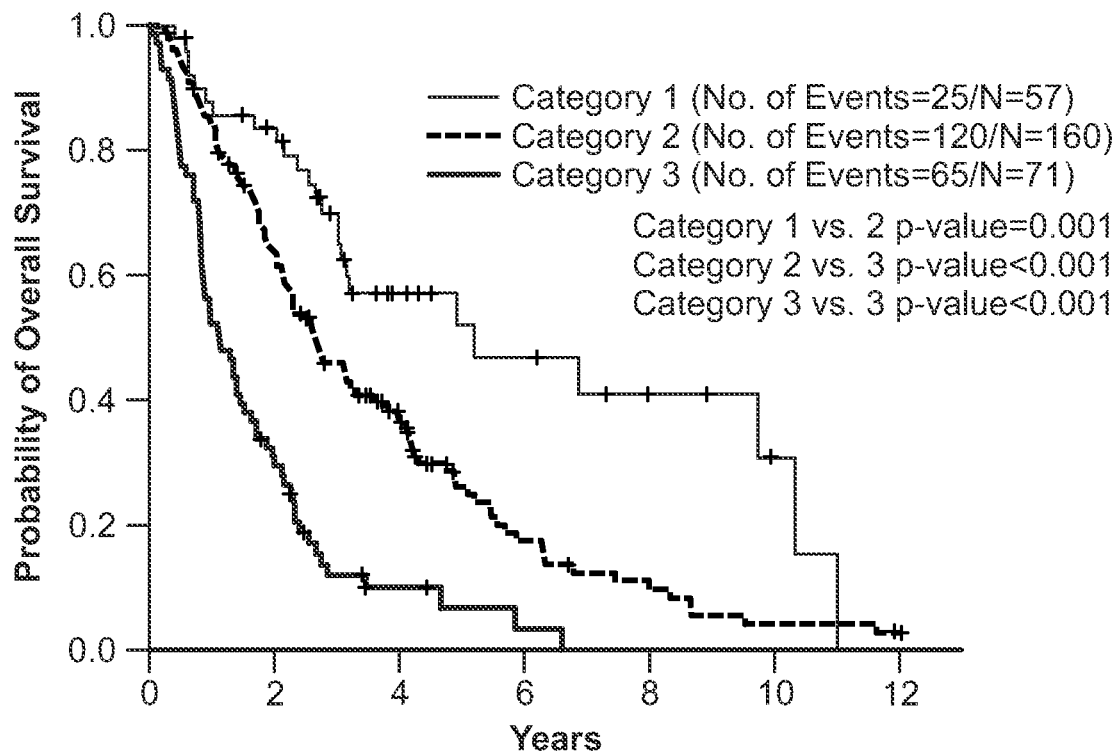

We first evaluated clinical parameters that might improve the prediction of prognosis in MDS patients with lower risk disease, as determined by the IPSS score. The LR-PSS was developed for this purpose in a cohort of 856 patients, but it has not been validated in an independent cohort of patients. We applied the LR-PSS to a well-annotated cohort of 288 patients with Low or Intermediate-1 IPSS risk MDS and clinical characteristics representative of lower risk MDS patients described in epidemiologic studies (Table 8). When the LR-PSS was applied to this cohort, 57 patients (19.8%) were assigned to risk Category 1, with a median survival of 5.19 years (95% confidence interval [CI], 3.01-10.34); 160 patients (55.6%) were assigned to Category 2, with a median survival of 2.65 years (CI, 2.18-3.30); and 71 (24.7%) were assigned to Category 3, with a median survival of 1.11 years (CI, 0.82-1.51, FIG. 14, Table 11).

The differences in overall survival between LR-PSS categories for patients in our cohort was highly significant (p≤0.001 for each comparison), and comparable to those in the original description of the LR-PSS (6.7, 2.3, and 1.2 years in Categories 1-3 respectively). The outcome for patients assigned to Category 3 is similar to the published median survival of patients with Intermediate-2 IPSS risk, indicating that these patients should be considered for therapies commonly reserved for higher risk MDS. These findings validate the LR-PSS in an independent cohort of patients.

Example 4

Genetic Characterization of Lower IPSS Risk MDS

Mutations of individual genes can provide prognostic information that is independent of the IPSS score in MDS patients generally, but the prognostic significance of mutations has not been examined specifically in patients with lower risk MDS. Bone marrow aspirates from the 288 patients in our cohort were previously examined for mutations in 18 genes, including TET2, ASXL1, TP53, RUNX1, EZH2, ETV6, and NRAS. Following recent reports of mutations in DNMT3A, SF3B1, SRSF2, and U2AF1 in MDS, we sequenced the recurrently mutated regions of these genes in all samples.

Figure 15:
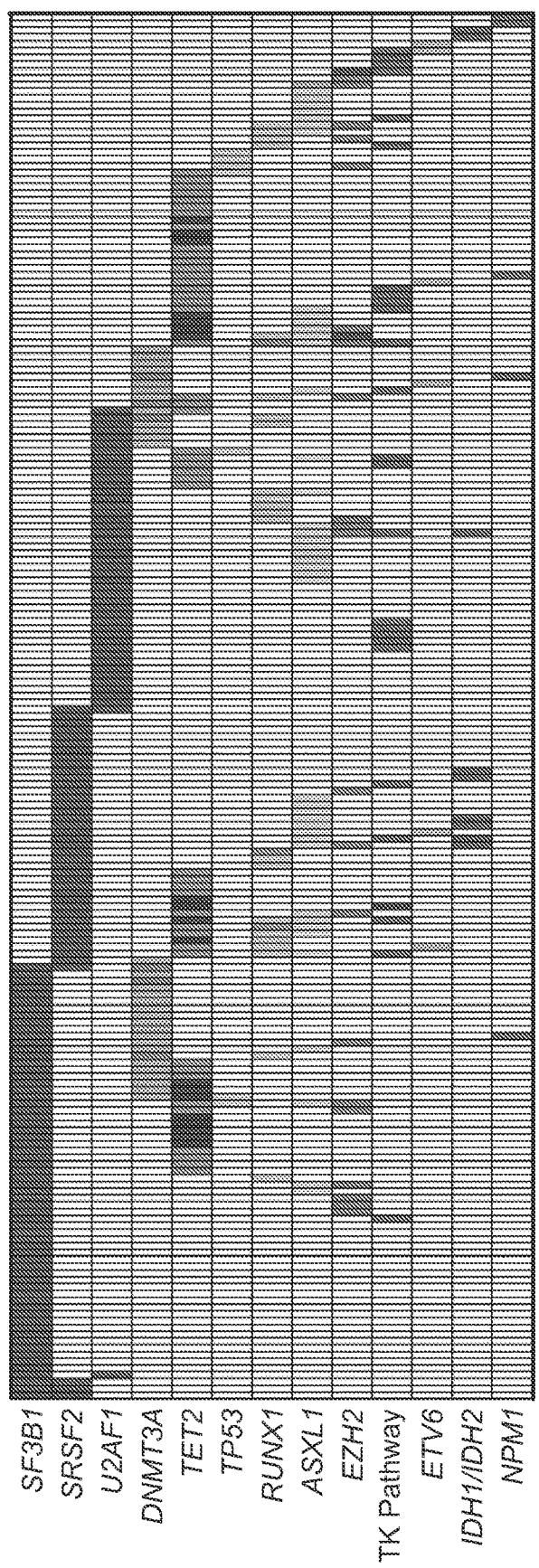
FIG. 15 shows the distribution of mutations in 204 out of 288 lower risk MDS samples with one or more mutations. Each column represents an individual sample. Colored cells indicate a mutation in the gene(s) described in that row on the left. Darker bars indicate 2 or more distinct mutations. Tyrosine kinase (TK) pathway genes include NRAS, KRAS, BRAF, CBL, and JAK2.

The most commonly mutated genes in lower risk MDS were TET2 (23% of samples), SF3B1 (22%), U2AF1 (16%), ASXL1 (15%), SRSF2 (15%), and DNMT3A (13%). In aggregate, we identified mutations in 204 out of 288 lower risk MDS patient samples (71% of the cohort), including 70% of cases with a normal karyotype. The distribution and co-occurrence of mutations is shown in FIG. 15

Example 5: DNMT3A and SF3B1 Mutations Commonly Co-Occur

Mutations in DNMT3A and SF3B1 were not exclusive of mutations in any of the other frequently mutated genes, but co-occurred with each other significantly more often than predicted by chance (p<0.001), suggesting a previously unappreciated molecular synergy between these two genetic lesions. Specifically, of the 36 patients with a DNMT3A mutation, 20 (56%) also had a mutation in SF3B1. As previously reported, mutations of SF3B1 were highly enriched in samples from patients with refractory anemia with ring sideroblasts (RARS), present in 78% of cases vs. 13% of non-RARS cases (p<0.001).

Example 6: Mutated Genes Associated with Prognostic Features

Mutations may alter clinical parameters in a manner that is accurately captured by the LR-PSS. Alternatively, some mutations may yield orthogonal information about the MDS phenotype that is not well captured by standard clinical variables. To address these possibilities, we examined the association of mutations with the clinical parameters included in the LR-PSS. Advanced age was associated with the presence of one or more mutations (48%<60 years vs. 77%≥60 years, p=<0.001), but no individual gene mutation was significantly associated with age. Mutations of ASXL1, RUNX1, and EZH2 were associated with a hemoglobin level less than 10 gm/dL (p≤0.008 for each comparison). A bone marrow blast count of 4% or greater was associated with mutations in SRSF2, ASXL1, RUNX1, NRAS, and CBL (p<0.005 for each comparison) while mutations in U2AF1, ASXL1, RUNX1, and NRAS were associated with a platelet count of <50×10$^9$/L (p<0.01 for each comparison). In contrast, SF3B1 mutation was associated with a normal or elevated platelet count (4% with <50×10$^9$/L vs. 15% with 50-200×10$^9$/L vs. 51% with >200×10$^9$/L, p<0.001).

Figure 16D:
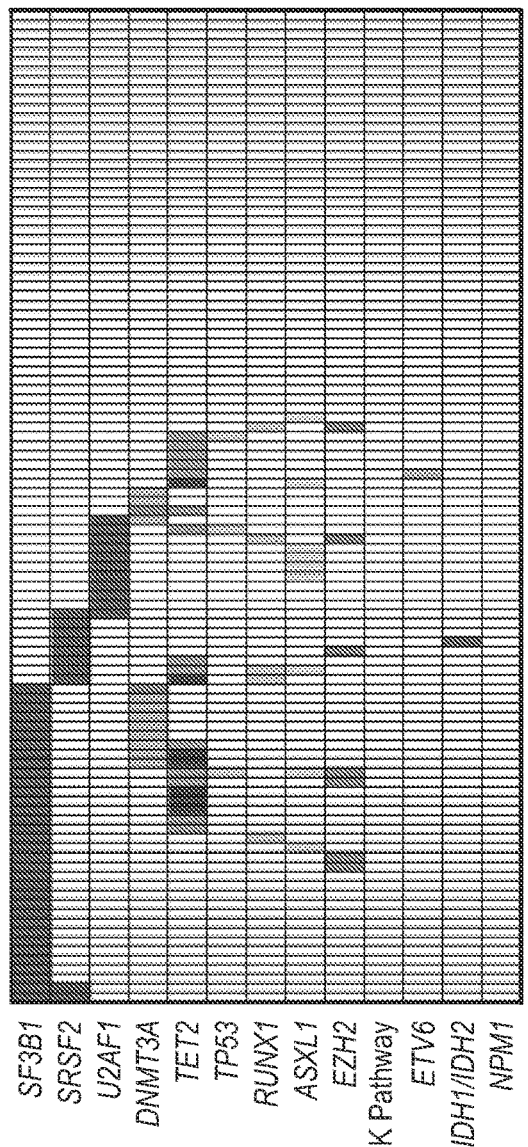
FIG. 16 shows the distribution of mutations in each LR-PSS risk category. A) Category 1—46% of samples have one or more mutations. B) Category 2—72% of samples have one or more mutations. C) Category 3—90% of samples have one or more mutations. D) IPSS Low risk patients—59% of samples have one or more mutations. E) IPSS Intermediate—1 risk patients—77% of samples have one or more mutations. Tyrosine Kinase (TK) pathway genes include NRAS, KRAS, BRAF, CBL, and JAK2.
Figure 16E:
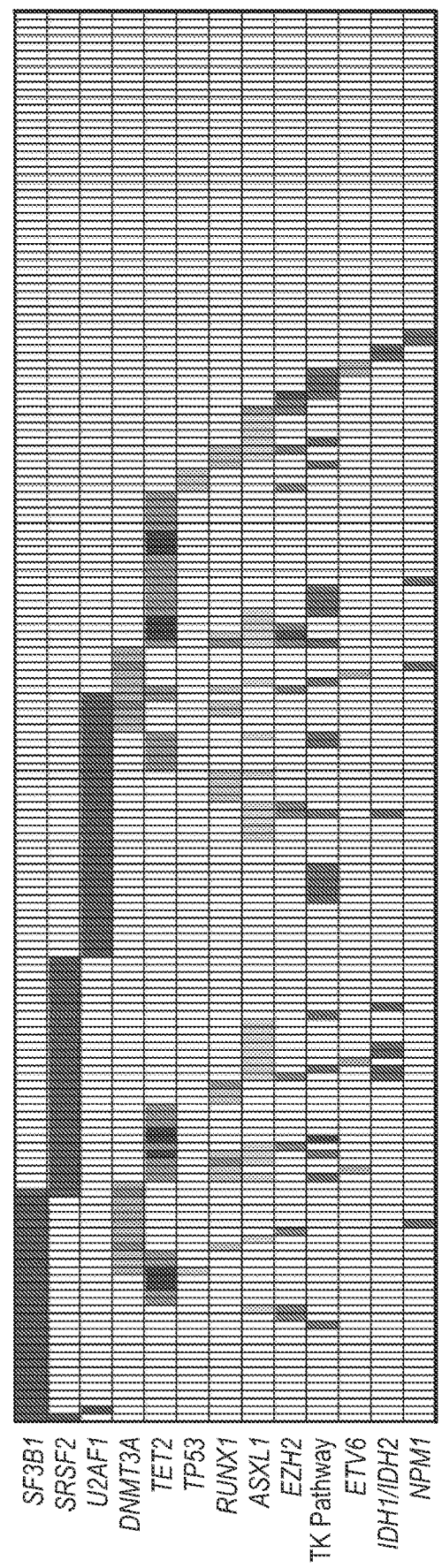
Figure 17A:
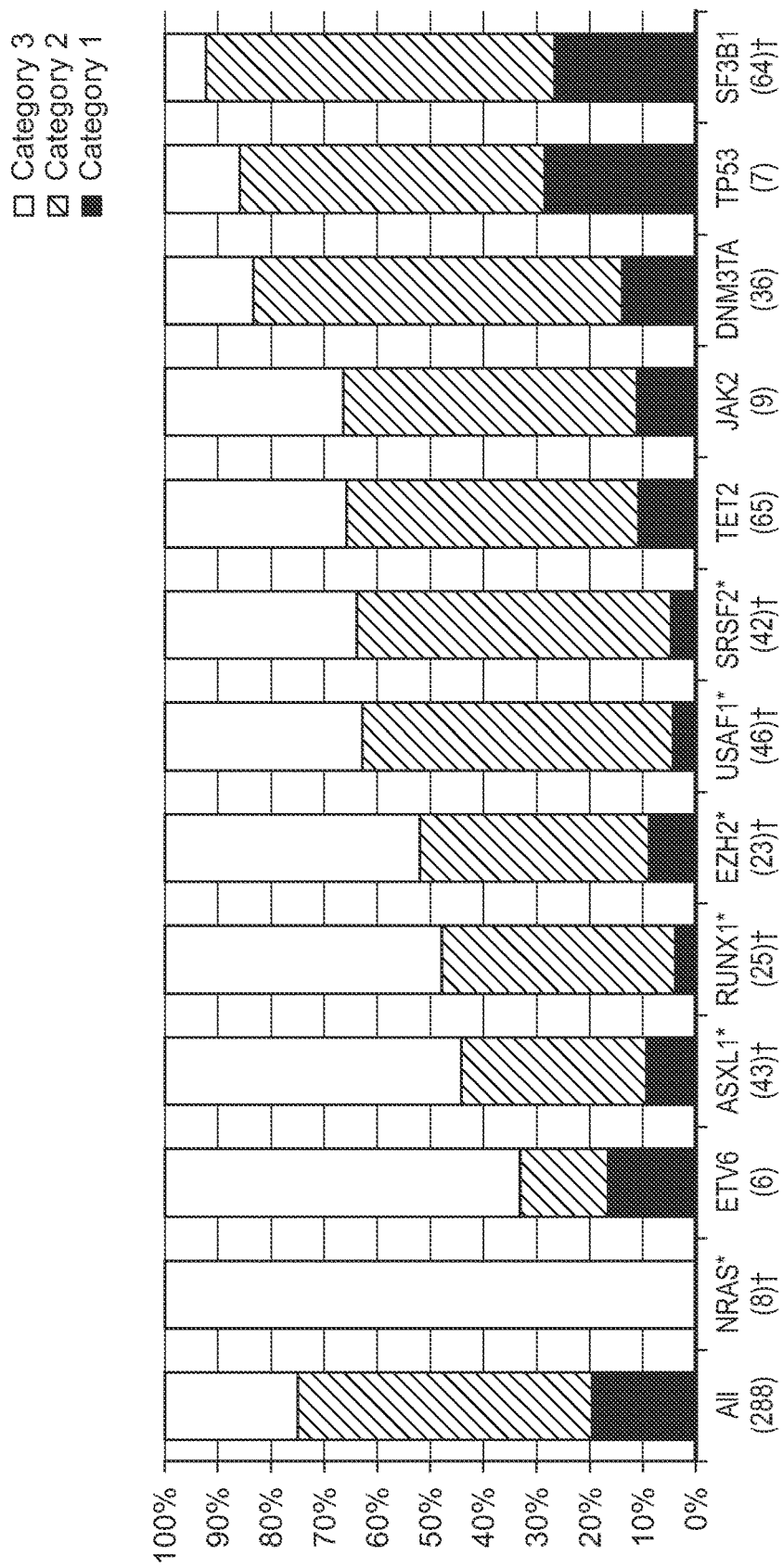
FIG. 17 shows the distribution of mutated genes in the A) LR-PSS and B) IPSS Risk Groups. (n)—Number of samples with a given mutation; *—Mutated genes that are univariately associated with a poor prognosis (p<0.05); †—Mutated genes with a risk group distribution significantly different from unmutated cases (p<0.01)
Figure 17B:
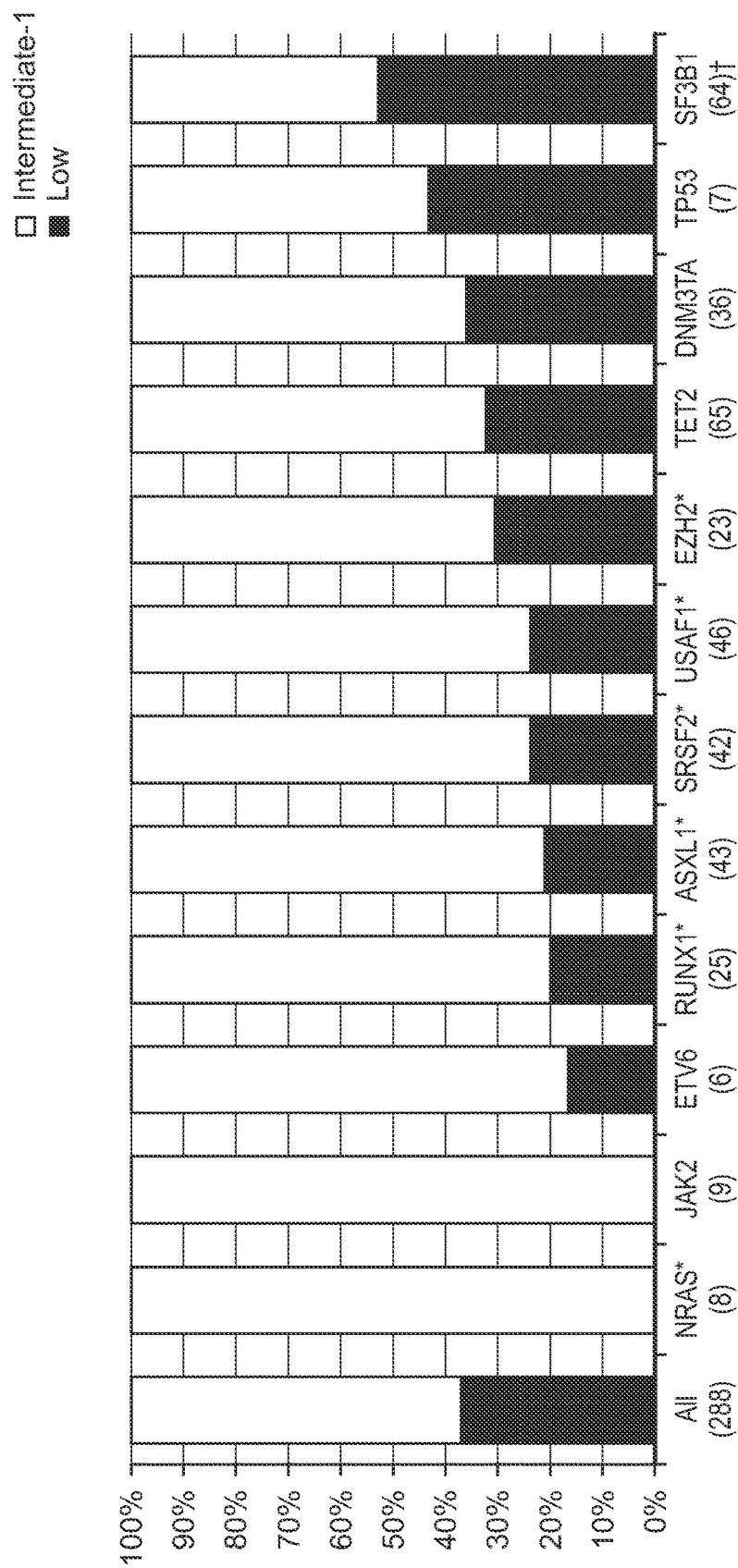
Figure 18A:
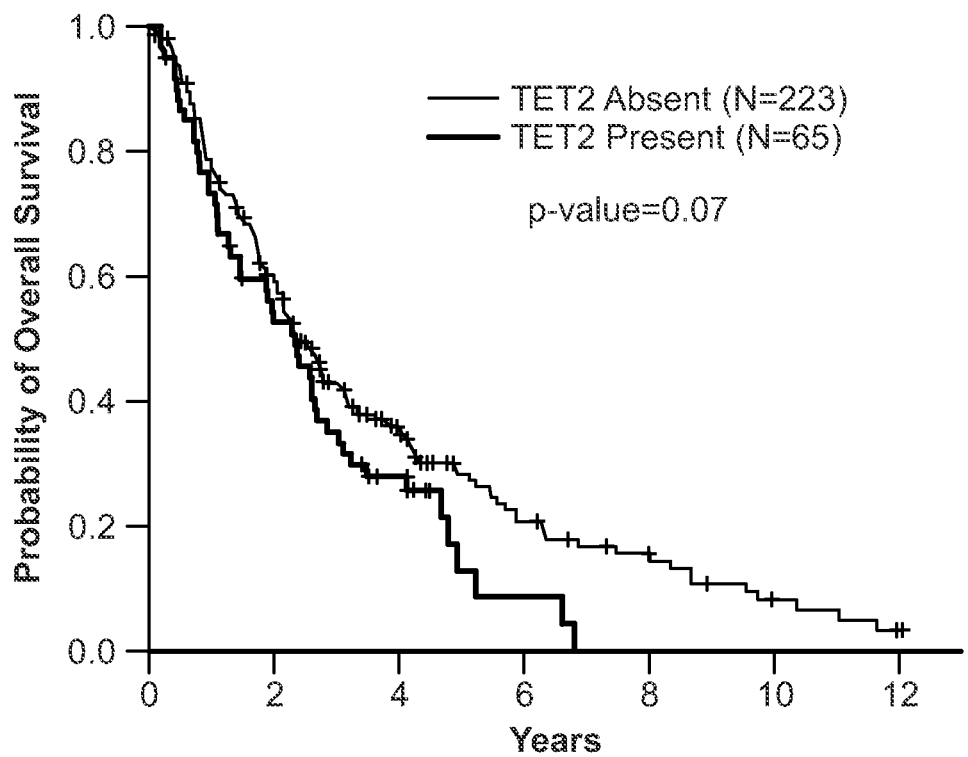
FIG. 18 shows the Kaplan-Meier overall survival curves for MDS patients with and without mutations in the 13 most frequently mutated genes: A) TET2 mutations; B) SF3B1 mutations; C) SRSF2 mutations; D) U2AF1 mutations; E) ASXL1 mutations; F) DNMT3A mutations; G) RUNX1 mutations; H) EZH2 mutations; I) JAK2 mutations; J) NRAS mutations; K) TP53 mutations; L) ETV6 mutations; M) CBL mutations; N) NPM1 mutations; O) IDH1 mutations.
Figure 18B:
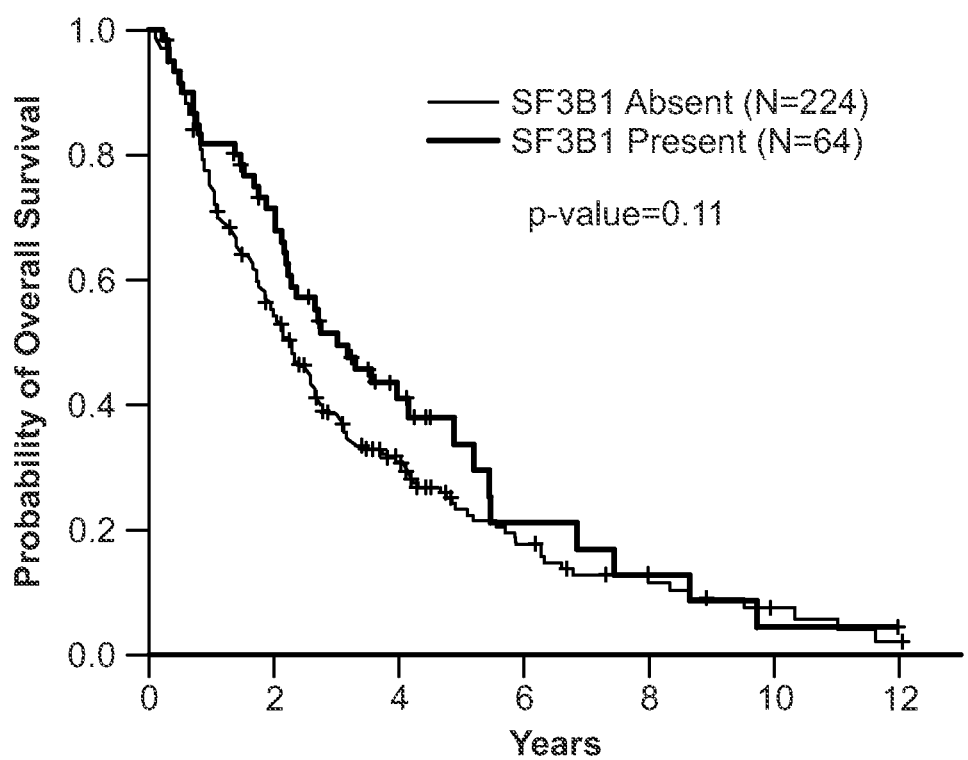
Figure 18C:
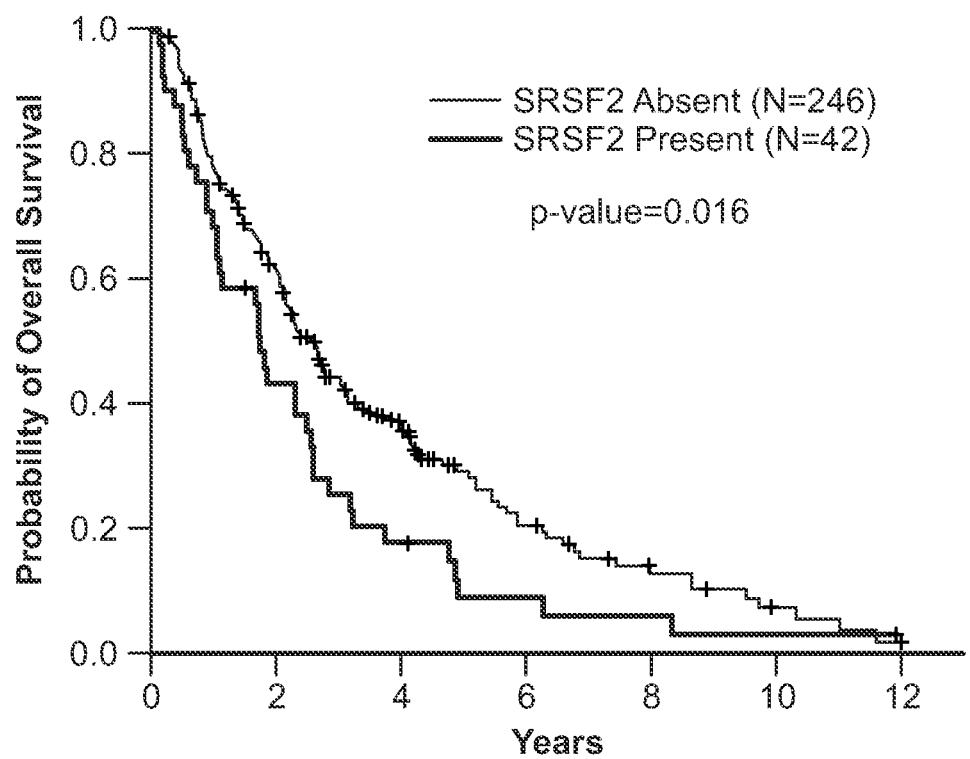
Figure 18D:
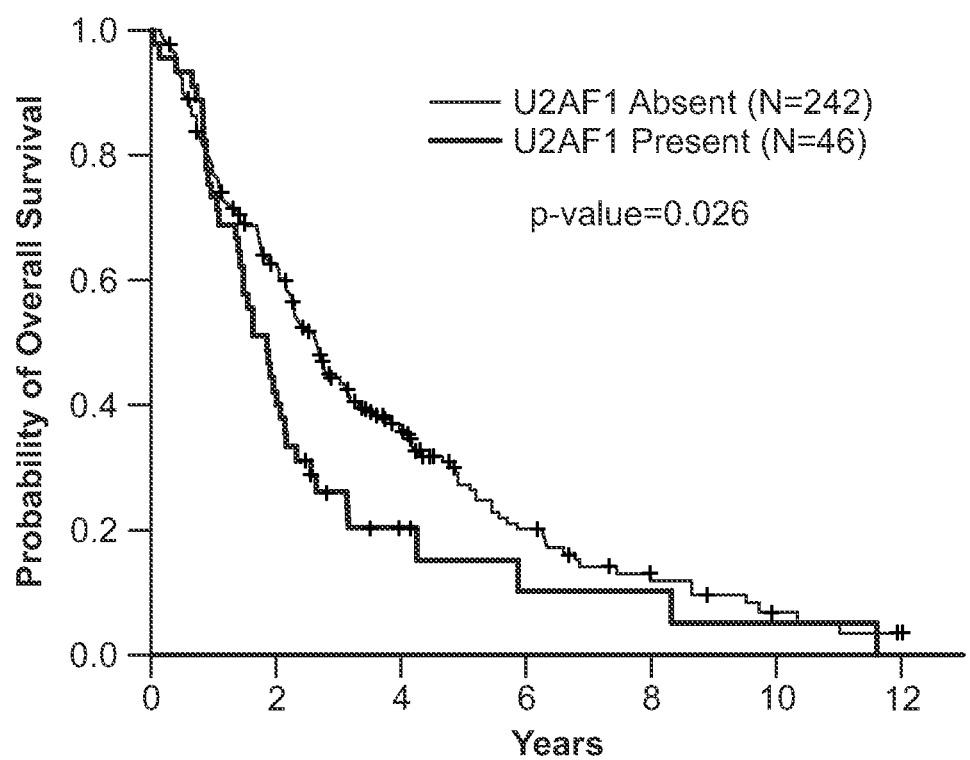
Figure 18E:
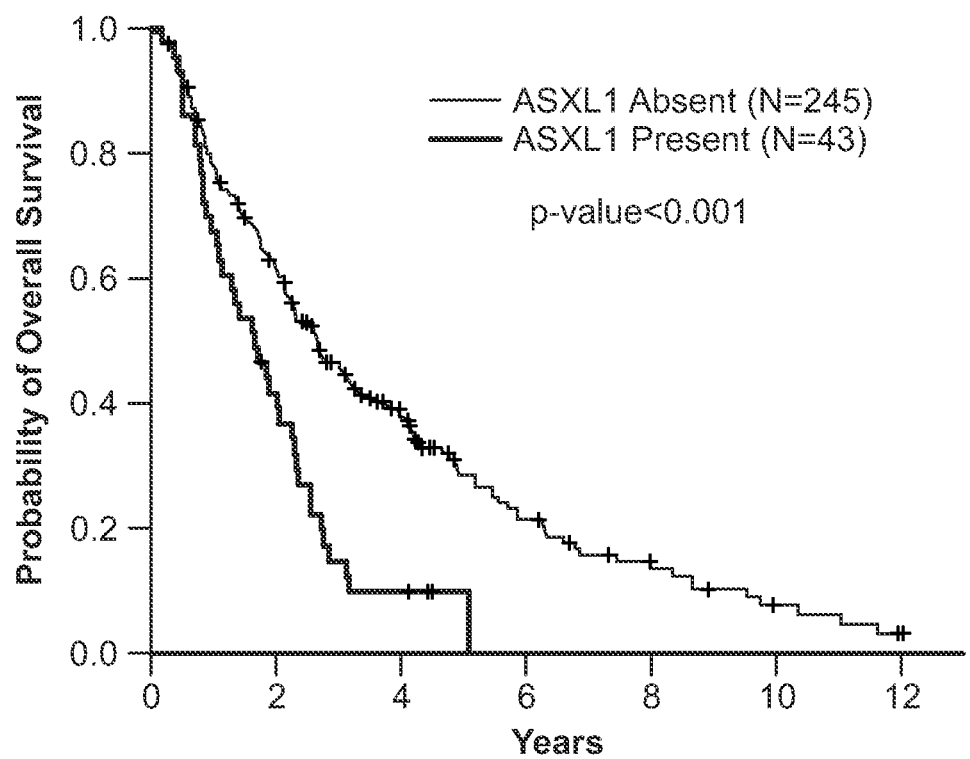
Figure 18F:
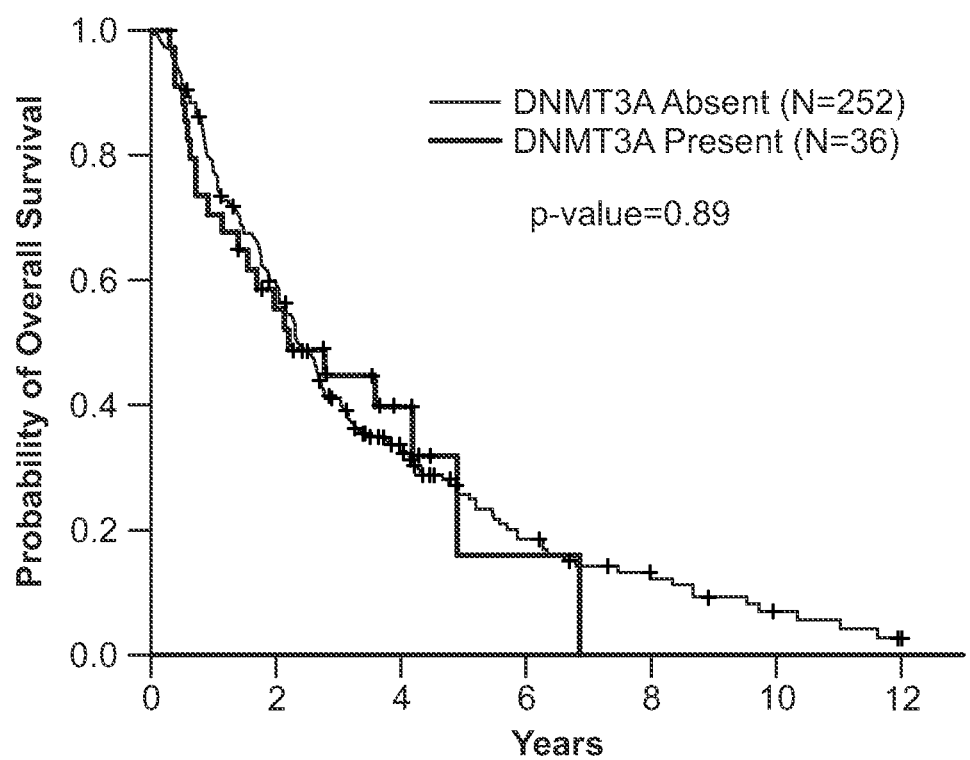
Figure 18G:
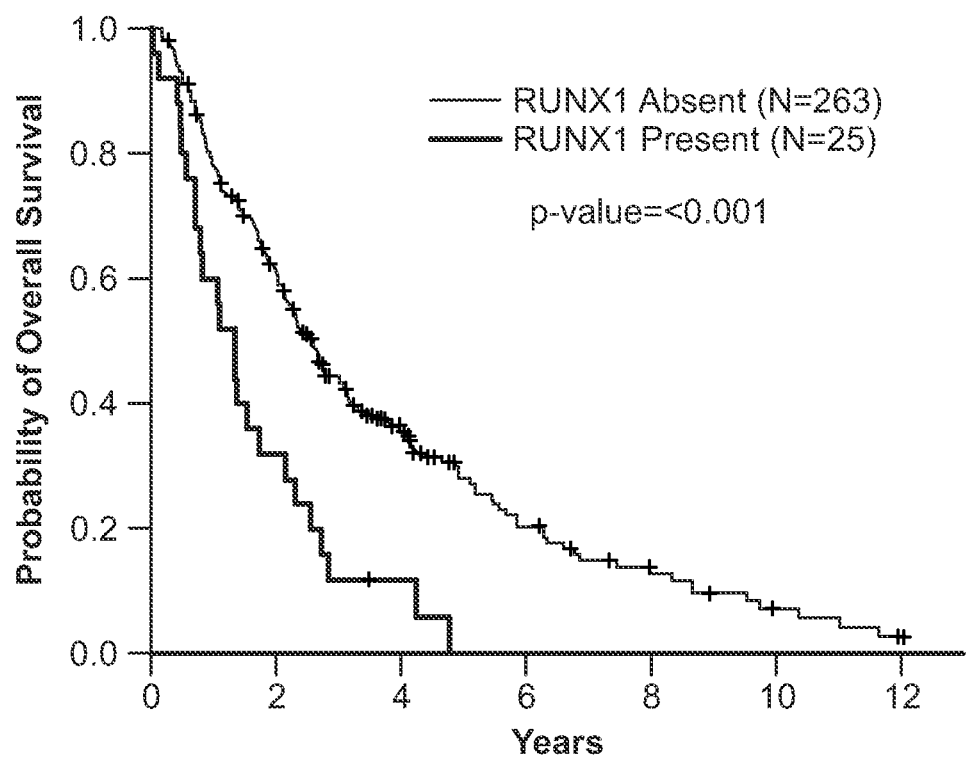
Figure 18H:
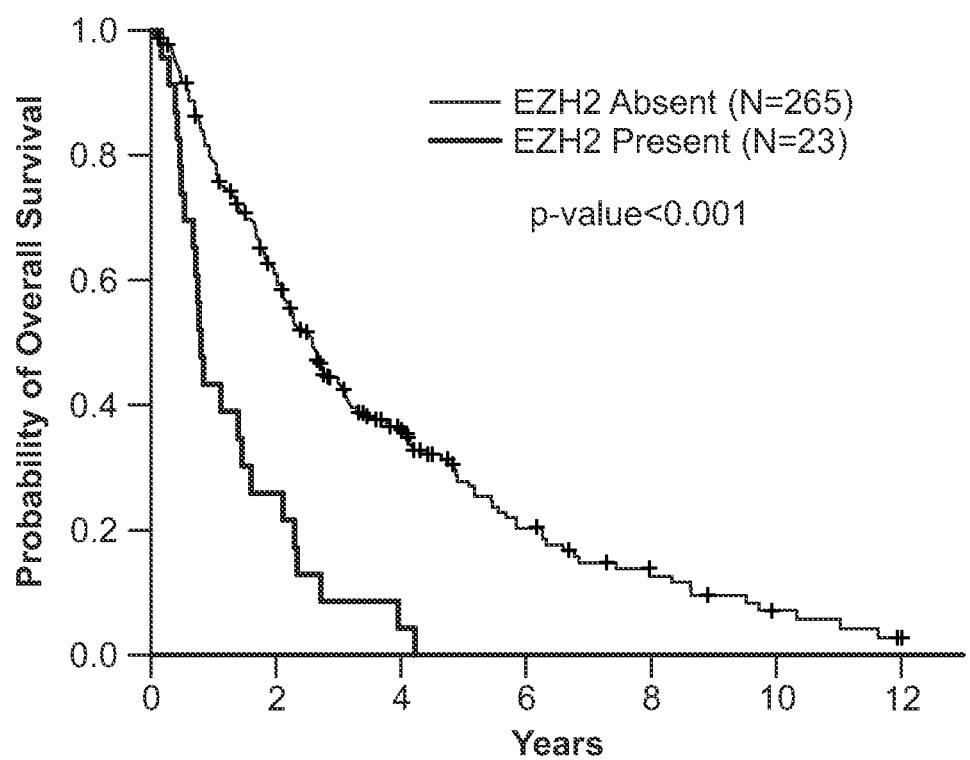
Figure 18I:
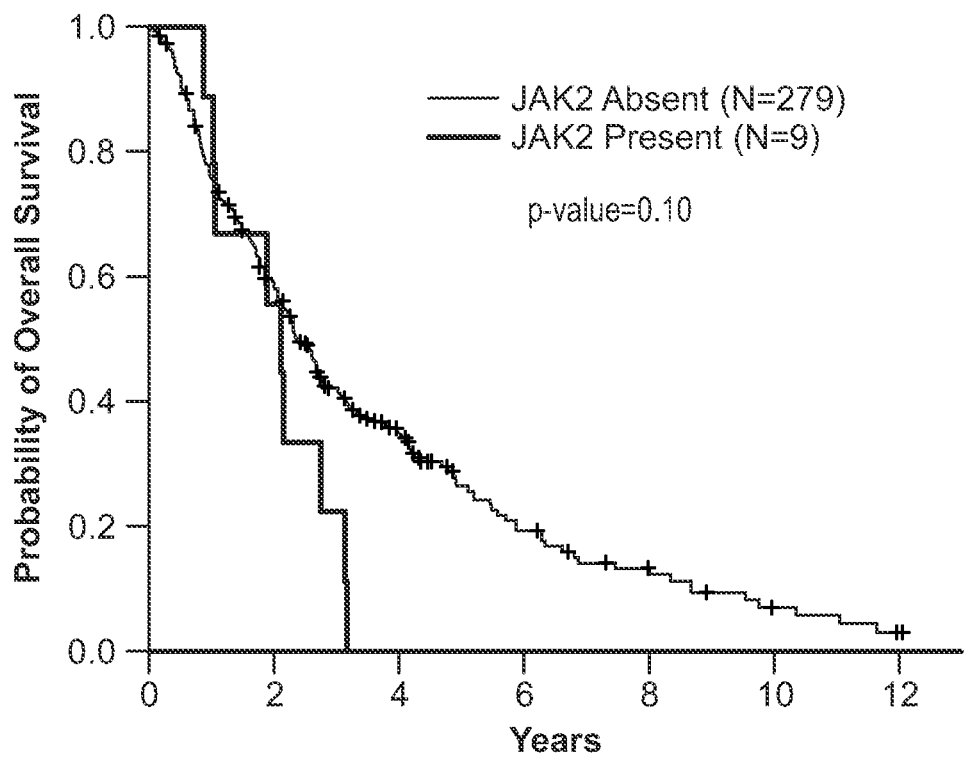
Figure 18J:
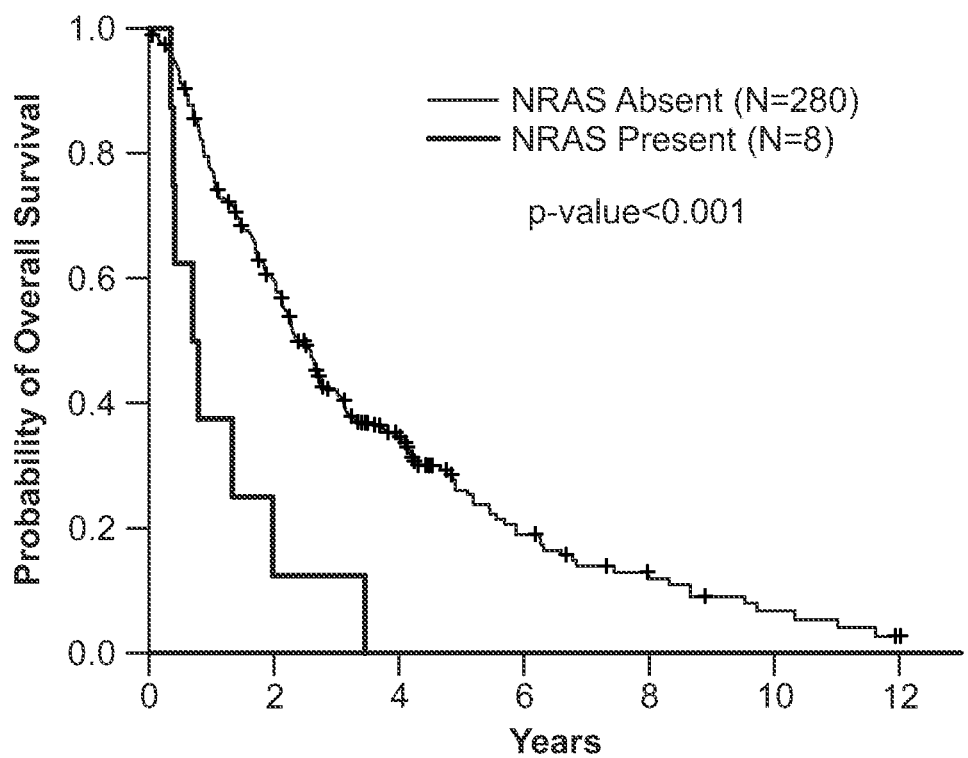
Figure 18K:
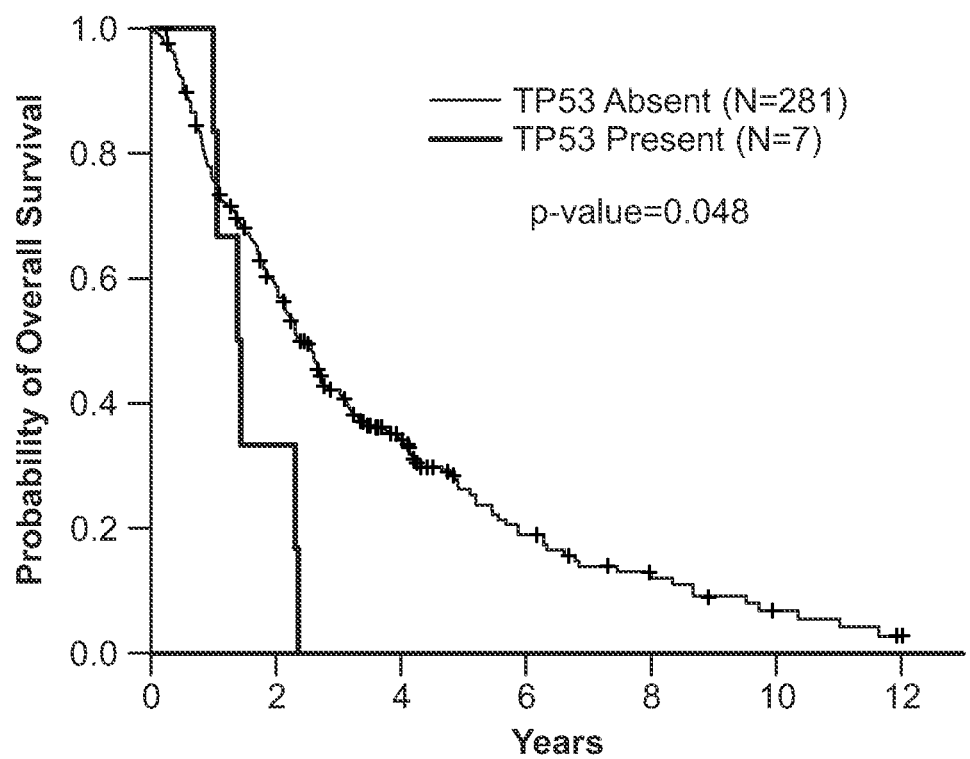
Figure 18L:
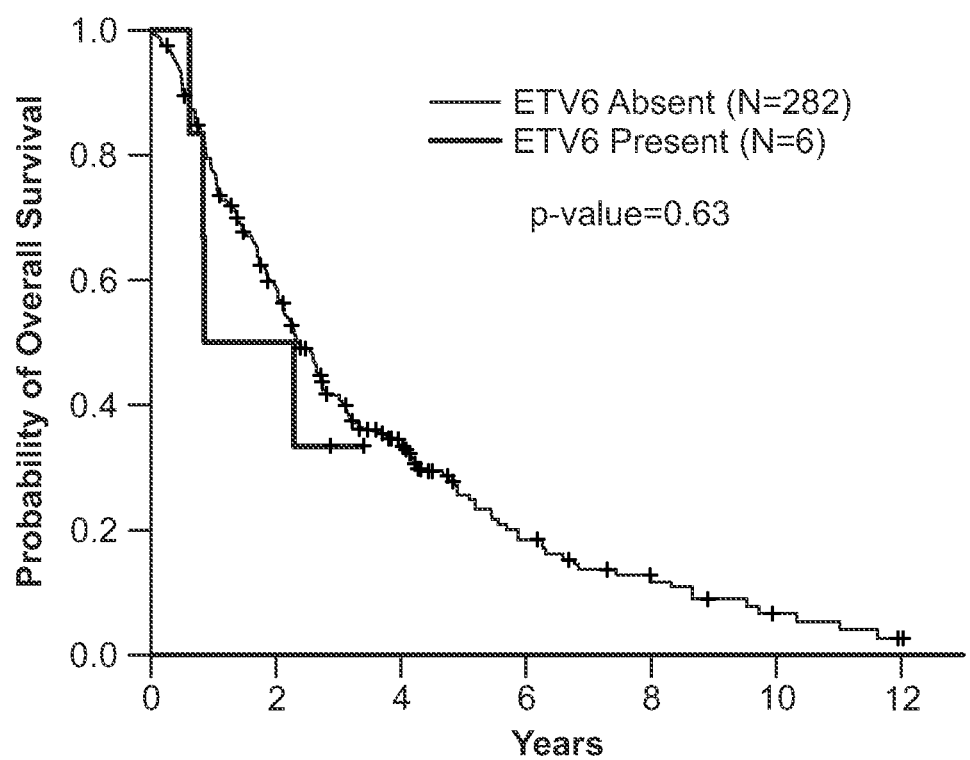
Figure 18M:
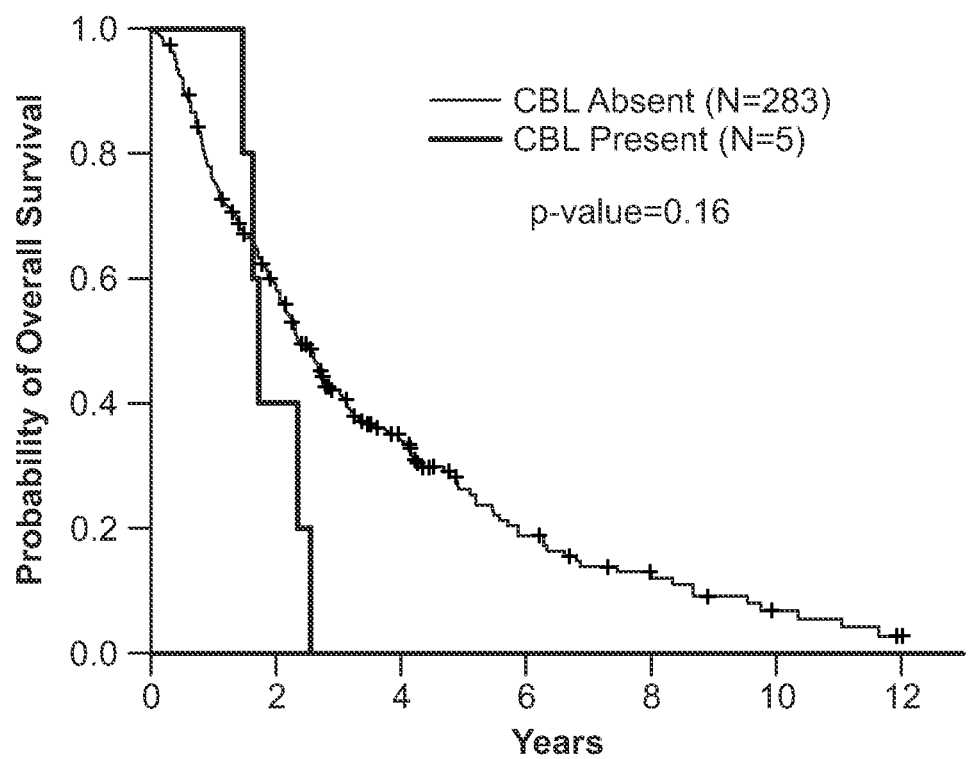
Figure 18N:
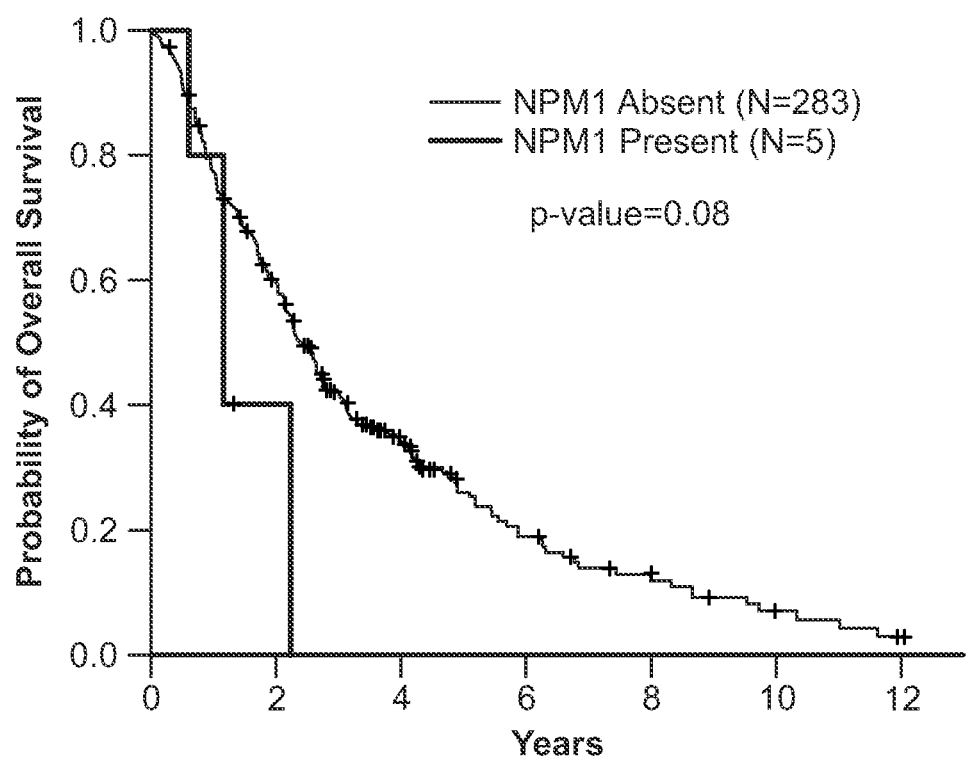
Figure 18O:
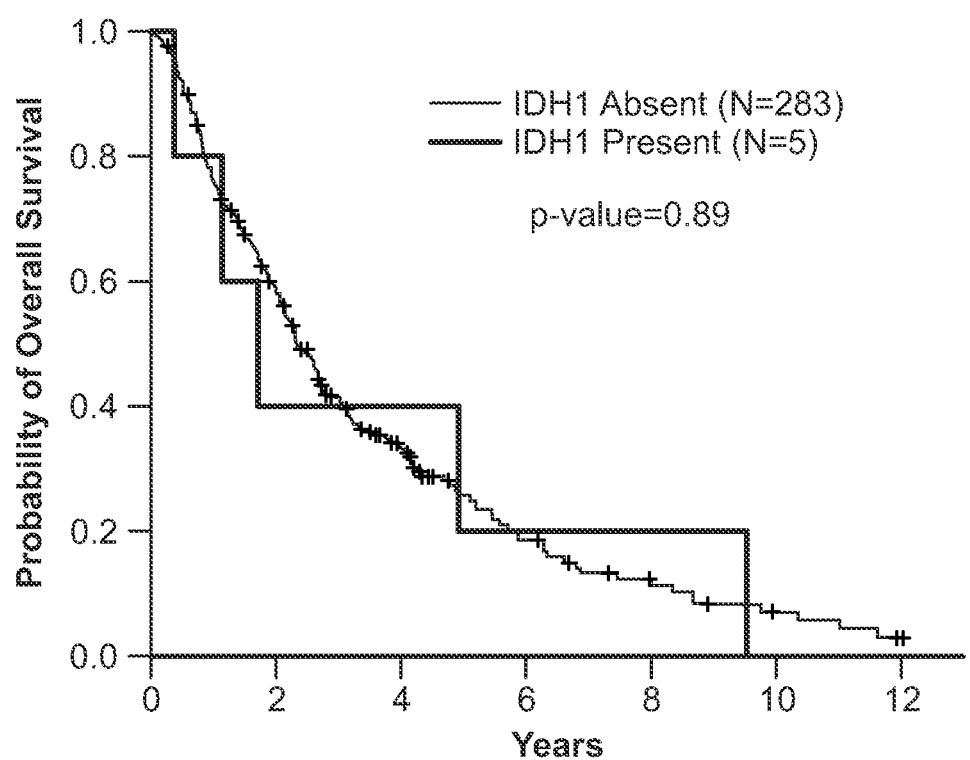

These findings demonstrate that mutations are significantly associated with specific parameters that are employed to calculate the LR-PSS. We therefore examined whether the mutations associated with higher risk features are disproportionately represented in the higher risk LR-PSS categories. Indeed, patients with mutations in ASXL1, U2AF1, SRSF2, RUNX1, NRAS, and CBL were overrepresented in the highest risk LR-PSS Category (p<0.005 for each comparison, FIGS. 16-17). In contrast, patients with SF3B1 mutations, which were not associated with prognostically adverse clinical measures, were significantly underrepresented in Category 3 (p<0.001). These findings demonstrate the association of mutations with prognostic clinical variables and suggest that the LR-PSS may more accurately capture biology driven by particular mutations.

Example 7: Mutated Genes Associated with Differences in Overall Survival

Figure 19A:
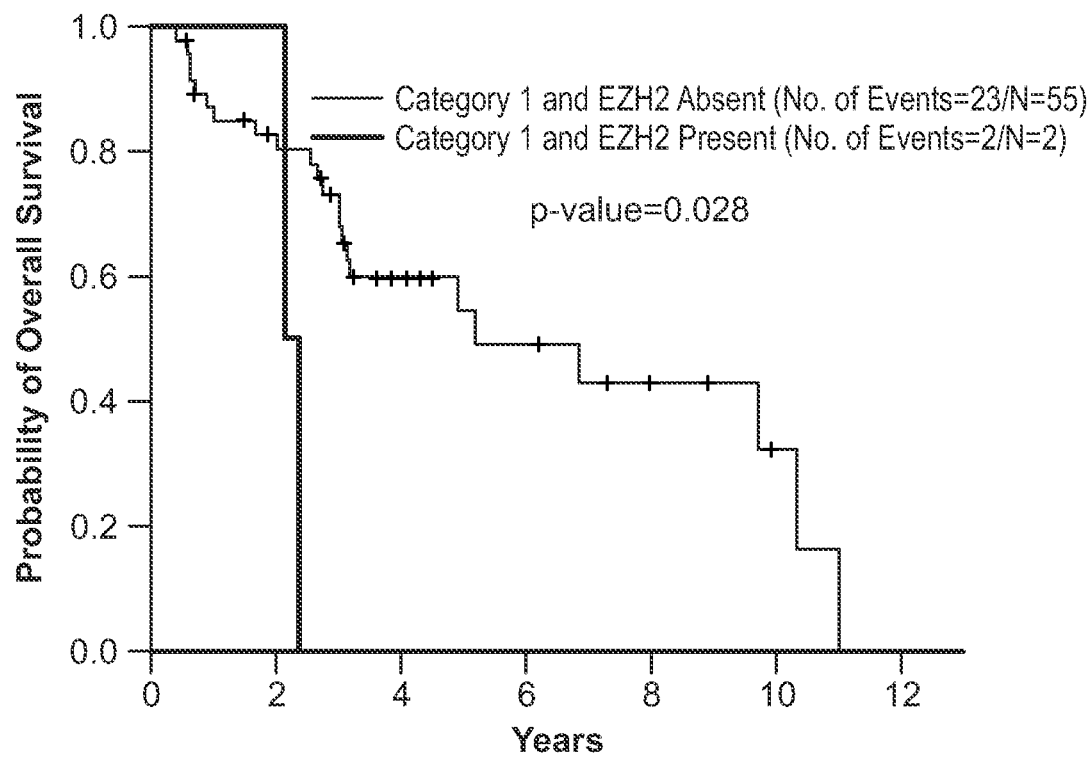
FIG. 19 shows the Kaplan-Meier overall survival curves for MDS patients in each LR-PSS risk category stratified by EZH2 mutation status. A) Category 1 patients. B) Category 2 patients. C) Category 3 patients.
Figure 19B:
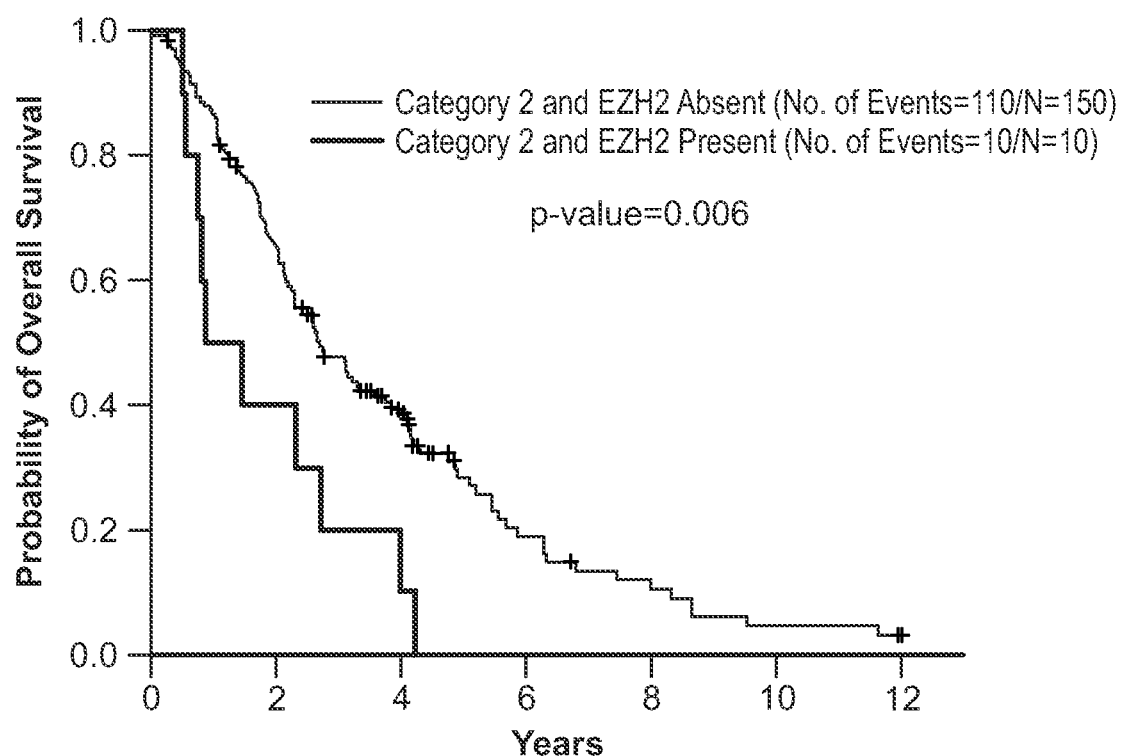
Figure 19C:
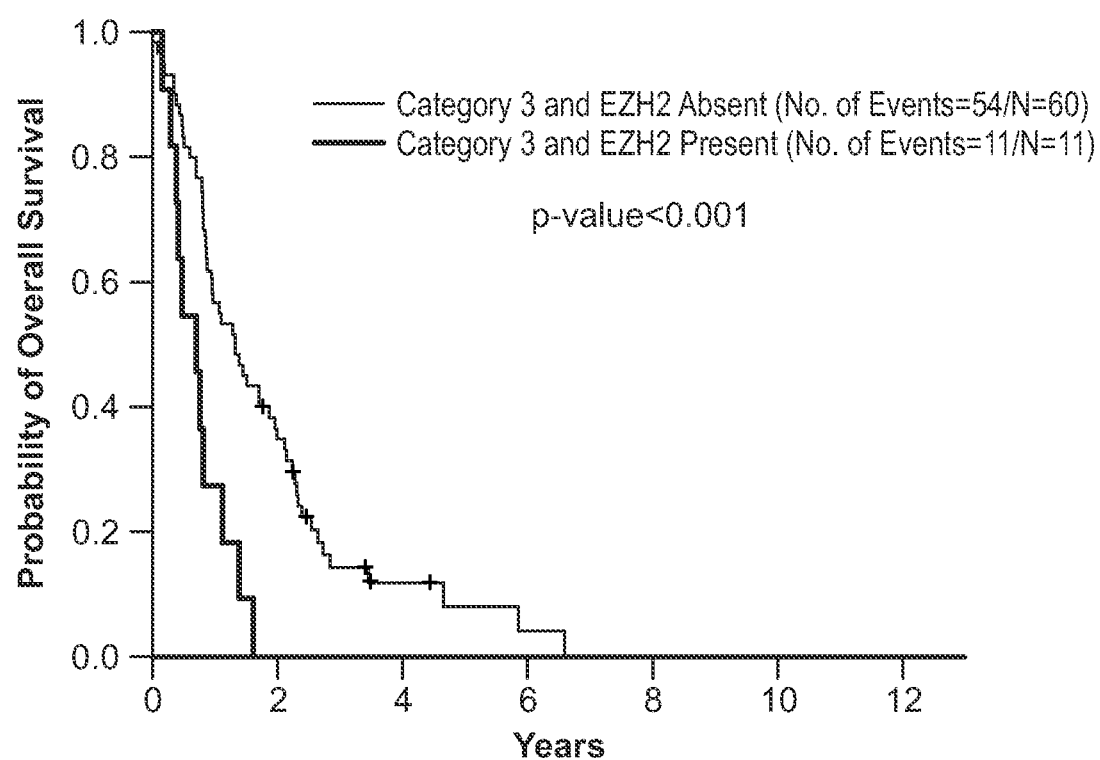
Figure 20A:
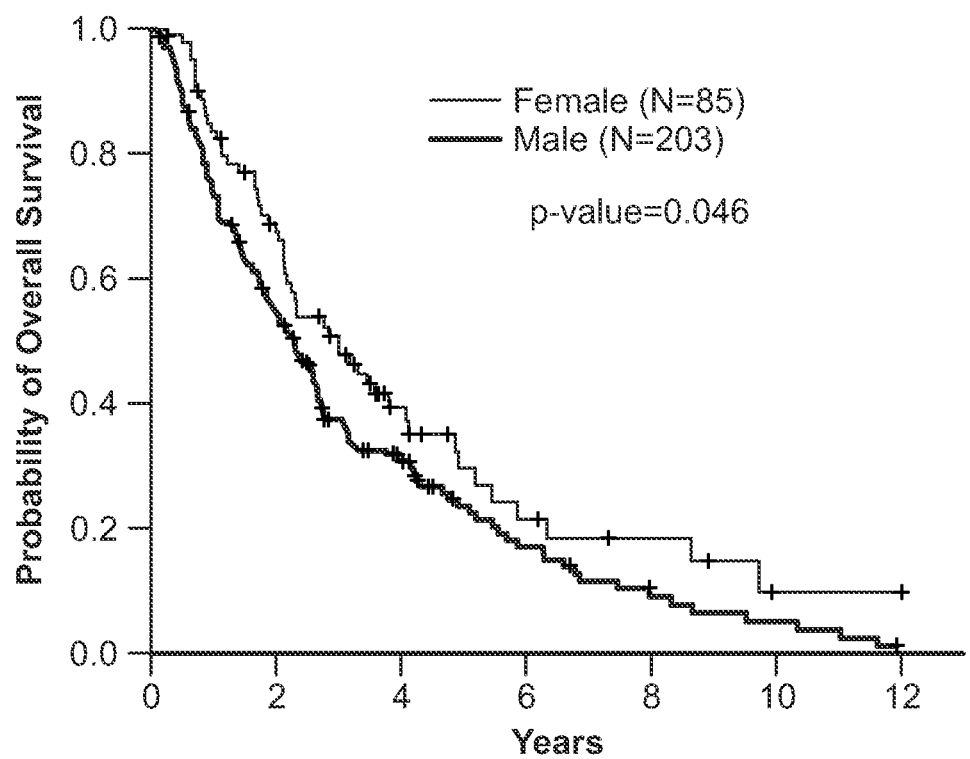
FIG. 20 shows Kaplan-Meier overall survival according to clinical features: A) patient sex; B) patient age; C) hemoglobin level; D) platelet count; E) bone marrow blast percentage.
Figure 20B:
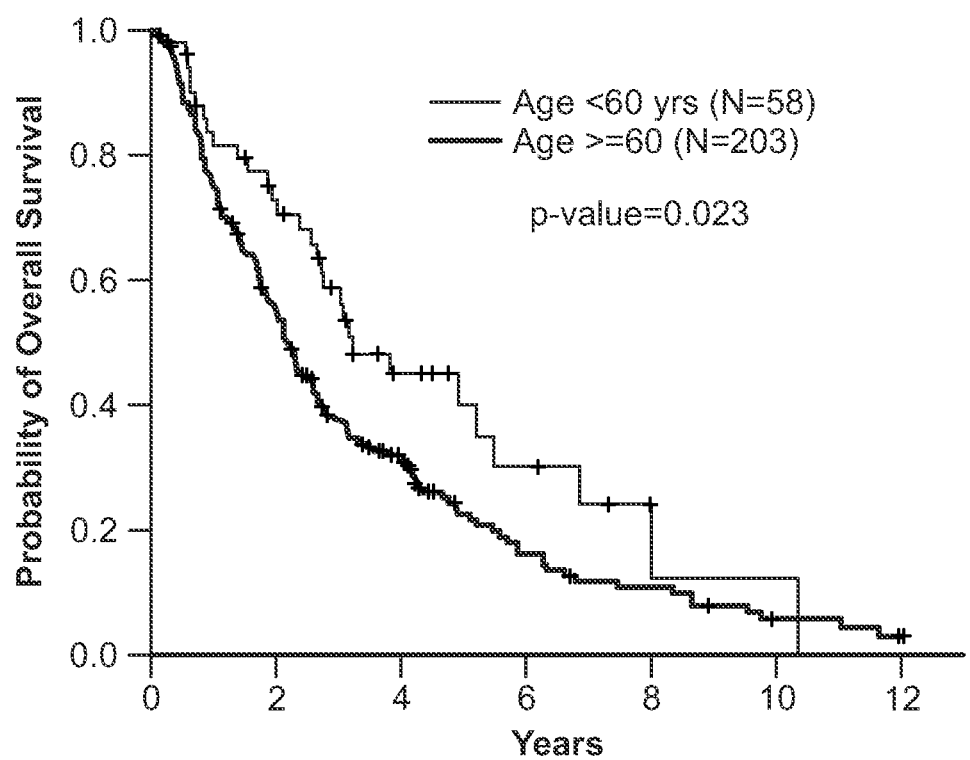
Figure 20C:
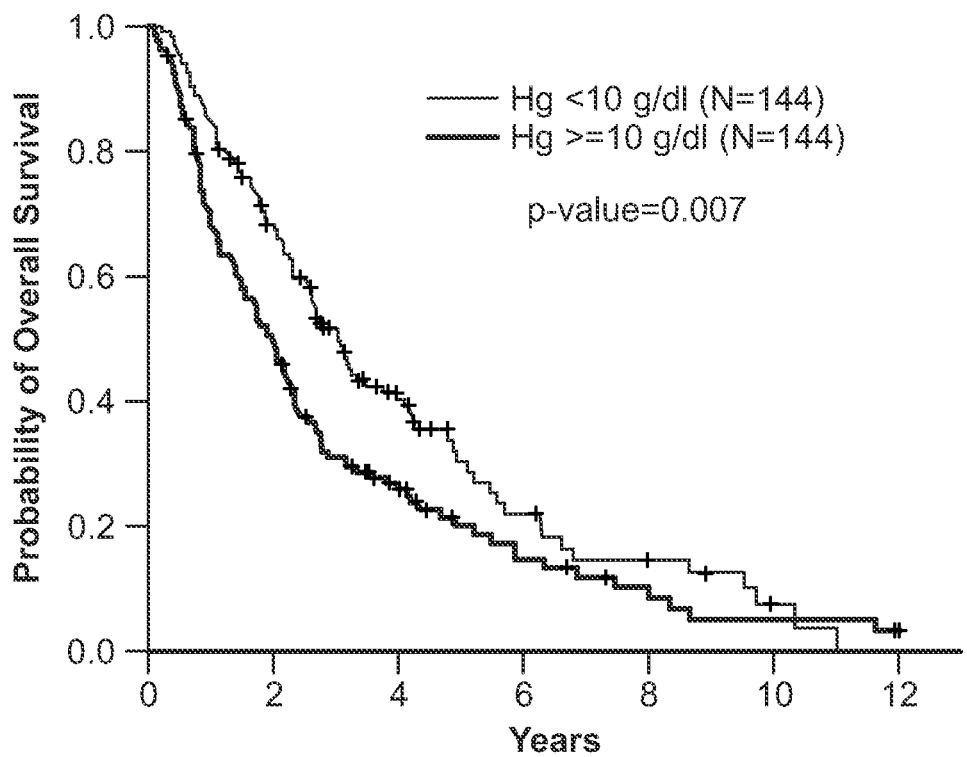
Figure 20D:
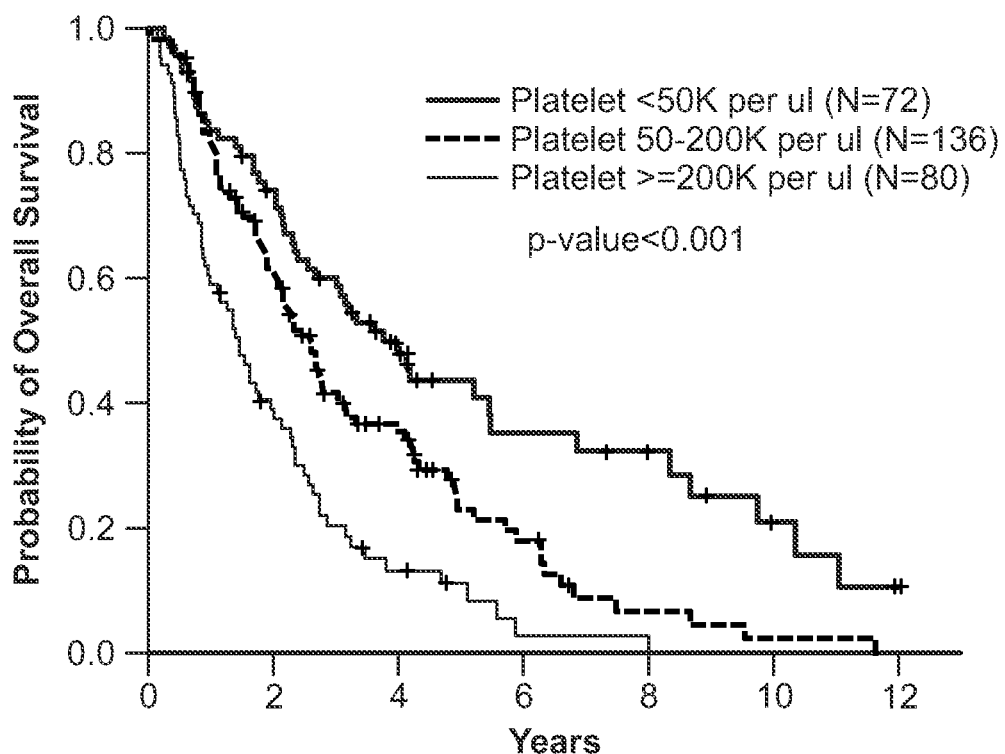
Figure 20E:
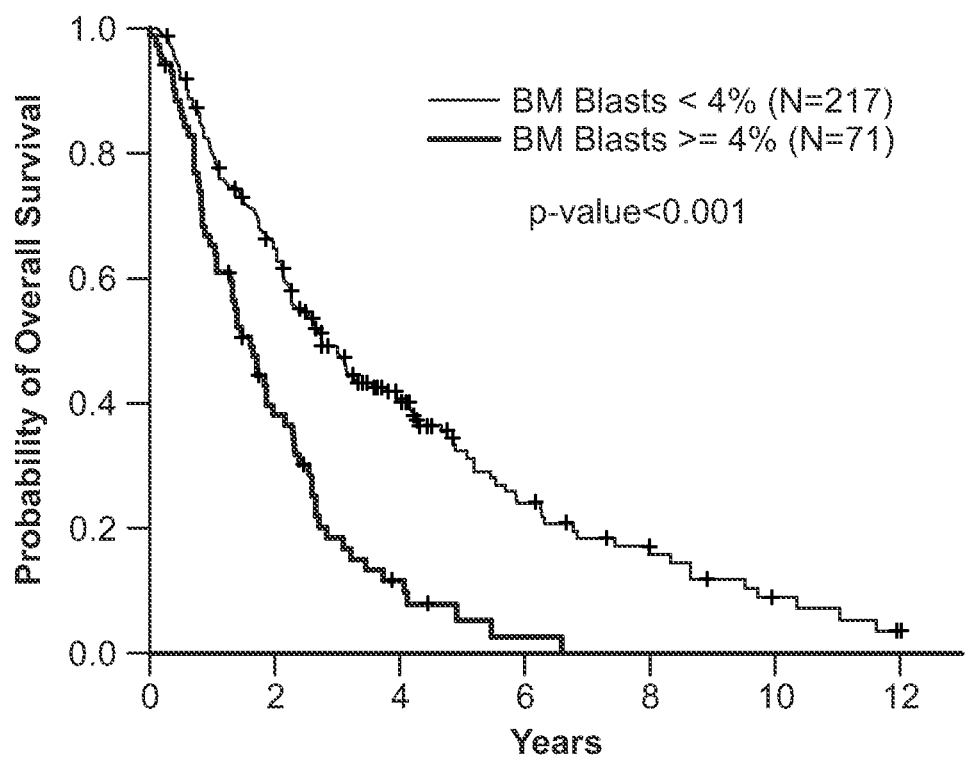
Figure 21:
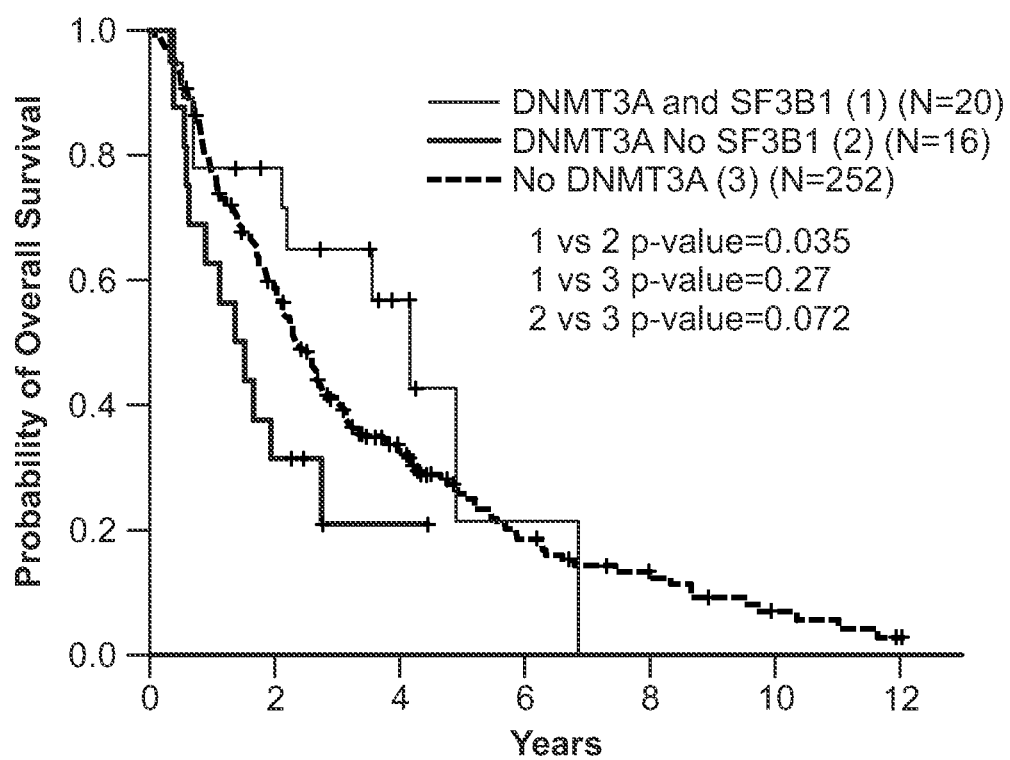
FIG. 21 shows overall survival of MDS patients with DNMT3A mutations stratified by their SF3B1 mutations status.
Figure 22A:
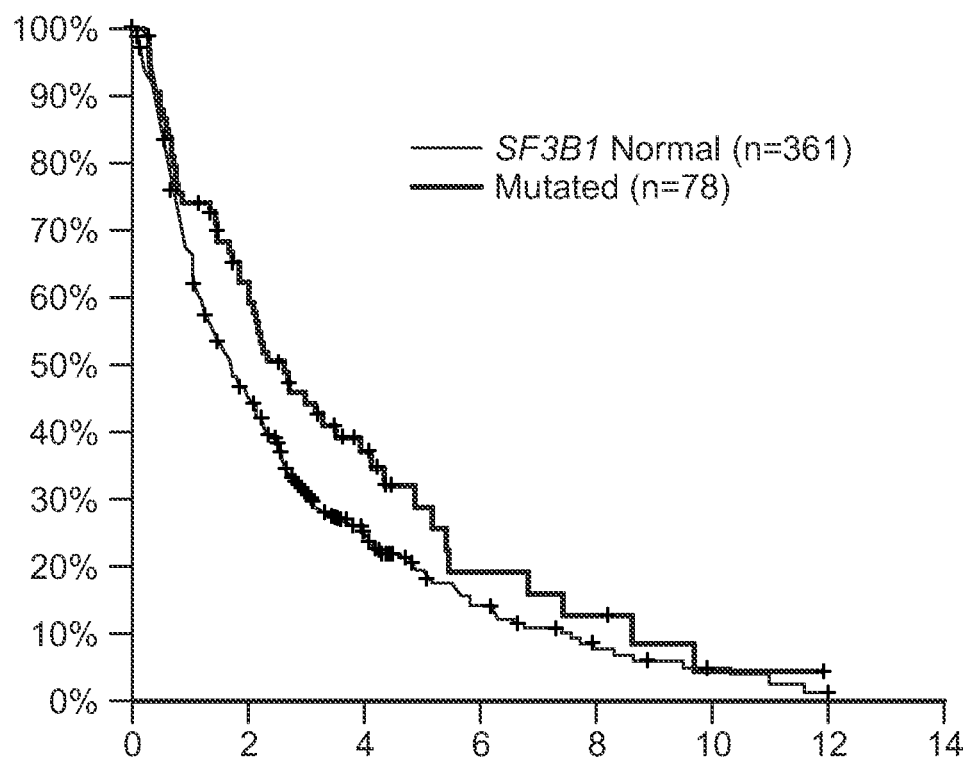
FIGS. 22A-22C show the survival curves for SF3B1 and/or DNMT3A mutation, demonstrating that mutations in SF3B1 co-occurred with mutations in DNMT3A more frequently than expected and modulated the survival of patients with DNMT3A mutations. Patients with mutations in both genes had longer survival than patients with mutations of just DNMT3A.
Figure 22B:
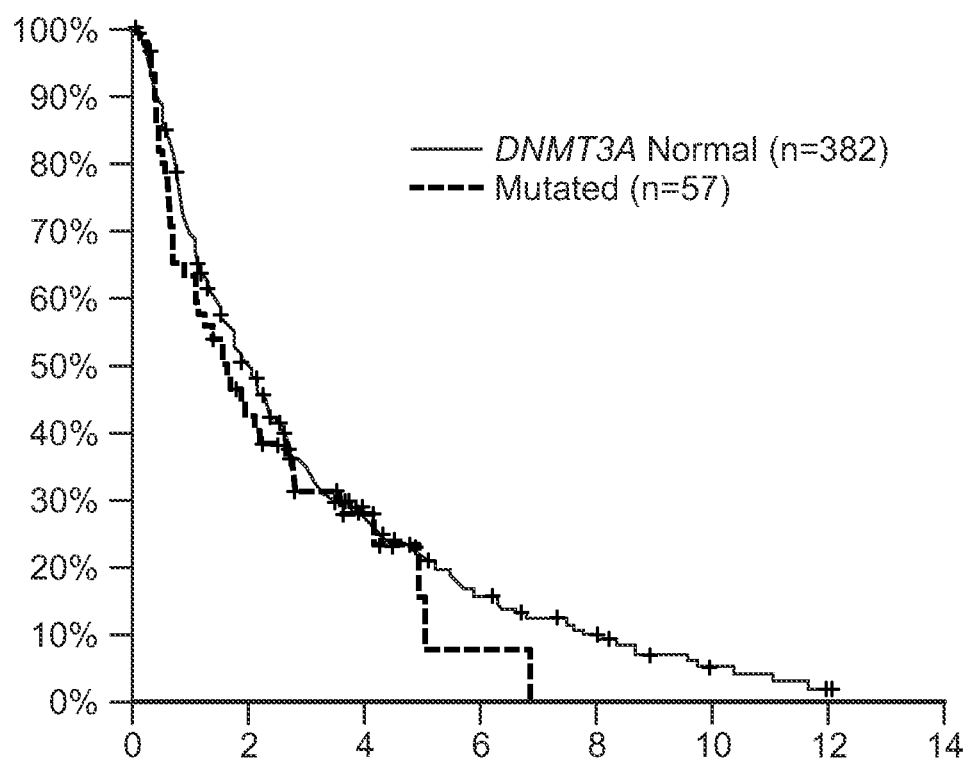
Figure 22C:
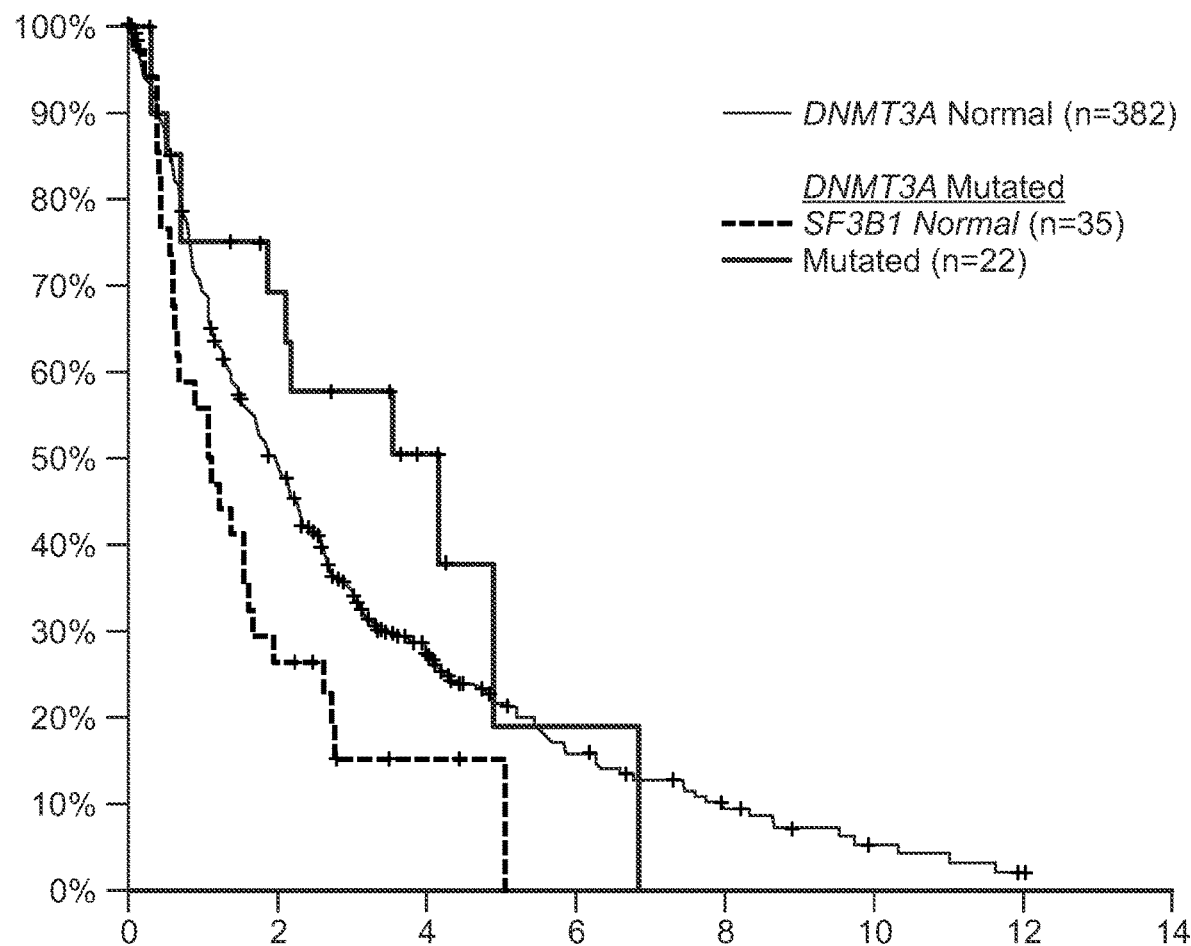
Figure 23A:
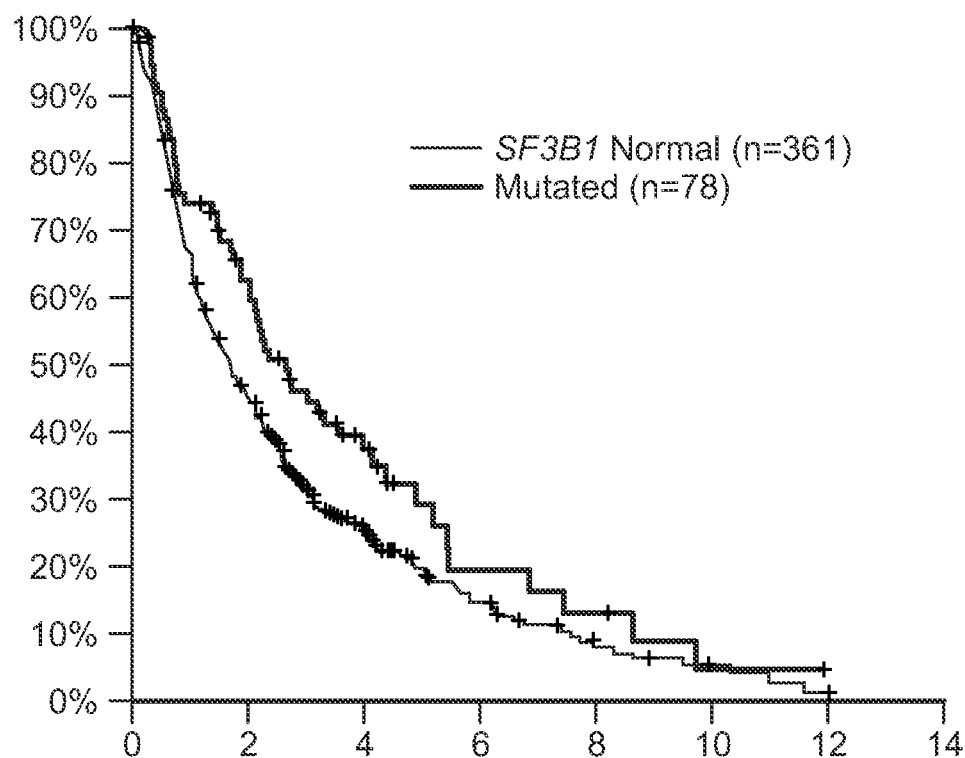
FIGS. 23A-23C show the survival curves for SF3B1 and/or TET2 mutation, demonstrating that patients harboring mutations in both genes living longer than those with TET2 mutations alone.
Figure 23B:
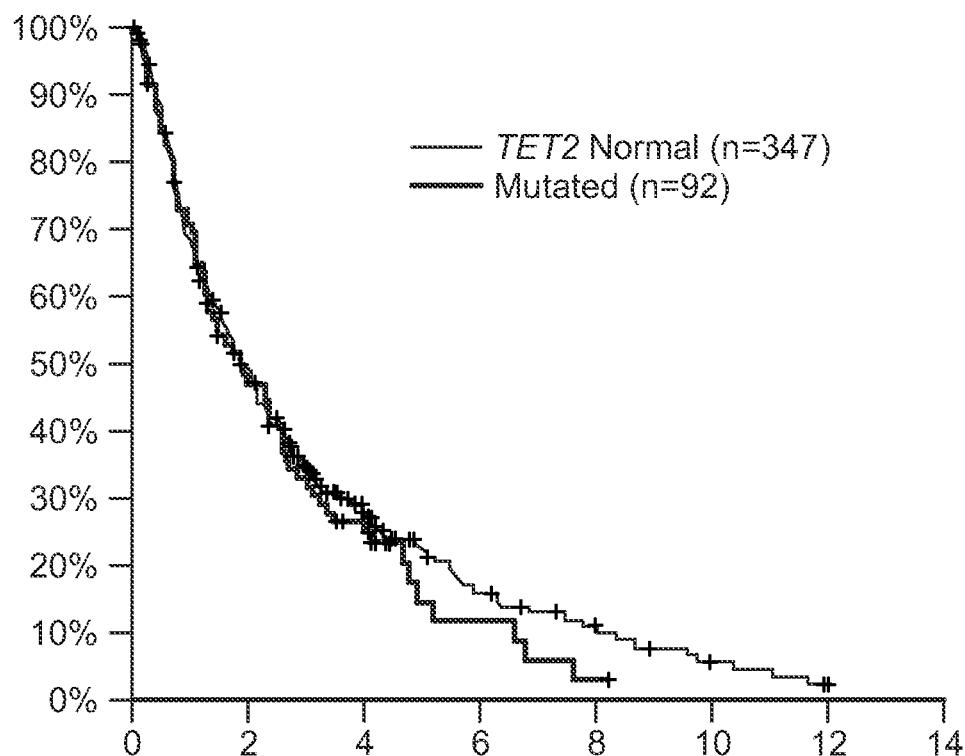
Figure 23C:
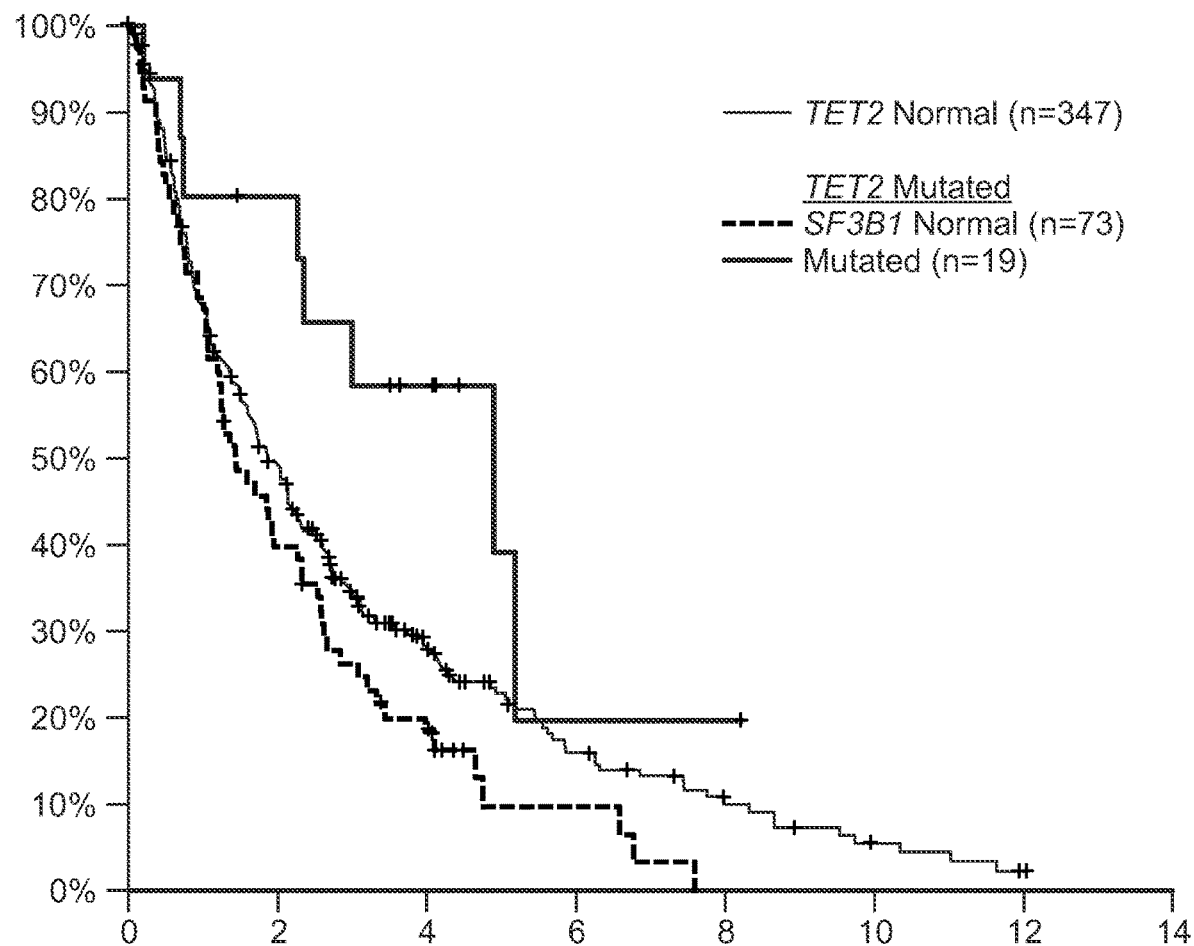
Figure 24A:
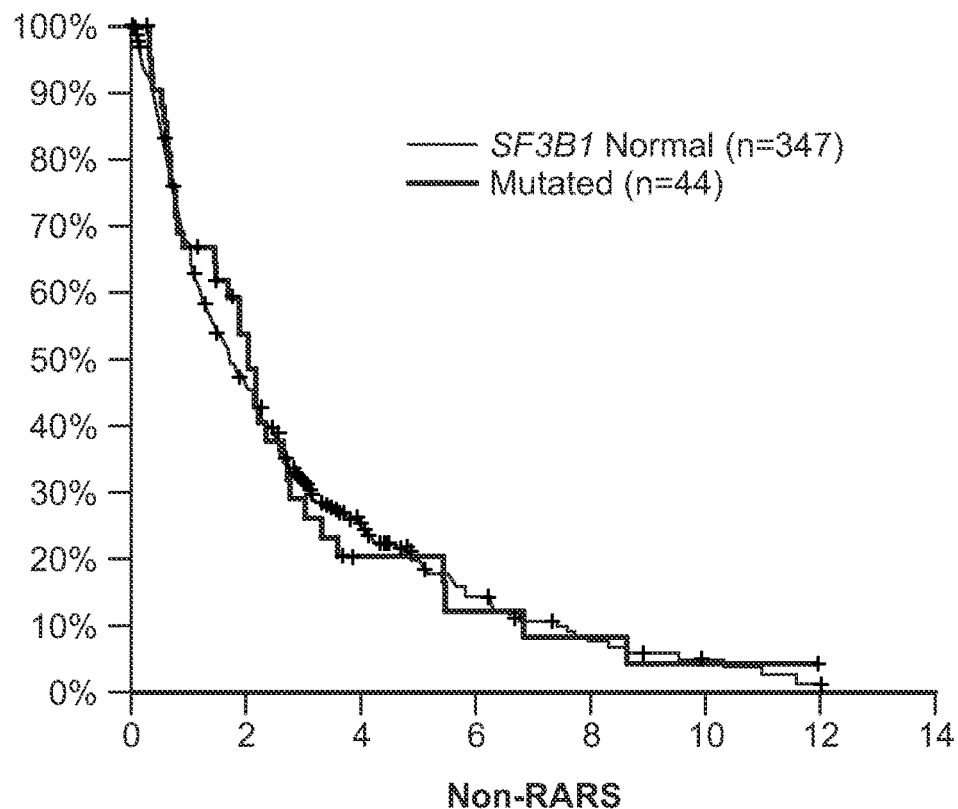
FIG. 24 shows that a longer overall survival in patients with the RARS subtype of MDS that also carried SF3B1 mutations.
Figure 24B:
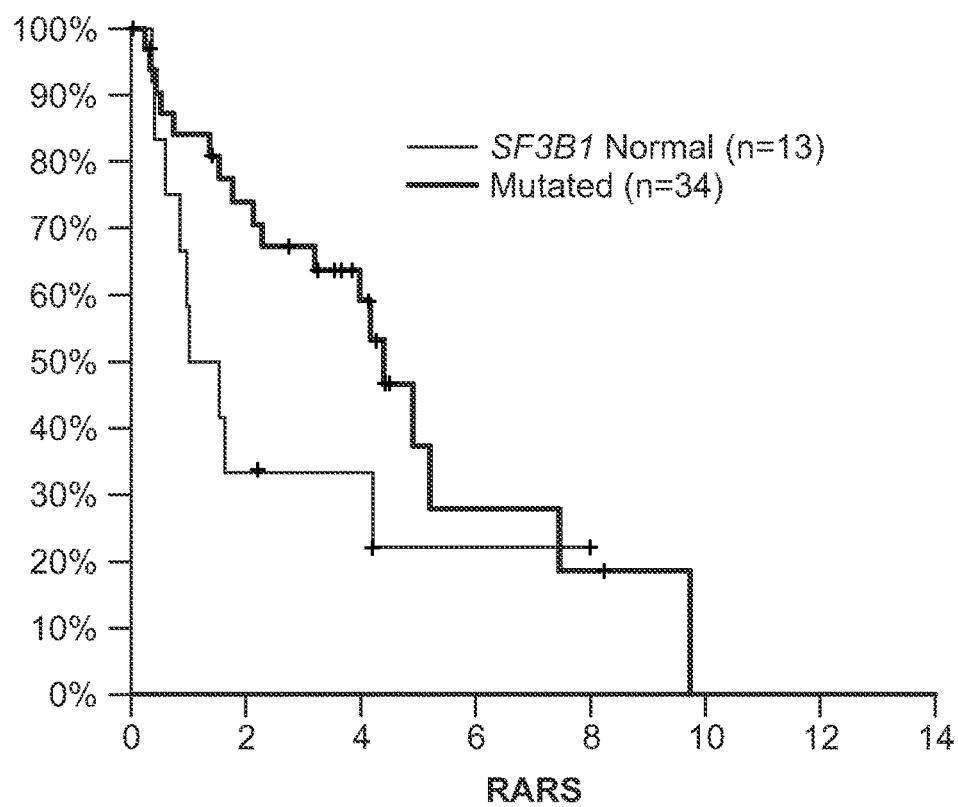

We next examined the association of mutation status with overall survival in our lower risk MDS cohort. In univariate analyses, mutations of ASXL1, RUNX1, EZH2, SRSF2, U2AF1 and NRAS were associated with shorter overall survival, with hazard ratios shown in Table 9 and survival curves in FIG. 19. Only mutations of SF3B1 showed a non-significant trend towards longer survival (HR 0.76, [CI, 0.54-1.07], p=0.12).

We next examined whether mutations predict prognosis after adjusting for the LR-PSS. The prognostic significance for most of the mutated genes was less marked after adjusting for LR-PSS risk category, indicating that the clinical parameters incorporated into the LR-PSS capture some of the prognostic significance of point mutations (Table 9). The adjusted hazard ratios fell to 1.56 (CI, 1.08-2.26) for ASXL1 mutations and 1.67 (CI, 1.07-2.61) for RUNX1 mutations. Mutations of NRAS, U2AF1, and SRSF2 were no longer significant after adjusting for the LR-PSS. Mutations of TP53 predicted a shorter overall survival after adjusting for either the IPSS (HR 2.43 [CI, 1.07-5.52]) or the LR-PSS (HR 2.63 [CI, 1.16-5.99]), but were rare in this cohort of lower risk MDS patients (n=7). Importantly, EZH2 mutations remained a powerful and significant predictor of overall survival after adjustment for LR-PSS risk categories (HR 2.90 [CI, 1.85-4.52]).

Since a significant portion of the predictive power of mutations is captured by the LR-PSS, we performed a stepwise multivariable Cox regression analysis to identify mutations that contribute significantly to the prediction of overall survival in addition to existing prognostic scoring systems, and would therefore be the most useful to analyze clinically. We first examined the IPSS, considering patient age (<60 vs. ≥60 years), sex, IPSS risk group, and the mutation status of each of the 15 genes mutated in more than 1% of cases as candidate variables in the model (Table 10). In addition to age and IPSS risk group, mutations of EZH2, NRAS, and ASXL1 were each independently associated with a higher risk of death in this model. Overall, 21% of patients carried one or more mutations in these genes indicating that more than one-fifth of patients categorized as lower risk MDS by the IPSS have mutations associated with worse prognosis.

In a similar model considering the LR-PSS risk categories in place of age and the IPSS risk groups, only EZH2 mutations remained as a significant predictor of shorter overall survival (HR 2.90 [CI, 1.85-4.52], FIG. 19) in addition to LR-PSS risk group. This analysis demonstrates that the LR-PSS considers clinical features that capture much of the prognostic information linked with gene mutations associated with a shorter overall survival. Nevertheless, mutations in EZH2 are highly significant predictors of overall survival with a hazard ratio of ≥2.84 in all models, and the impact of EZH2 mutations is not captured by either the IPSS or LR-PSS. Genetic analysis of EZH2 would therefore significantly improve prediction of prognosis in lower risk MDS.

TABLE 3

List of mutations predicted to disrupt protein sequence and included in the analysis.

| Gene Name | Ensembl Reference Transcript | RefSeq Reference Transcript | DNA Mutation | Protein Mutation | Confirmed Somatic in One or More Samples | Present in Two or More Samples |
|---|---|---|---|---|---|---|
| ASXL1 | ENST00000375687 | NM_015338.5 | c.1205G>A | p.R402Q | YES | |
| ASXL1 | ENST00000375687 | NM_015338.5 | c.1249C>T | p.R417* | YES | |
| ASXL1 | ENST00000375687 | NM_015338.5 | c.1282C>T | p.Q428* | | |
| ASXL1 | ENST00000375687 | NM_015338.5 | c.1285G>T | p.E429* | | |
| ASXL1 | ENST00000375687 | NM_015338.5 | c.1291G>T | p.E431* | YES | |
| ASXL1 | ENST00000375687 | NM_015338.5 | c.1534C>T | p.Q512* | | |
| ASXL1 | ENST00000375687 | NM_015338.5 | c.1747_1757delTGGGTGGTTAA | p.W583RfsX32 | | |
| ASXL1 | ENST00000375687 | NM_015338.5 | c.1772dupA | p.Y591* | | YES |
| ASXL1 | ENST00000375687 | NM_015338.5 | c.1900_1922delAGAGAGGCGGCACCACTGCCAT | p.E635RfsX15 | YES | YES |
| ASXL1 | ENST00000375687 | NM_015338.5 | c.1917_1928delTGCCATCGGAGGinsC | p.A640GfsX14 | YES | |
| ASXL1 | ENST00000375687 | NM_015338.5 | c.1924_1929delGGAGGGGinsT | p.G642WfsX14 | YES | |
| ASXL1 | ENST00000375687 | NM_015338.5 | c.1926_1930delAGGGG | p.G644WfsX12 | | |
| ASXL1 | ENST00000375687 | NM_015338.5 | c.1934dupG | p.G646WfsX12 | YES | |
| ASXL1 | ENST00000375687 | NM_015338.5 | c.1979_1982dupGCAG | p.G662QfsX7 | | |
| ASXL1 | ENST00000375687 | NM_015338.5 | c.2035G>T | p.G679* | | |
| ASXL1 | ENST00000375687 | NM_015338.5 | c.2036dupG | p.G680RfsX38 | | |
| ASXL1 | ENST00000375687 | NM_015338.5 | c.2041_2042delCC | p.P681EfsX36 | | |
| ASXL1 | ENST00000375687 | NM_015338.5 | c.2069_2076delATCTACAG | p.D690AfsX25 | YES | |
| ASXL1 | ENST00000375687 | NM_015338.5 | c.2077C>T | p.R693* | YES | YES |
| ASXL1 | ENST00000375687 | NM_015338.5 | c.2088_2111delACTGCCGCCTTATCCTCTAAATGGinsTAGA | p.L697RfsX14 | | |
| ASXL1 | ENST00000375687 | NM_015338.5 | c.2110G>A | p.G704R | | |
| ASXL1 | ENST00000375687 | NM_015338.5 | c.2172_2176dupGAGAA | p.K726RfsX20 | YES | |
| ASXL1 | ENST00000375687 | NM_015338.5 | c.2226delG | p.L743* | | |
| ASXL1 | ENST00000375687 | NM_015338.5 | c.2242C>T | p.Q748* | | |
| ASXL1 | ENST00000375687 | NM_015338.5 | c.2253delT | p.A752LfsX20 | | |
| ASXL1 | ENST00000375687 | NM_015338.5 | c.2269C>T | p.Q757* | YES | |
| ASXL1 | ENST00000375687 | NM_015338.5 | c.2278C>T | p.Q760* | YES | |
| ASXL1 | ENST00000375687 | NM_015338.5 | c.2322delA | p.R774SfsX2 | | |
| ASXL1 | ENST00000375687 | NM_015338.5 | c.2332C>T | p.Q778* | | |
| ASXL1 | ENST00000375687 | NM_015338.5 | c.2395G>T | p.D799Y | | |
| ASXL1 | ENST00000375687 | NM_015338.5 | c.2415dupC | p.T806HfsX16 | YES | |
| ASXL1 | ENST00000375687 | NM_015338.5 | c.2423dupC | p.A809CfsX13 | | |
| ASXL1 | ENST00000375687 | NM_015338.5 | c.2485C>T | p.Q829* | | |
| ASXL1 | ENST00000375687 | NM_015338.5 | c.2629G>T | p.E877* | | |
| ASXL1 | ENST00000375687 | NM_015338.5 | c.2681delG | p.S894IfsX14 | | |
| ASXL1 | ENST00000375687 | NM_015338.5 | c.2693G>A | p.W898* | | |
| ASXL1 | ENST00000375687 | NM_015338.5 | c.2708C>A | p.S903* | | |
| ASXL1 | ENST00000375687 | NM_015338.5 | c.2777dupA | p.P920TfsX4 | | |
| ASXL1 | ENST00000375687 | NM_015338.5 | c.2777_2780dupTTGG | p.E928WfsX21 | YES | |
| ASXL1 | ENST00000375687 | NM_015338.5 | c.2917dupA | p.S973KfsX9 | YES | |
| ASXL1 | ENST00000375687 | NM_015338.5 | c.2945delA | p.K982SfsX2 | | |
| ASXL1 | ENST00000375687 | NM_015338.5 | c.2973_2985delACTGAGTCCTCAC | p.L992VfsX28 | | |
| ASXL1 | ENST00000375687 | NM_015338.5 | c.3050delA | p.D1017AfsX7 | | |
| ASXL1 | ENST00000375687 | NM_015338.5 | c.3083C>A | p.S1028* | | |

TABLE 3-continued

List of mutations predicted to disrupt protein sequence and included in the analysis.

| Gene Name | Ensembl Reference Transcript | RefSeq Reference Transcript | DNA Mutation | Protein Mutation | Confirmed Somatic in One or More Samples | Present in Two or More Samples |
|---|---|---|---|---|---|---|
| ASXL1 | ENST00000375687 | NM_015338.5 | c.3187C>T | p.Q1063* | | |
| ASXL1 | ENST00000375687 | NM_015338.5 | c.3401C>T | p.P1134L | | |
| ASXL1 | ENST00000375687 | NM_015338.5 | c.3601delC | p.Q1201KfsX16 | YES | |
| ASXL1 | ENST00000375687 | NM_015338.5 | c.3758_3759insC | p.N1254* | YES | |
| BRAF | ENST00000288602 | NM_004333.4 | c.4456G>A | p.A1486T | | |
| BRAF | ENST00000288602 | NM_004333.4 | c.1790T>A | p.L597Q | | |
| CBL | ENST00000264033 | NM_005188.2 | c.1799T>A | p.V600E | | |
| CBL | ENST00000264033 | NM_005188.2 | c.1122_1127delGGGCTC | p.M374_S376delinsI | | |
| CBL | ENST00000264033 | NM_005188.2 | c.1142G>A | p.C381Y | YES | |
| CBL | ENST00000264033 | NM_005188.2 | c.1143T>G | p.C381W | YES | |
| CBL | ENST00000264033 | NM_005188.2 | c.1151G>A | p.C384Y | | |
| CBL | ENST00000264033 | NM_005188.2 | c.1216A>C | p.T406P | | |
| CBL | ENST00000264033 | NM_005188.2 | c.1247G>A | p.C416Y | YES | |
| CBL | ENST00000264033 | NM_005188.2 | c.1253T>C | p.F418S | YES | |
| CBL | ENST00000264033 | NM_005188.2 | c.1258C>T | p.R420* | YES | |
| CBL | ENST00000264033 | NM_005188.2 | c.1259G>A | p.R420Q | | YES |
| CBL | ENST00000264033 | NM_005188.2 | c.1292T>C | p.V431A | YES | |
| CBL | ENST00000264033 | NM_005188.2 | c.1301T>C | p.F434S | | |
| CDKN2A-p16INK4A/p14ARF | ENST00000304494/ENST00000361570 | NM_000077.3/NM_058195.2 | c.198C>G/c.364C>G | p.H66Q/p.R122G | YES | |
| ELANE | ENST00000263621 | NM_001972.2 | c.257C>T | p.A86V | | |
| ELANE | ENST00000263621 | NM_001972.2 | c.751G>T | p.D251Y | | |
| ETV6 | ENST00000266427 | NM_001987.4 | c.195_197dupCGT | p.A66_V67insV | | |
| ETV6 | ENST00000266427 | NM_001987.4 | c.290T>C | p.L97P | | |
| ETV6 | ENST00000266427 | NM_001987.4 | c.306dupT | p.R103SfsX9 | | |
| ETV6 | ENST00000266427 | NM_001987.4 | c.380G>A | p.R127Q | | |
| ETV6 | ENST00000266427 | NM_001987.4 | c.419_420dupTA | p.H141YfsX69 | | |
| ETV6 | ENST00000266427 | NM_001987.4 | c.463G>C | p.D155H | YES | |
| ETV6 | ENST00000266427 | NM_001987.4 | c.537dupG | p.H180AfsX16 | YES | |
| ETV6 | ENST00000266427 | NM_001987.4 | c.602T>C | p.L201P | YES | |
| ETV6 | ENST00000266427 | NM_001987.4 | c.1075C>T | p.R359* | | YES |
| EZH2 | ENST00000320356 | NM_004456.3 | c.72dupG | p.R25AfsX12 | | |
| EZH2 | ENST00000320356 | NM_004456.3 | c.130delT | p.S44PfsX13 | | |
| EZH2 | ENST00000320356 | NM_004456.3 | c.151G>T | p.E51* | YES | |
| EZH2 | ENST00000320356 | NM_004456.3 | c.187C>T | p.R63* | YES | |
| EZH2 | ENST00000320356 | NM_004456.3 | c.349C>T | p.Q117* | | |
| EZH2 | ENST00000320356 | NM_004456.3 | c.393_394delTCinsGA | p.I131_P132delinsMT | YES | |
| EZH2 | ENST00000320356 | NM_004456.3 | c.401T>A | p.M134K | | |
| EZH2 | ENST00000320356 | NM_004456.3 | c.487_507delTGTGGGTTTATAAATGATGAA | p.163_169delCGFNDE | | |
| EZH2 | ENST00000320356 | NM_004456.3 | c.698A>G | p.D233G | YES | |
| EZH2 | ENST00000320356 | NM_004456.3 | c.729-2A>T | Splice Disruption | | |
| EZH2 | ENST00000320356 | NM_004456.3 | c.893G>A | p.R298H | | |
| EZH2 | ENST00000320356 | NM_004456.3 | c.1119dupC | p.T374HfsX3 | | |
| EZH2 | ENST00000320356 | NM_004456.3 | c.1370G>A | p.C457Y | | |
| EZH2 | ENST00000320356 | NM_004456.3 | c.1483delA | p.R495GfsX19 | | |

TABLE 3-continued

List of mutations predicted to disrupt protein sequence and included in the analysis.

| Gene Name | Ensembl Reference Transcript | RefSeq Reference Transcript | DNA Mutation | Protein Mutation | Confirmed Somatic in One or More Samples | Present in Two or More Samples |
|---|---|---|---|---|---|---|
| EZH2 | ENST00000320356 | NM_004456.3 | c.1505+5G>A | Splice Disruption | | |
| EZH2 | ENST00000320356 | NM_004456.3 | c.1615T>C | p.C539R | YES | |
| EZH2 | ENST00000320356 | NM_004456.3 | c.1700G>A | p.C567Y | YES | |
| EZH2 | ENST00000320356 | NM_004456.3 | c.1723C>T | p.Q575* | YES | |
| EZH2 | ENST00000320356 | NM_004456.3 | c.1739T>C | p.L580P | | |
| EZH2 | ENST00000320356 | NM_004456.3 | c.1747C>T | p.R583* | | YES |
| EZH2 | ENST00000320356 | NM_004456.3 | c.1852−6C>T | Splice Disruption | | |
| EZH2 | ENST00000320356 | NM_004456.3 | c.1957C>G | p.Q653E | YES | |
| EZH2 | ENST00000320356 | NM_004456.3 | c.1969G>C | p.D657H | YES | YES |
| EZH2 | ENST00000320356 | NM_004456.3 | c.1987T>C | p.Y663H | YES | |
| EZH2 | ENST00000320356 | NM_004456.3 | c.2008T>C | p.F670L | | |
| EZH2 | ENST00000320356 | NM_004456.3 | c.2029+1G>T | Splice Disruption | | |
| EZH2 | ENST00000320356 | NM_004456.3 | c.2069G>A | p.R690H | YES | |
| EZH2 | ENST00000320356 | NM_004456.3 | c.2110+1G>T | Splice Disruption | | |
| EZH2 | ENST00000320356 | NM_004456.3 | c.2111−2A>T | Splice Disruption | | |
| EZH2 | ENST00000320356 | NM_004456.3 | c.2187delT | p.F729LfsX11 | | |
| FLNB | ENST00000295956 | NM_011457.3 | c.1697G>A | p.R566Q | | |
| GNAS | ENST00000371082 | NM_005164 | c.601C>T | p.R201C | | |
| GNAS | ENST00000371082 | NM_005164 | c.602G>A | p.R201H | YES | YES |
| IDH1 | ENST00000415913 | NM_005896.2 | c.394C>G | p.R132G | | YES |
| IDH1 | ENST00000415913 | NM_005896.2 | c.395G>A | p.R132H | | YES |
| IDH2 | ENST00000330062 | NM_002168.2 | c.419G>A | p.R140Q | YES | YES |
| IDH2 | ENST00000330062 | NM_002168.2 | c.515G>A | p.R172K | | YES |
| JAK2 | ENST00000381652 | NM_004972.3 | c.1849G>T | p.V617F | YES | YES |
| KRAS | ENST00000395977 | NM_033360.2 | c.34G>C | p.G12R | | YES |
| KRAS | ENST00000395977 | NM_033360.2 | c.35G>T | p.G12V | | YES |
| KRAS | ENST00000395977 | NM_033360.2 | c.183C>T | p.Q61H | | YES |
| KRAS | ENST00000395977 | NM_033360.2 | c.436G>A | p.A146T | | |
| NPM1 | ENST00000296930 | NM_002520.5 | c.860_863dupTCTG | p.W288CfsX12 | | YES |
| NPM1 | ENST00000296930 | NM_002520.5 | c.863_864insCATG | p.W288CfsX12 | | |
| NPM1 | ENST00000296930 | NM_002520.5 | c.863_864insTATG | p.W288CfsX12 | | |
| NRAS | ENST00000369535 | NM_002524.3 | c.34G>A | p.G12S | YES | YES |
| NRAS | ENST00000369535 | NM_002524.3 | c.34G>C | p.G12R | | YES |
| NRAS | ENST00000369535 | NM_002524.3 | c.35G>A | p.G12D | | YES |
| NRAS | ENST00000369535 | NM_002524.3 | c.35G>T | p.G12V | | YES |
| NRAS | ENST00000369535 | NM_002524.3 | c.37G>C | p.G13R | | YES |
| NRAS | ENST00000369535 | NM_002524.3 | c.38G>A | p.G13D | | |
| NRAS | ENST00000369535 | NM_002524.3 | c.38G>T | p.G13V | YES | YES |
| NRAS | ENST00000369535 | NM_002524.3 | c.181C>A | p.Q61K | | |
| PTEN | ENST00000371953 | NM_000314.4 | c.947T>A | p.L316Q | | YES |
| PTPN11 | ENST00000351677 | NM_002834.3 | c.214G>A | p.A72T | YES | |
| PTPN11 | ENST00000351677 | NM_002834.3 | c.226G>A | p.E76K | YES | |
| RUNX1 | ENST00000300305 | NM_001754.4 | c.352−1G>A | Splice Disruption | YES | |
| RUNX1 | ENST00000300305 | NM_001754.4 | c.364G>A | p.G122R | | |
| RUNX1 | ENST00000300305 | NM_001754.4 | c.398_400dupTGG | p.M133_A134insV | | |

TABLE 3-continued

List of mutations predicted to disrupt protein sequence and included in the analysis.

| Gene Name | Ensembl Reference Transcript | RefSeq Reference Transcript | DNA Mutation | Protein Mutation | Confirmed Somatic in One or More Samples | Present in Two or More Samples |
|---|---|---|---|---|---|---|
| RUNX1 | ENST00000300305 | NM_001754.4 | c.401C>T | p.A134V | YES | |
| RUNX1 | ENST00000300305 | NM_001754.4 | c.404G>A | p.G135D | YES | |
| RUNX1 | ENST00000300305 | NM_001754.4 | c.422C>T | p.S141L | | YES |
| RUNX1 | ENST00000300305 | NM_001754.4 | c.436A>G | p.N146D | | |
| RUNX1 | ENST00000300305 | NM_001754.4 | c.432_441dupGAGAAATGCT | p.T148EfsX15 | | |
| RUNX1 | ENST00000300305 | NM_001754.4 | c.472T>A | p.F158I | YES | |
| RUNX1 | ENST00000300305 | NM_001754.4 | c.479A>G | p.D160G | | |
| RUNX1 | ENST00000300305 | NM_001754.4 | c.482T>C | p.L161P | YES | |
| RUNX1 | ENST00000300305 | NM_001754.4 | c.486G>C | p.R162S | | |
| RUNX1 | ENST00000300305 | NM_001754.4 | c.496C>G | p.R166G | YES | |
| RUNX1 | ENST00000300305 | NM_001754.4 | c.496C>T | p.R166* | | |
| RUNX1 | ENST00000300305 | NM_001754.4 | c.497G>A | p.R166Q | | |
| RUNX1 | ENST00000300305 | NM_001754.4 | c.504_508+1dupAAGAGG | p.G168_R169dup | | |
| RUNX1 | ENST00000300305 | NM_001754.4 | c.494_497dupGTCG | p.G168KfsX46 | | |
| RUNX1 | ENST00000300305 | NM_001754.4 | c.508+4_508+5insCAAGGAAAAA | Splice Disruption | | |
| RUNX1 | ENST00000300305 | NM_001754.4 | c.508+5G>A | Splice Disruption | | |
| RUNX1 | ENST00000300305 | NM_001754.4 | c.511A>T | p.K171* | | |
| RUNX1 | ENST00000300305 | NM_001754.4 | c.592G>A | p.D198N | | YES |
| RUNX1 | ENST00000300305 | NM_001754.4 | c.601C>T | p.R201* | YES | YES |
| RUNX1 | ENST00000300305 | NM_001754.4 | c.602G>A | p.R201Q | | |
| RUNX1 | ENST00000300305 | NM_001754.4 | c.610C>T | p.R204* | YES | |
| RUNX1 | ENST00000300305 | NM_001754.4 | c.613+2T>G | Splice Disruption | YES | |
| RUNX1 | ENST00000300305 | NM_001754.4 | c.620G>A | p.R207Q | | |
| RUNX1 | ENST00000300305 | NM_001754.4 | c.714_727delCAGCCCACCACC | p.H242AfsX14 | YES | |
| RUNX1 | ENST00000300305 | NM_001754.4 | c.861C>A | p.Y287* | YES | |
| RUNX1 | ENST00000300305 | NM_001754.4 | c.961_962delCT | p.S322NfsX277 | YES | |
| RUNX1 | ENST00000300305 | NM_001754.4 | c.965C>G | p.S322* | YES | |
| RUNX1 | ENST00000300305 | NM_001754.4 | c.1057_1070delTTCACCTACTCCCC | p.F353DfsX242 | | |
| RUNX1 | ENST00000300305 | NM_001754.4 | c.1070delC | p.P357RfsX237 | | |
| RUNX1 | ENST00000300305 | NM_001754.4 | c.1203dupC | p.S402LfsX198 | | |
| RUNX1 | ENST00000300305 | NM_001754.4 | c.1203_1206dupCTCC | p.Y403LfsX198 | | |
| RUNX1 | ENST00000300305 | NM_001754.4 | c.1208_1209insT | p.H404PfsX196 | | |
| RUNX1 | ENST00000300305 | NM_001754.4 | c.1239_1246delCTACCAGT | p.Y414LfsX183 | YES | |
| RUNX1 | ENST00000300305 | NM_001754.4 | c.1274C>T | p.P425L | | |
| TET2 | ENST00000380013 | NM_001127208.1 | c.428delA | p.D143VfsX2 | | |
| TET2 | ENST00000380013 | NM_001127208.1 | c.444_468dupAGAATCTGTGAGTTCTGTAGCCCAA | p.E157RfsX13 | | |
| TET2 | ENST00000380013 | NM_001127208.1 | c.551_552delAG | p.E184AfsX7 | | |
| TET2 | ENST00000380013 | NM_001127208.1 | c.578delA | p.H193LfsX14 | | |
| TET2 | ENST00000380013 | NM_001127208.1 | c.651delC | p.V218WfsX32 | | |
| TET2 | ENST00000380013 | NM_001127208.1 | c.727C>T | p.Q243* | | |
| TET2 | ENST00000380013 | NM_001127208.1 | c.744C>A | p.H248Q | YES | |
| TET2 | ENST00000380013 | NM_001127208.1 | c.822delC | p.N275IfsX18 | | |
| TET2 | ENST00000380013 | NM_001127208.1 | c.1122delT | p.N374KfsX3 | | YES |
| TET2 | ENST00000380013 | NM_001127208.1 | c.1128G>A | p.M376I | | |
| TET2 | ENST00000380013 | NM_001127208.1 | c.1128delG | p.M376IfsX51 | | |
| TET2 | ENST00000380013 | NM_001127208.1 | c.1326_1327delCA | p.T443NfsX11 | | |

TABLE 3-continued

List of mutations predicted to disrupt protein sequence and included in the analysis.

| Gene Name | Ensembl Reference Transcript | RefSeq Reference Transcript | DNA Mutation | Protein Mutation | Confirmed Somatic in One or More Samples | Present in Two or More Samples |
|---|---|---|---|---|---|---|
| TET2 | ENST00000380013 | NM_001127208.1 | c.1342dupG | p.F448GfsX7 | | |
| TET2 | ENST00000380013 | NM_001127208.1 | c.1473_1497delGACTGCAGGGACAATGACTGTTCCA | p.Q491HfsX34 | YES | YES |
| TET2 | ENST00000380013 | NM_001127208.1 | c.1591C>T | p.Q531* | YES | |
| TET2 | ENST00000380013 | NM_001127208.1 | c.1630C>T | p.R544* | | YES |
| TET2 | ENST00000380013 | NM_001127208.1 | c.1648C>T | p.R550* | | |
| TET2 | ENST00000380013 | NM_001127208.1 | c.1699_1703delTTGAA | p.L567GfsX14 | YES | |
| TET2 | ENST00000380013 | NM_001127208.1 | c.1795C>T | p.Q599* | YES | |
| TET2 | ENST00000380013 | NM_001127208.1 | c.1903C>T | p.Q635* | | |
| TET2 | ENST00000380013 | NM_001127208.1 | c.1924C>T | p.Q642* | | |
| TET2 | ENST00000380013 | NM_001127208.1 | c.1928_1935delCCCAAGGT | p.S643YfsX35 | | |
| TET2 | ENST00000380013 | NM_001127208.1 | c.1970C>G | p.S657* | YES | |
| TET2 | ENST00000380013 | NM_001127208.1 | c.2053C>T | p.Q685* | YES | |
| TET2 | ENST00000380013 | NM_001127208.1 | c.2101C>T | p.Q701* | YES | |
| TET2 | ENST00000380013 | NM_001127208.1 | c.2176C>T | p.Q726* | | |
| TET2 | ENST00000380013 | NM_001127208.1 | c.2233C>T | p.Q745* | YES | |
| TET2 | ENST00000380013 | NM_001127208.1 | c.2249_2252delTAAA | p.I750RfsX62 | | |
| TET2 | ENST00000380013 | NM_001127208.1 | c.2280delT | p.P761LfsX52 | | |
| TET2 | ENST00000380013 | NM_001127208.1 | c.2318_2321dupGATC | p.F775IfsX7 | | |
| TET2 | ENST00000380013 | NM_001127208.1 | c.2386G>C | p.E796Q | YES | |
| TET2 | ENST00000380013 | NM_001127208.1 | c.2392G>T | p.E798* | | |
| TET2 | ENST00000380013 | NM_001127208.1 | c.2525C>G | p.S842* | YES | |
| TET2 | ENST00000380013 | NM_001127208.1 | c.2554G>T | p.E852* | | |
| TET2 | ENST00000380013 | NM_001127208.1 | c.2650C>T | p.Q884* | | |
| TET2 | ENST00000380013 | NM_001127208.1 | c.2759dupT | p.L920FfsX4 | | |
| TET2 | ENST00000380013 | NM_001127208.1 | c.3056delT | p.V1019GfsX14 | | |
| TET2 | ENST00000380013 | NM_001127208.1 | c.3130A>T | p.K1044* | YES | |
| TET2 | ENST00000380013 | NM_001127208.1 | c.3245_3246delAG | p.E1082AfsX21 | YES | |
| TET2 | ENST00000380013 | NM_001127208.1 | c.3311_3315delTTATA | p.F1104* | | |
| TET2 | ENST00000380013 | NM_001127208.1 | c.3316G>T | p.E1106* | | |
| TET2 | ENST00000380013 | NM_001127208.1 | c.3350A>G | p.K1117R | | |
| TET2 | ENST00000380013 | NM_001127208.1 | c.3365dupC | p.P11231TfsX7 | | |
| TET2 | ENST00000380013 | NM_001127208.1 | c.3404G>A | p.C1135Y | YES | |
| TET2 | ENST00000380013 | NM_001127208.1 | c.3493G>A | p.E1165K | YES | YES |
| TET2 | ENST00000380013 | NM_001127208.1 | c.3499A>G | p.R1167G | YES | |
| TET2 | ENST00000380013 | NM_001127208.1 | c.3526A>G | p.R1176G | YES | |
| TET2 | ENST00000380013 | NM_001127208.1 | c.3532delG | p.E1178KfsX48 | | |
| TET2 | ENST00000380013 | NM_001127208.1 | c.3577T>A | p.C1193S | YES | |
| TET2 | ENST00000380013 | NM_001127208.1 | c.3579T>G | p.C1193W | | |
| TET2 | ENST00000380013 | NM_001127208.1 | c.3589_3594+23delAAGTGGGTAAGTGTGACTTGATAAAGCCT | Splice Disruption | | |
| TET2 | ENST00000380013 | NM_001127208.1 | c.3594+5G>A | Splice Disruption | YES | |
| TET2 | ENST00000380013 | NM_001127208.1 | c.3646C>T | p.R1216* | | |
| TET2 | ENST00000380013 | NM_001127208.1 | c.3732_3733delCT | p.Y1245LfsX22 | YES | |
| TET2 | ENST00000380013 | NM_001127208.1 | c.3726_3757dupCAAACTCTACTCGGAGCTTACCGAGACGCTGA | p.R1253TfsX11 | | |
| TET2 | ENST00000380013 | NM_001127208.1 | c.3781C>T | p.R1261C | YES | |
| TET2 | ENST00000380013 | NM_001127208.1 | c.3782G>A | p.R1261H | YES | |
| TET2 | ENST00000380013 | NM_001127208.1 | c.3797A>G | p.N1266S | | |

TABLE 3-continued

List of mutations predicted to disrupt protein sequence and included in the analysis.

| Gene Name | Ensembl Reference Transcript | RefSeq Reference Transcript | DNA Mutation | Protein Mutation | Confirmed Somatic in One or More Samples | Present in Two or More Samples |
|---|---|---|---|---|---|---|
| TET2 | ENST00000380013 | NM_001127208.1 | c.3803+5G>A | Splice Disruption | YES | |
| TET2 | ENST00000380013 | NM_001127208.1 | c.3845G>A | p.G1282D | | |
| TET2 | ENST00000380013 | NM_001127208.1 | c.3869C>G | p.S1290* | | |
| TET2 | ENST00000380013 | NM_001127208.1 | c.3893G>A | p.C1298Y | | |
| TET2 | ENST00000380013 | NM_001127208.1 | c.3894dupT | p.K1299* | | YES |
| TET2 | ENST00000380013 | NM_001127208.1 | c.3899_3909delTTGCCAGAAGC | p.F1300* | | |
| TET2 | ENST00000380013 | NM_001127208.1 | c.3899T>C | p.F1300S | | |
| TET2 | ENST00000380013 | NM_001127208.1 | c.3941A>G | p.D1314G | | |
| TET2 | ENST00000380013 | NM_001127208.1 | c.3936delT | p.D1314MfsX49 | | |
| TET2 | ENST00000380013 | NM_001127208.1 | c.3954+1G>T | Splice Disruption | YES | |
| TET2 | ENST00000380013 | NM_001127208.1 | c.3955−2A>G | Splice Disruption | YES | |
| TET2 | ENST00000380013 | NM_001127208.1 | c.3965T>C | p.L1322P | YES | |
| TET2 | ENST00000380013 | NM_001127208.1 | c.3986T>A | p.L1329Q | | |
| TET2 | ENST00000380013 | NM_001127208.1 | c.3998T>A | p.M1333K | | |
| TET2 | ENST00000380013 | NM_001127208.1 | c.4015A>T | p.K1339* | YES | |
| TET2 | ENST00000380013 | NM_001127208.1 | c.4044+1G>T | Splice Disruption | | |
| TET2 | ENST00000380013 | NM_001127208.1 | c.4104C>G | p.F1368L | | |
| TET2 | ENST00000380013 | NM_001127208.1 | c.4138C>T | p.H1380Y | | |
| TET2 | ENST00000380013 | NM_001127208.1 | c.4151A>G | p.D1384G | | |
| TET2 | ENST00000380013 | NM_001127208.1 | c.4178C>T | p.T1393I | YES | |
| TET2 | ENST00000380013 | NM_001127208.1 | c.4206_4212delCAATCGA | p.D1402EfsX44 | | |
| TET2 | ENST00000380013 | NM_001127208.1 | c.4210C>T | p.R1404* | YES | YES |
| TET2 | ENST00000380013 | NM_001127208.1 | c.4350delT | p.R1451GfsX7 | YES | |
| TET2 | ENST00000380013 | NM_001127208.1 | c.4393C>T | p.R1465* | | YES |
| TET2 | ENST00000380013 | NM_001127208.1 | c.4537+1G>A | Splice Disruption | | |
| TET2 | ENST00000380013 | NM_001127208.1 | c.4546C>T | p.R1516* | YES | YES |
| TET2 | ENST00000380013 | NM_001127208.1 | c.4579C>T | p.Q1527* | | |
| TET2 | ENST00000380013 | NM_001127208.1 | c.4609C>T | p.Q1537* | YES | |
| TET2 | ENST00000380013 | NM_001127208.1 | c.4639C>T | p.Q1547* | YES | |
| TET2 | ENST00000380013 | NM_001127208.1 | c.4748C>A | p.S1583* | YES | |
| TET2 | ENST00000380013 | NM_001127208.1 | c.4767T>A | p.Y1589* | YES | |
| TET2 | ENST00000380013 | NM_001127208.1 | c.4740_4780dupAAACTCTTCACACACTTCAGATATCTATGGAAGCACCAGCC | p.P1594QfsX16 | YES | |
| TET2 | ENST00000380013 | NM_001127208.1 | c.4870C>T | p.Q1624* | | |
| TET2 | ENST00000380013 | NM_001127208.1 | c.4938_4948delGGTTCCTATTinsCAG | p.G1647SfsX11 | | |
| TET2 | ENST00000380013 | NM_001127208.1 | c.5059C>T | p.Q1687* | | |
| TET2 | ENST00000380013 | NM_001127208.1 | c.5173C>A | p.P1725T | YES | |
| TET2 | ENST00000380013 | NM_001127208.1 | c.5197_5224delTTCATGGGAGCCACCTCTAGATTACCAC | p.F1733PfsX3 | YES | |
| TET2 | ENST00000380013 | NM_001127208.1 | c.5303C>T | p.A1768V | | |
| TET2 | ENST00000380013 | NM_001127208.1 | c.5363_5367dupACATG | p.L1790TfsX32 | YES | |
| TET2 | ENST00000380013 | NM_001127208.1 | c.5393C>G | p.S1798* | | |
| TET2 | ENST00000380013 | NM_001127208.1 | c.5518_5519delGCinsTG | p.A1840S | | |
| TET2 | ENST00000380013 | NM_001127208.1 | c.5582G>T | p.G1861V | | |
| TET2 | ENST00000380013 | NM_001127208.1 | c.5643T>A | p.H1881Q | | |
| TET2 | ENST00000380013 | NM_001127208.1 | c.5650A>G | p.T1884A | YES | YES |
| TET2 | ENST00000380013 | NM_001127208.1 | c.5690T>G | p.I1897S | YES | |
| TET2 | ENST00000380013 | NM_001127208.1 | c.5734C>G | p.H1912D | YES | |

TABLE 3-continued

List of mutations predicted to disrupt protein sequence and included in the analysis.

| Gene Name | Ensembl Reference Transcript | RefSeq Reference Transcript | DNA Mutation | Protein Mutation | Confirmed Somatic in One or More Samples | Present in Two or More Samples |
|---|---|---|---|---|---|---|
| TET2 | ENST00000380013 | NM_001127208.1 | c.5577G>A | p.R1926H | | |
| TET2 | ENST00000380013 | NM_001127208.1 | c.5885C>T | p.P1962L | | |
| TP53 | ENST00000445888 | NM_000546.4 | c.97T>C | p.S33P | YES | |
| TP53 | ENST00000445888 | NM_000546.4 | c.376−1G>A | Splice Disruption | YES | |
| TP53 | ENST00000445888 | NM_000546.4 | c.389T>A | p.L130H | YES | |
| TP53 | ENST00000445888 | NM_000546.4 | c.395A>T | p.K132M | | |
| TP53 | ENST00000445888 | NM_000546.4 | c.406C>T | p.Q136* | YES | |
| TP53 | ENST00000445888 | NM_000546.4 | c.437G>A | p.W146* | YES | |
| TP53 | ENST00000445888 | NM_000546.4 | c.467G>C | p.R156P | YES | |
| TP53 | ENST00000445888 | NM_000546.4 | c.473_483delGCGCCATGGCC | p.R158HfsX19 | YES | |
| TP53 | ENST00000445888 | NM_000546.4 | c.475G>C | p.A159P | YES | |
| TP53 | ENST00000445888 | NM_000546.4 | c.476C>T | p.A159V | | |
| TP53 | ENST00000445888 | NM_000546.4 | c.487T>C | p.Y163H | | |
| TP53 | ENST00000445888 | NM_000546.4 | c.488A>G | p.Y163C | | |
| TP53 | ENST00000445888 | NM_000546.4 | c.493C>T | p.Q165* | YES | YES |
| TP53 | ENST00000445888 | NM_000546.4 | c.535C>T | p.H179Y | YES | |
| TP53 | ENST00000445888 | NM_000546.4 | c.536C>G | p.H179R | | |
| TP53 | ENST00000445888 | NM_000546.4 | c.537T>G | p.H179Q | | |
| TP53 | ENST00000445888 | NM_000546.4 | c.559+2T>G | Splice Disruption | YES | |
| TP53 | ENST00000445888 | NM_000546.4 | c.578A>G | p.H193R | YES | |
| TP53 | ENST00000445888 | NM_000546.4 | c.659A>G | p.Y220C | YES | |
| TP53 | ENST00000445888 | NM_000546.4 | c.660T>G | p.Y220* | | |
| TP53 | ENST00000445888 | NM_000546.4 | c.672+1G>A | Splice Disruption | | |
| TP53 | ENST00000445888 | NM_000546.4 | c.713G>A | p.C238Y | YES | |
| TP53 | ENST00000445888 | NM_000546.4 | c.734G>A | p.G245D | YES | |
| TP53 | ENST00000445888 | NM_000546.4 | c.734G>C | p.G245A | YES | |
| TP53 | ENST00000445888 | NM_000546.4 | c.742C>T | p.R248W | YES | YES |
| TP53 | ENST00000445888 | NM_000546.4 | c.743G>A | p.R248Q | | |
| TP53 | ENST00000445888 | NM_000546.4 | c.783dupT | p.G262WfsX2 | | |
| TP53 | ENST00000445888 | NM_000546.4 | c.814G>A | p.V272M | YES | |
| TP53 | ENST00000445888 | NM_000546.4 | c.862_863delAAinsT | p.N288FfsX57 | YES | |
| TP53 | ENST00000445888 | NM_000546.4 | c.917_919+13delGAGGTAAGCAAGCAGGinsAGT | Splice Disruption | | |
| TP53 | ENST00000445888 | NM_000546.4 | c.920−1G>A | Splice Disruption | | |
| TP53 | ENST00000445888 | NM_000546.4 | c.920−2A>G | Splice Disruption | YES | YES |
| TP53 | ENST00000445888 | NM_000546.4 | c.949C>T | p.C>317* | | |
| TP53 | ENST00000445888 | NM_000546.4 | c.1007delA | p.E336GfsX9 | | |
| KDM6A | ENST00000377967 | NM_021140.2 | c.1751C>T | p.T584M | | |
| KDM6A | ENST00000377967 | NM_021140.2 | c.2331T>A | p.N777K | | |
| KDM6A | ENST00000377967 | NM_021140.2 | c.4093A>G | p.T1365A | | |

TABLE 4

List of mutations proven to be or previously reported as germline and not included in dbSNp.

| Gene Name | Ensembl Reference Transcript | RefSeq Reference Transcript | DNA Mutation | Protein Mutation | Reason for Exclusion | Present in Two or More Samples |
|---|---|---|---|---|---|---|
| ASXL1 | ENST00000375687 | NM_015338.5 | c.1181G>A | p.R394H | Identified in Germline | |
| ASXL1 | ENST00000375687 | NM_015338.5 | c.1465C>G | p.R489G | Identified in Germline | |
| ASXL1 | ENST00000375687 | NM_015338.5 | c.1720-3C>G | Splice Disruption | Identified in Germline | |
| ASXL1 | ENST00000375687 | NM_015338.5 | c.2468T>C | p.L823S | Identified in Germline | |
| ASXL1 | ENST00000375687 | NM_015338.5 | c.2957A>G | p.N986S | Identified in Germline | YES |
| ASXL1 | ENST00000375687 | NM_015338.5 | c.3498C>G | p.S1166R | Identified in Germline | YES |
| ASXL1 | ENST00000375687 | NM_015338.5 | c.3745A>G | p.M1249V | Previously Reported as Germline | |
| ASXL1 | ENST00000375687 | NM_015338.5 | c.3935C>T | p.A1312V | Identified in Germline | |
| ASXL1 | ENST00000375687 | NM_015338.5 | c.4099G>A | p.V1367I | Identified in Germline | |
| ASXL1 | ENST00000375687 | NM_015338.5 | c.4189G>A | p.G1397S | Identified in Germline | |
| CDH1 | ENST00000261769 | NM_004360.3 | c.1849G>A | p.A617T | Identified in Germline | YES |
| CDKN2A | ENST00000304494 | NM_000077.3 | c.47T>C | p.L16P | Identified in Germline | |
| CDKN2A | ENST00000304494 | NM_000077.3 | c.146T>C | p.I49T | Identified in Germline | |
| CDKN2A-p16INK4A/p14ARF | ENST00000304494/ ENST00000361570 | NM_000077.3/ NM_058195.2 | c.205C>A/ c.371G>A | p.E69K/p.G124E | Identified in Germline | |
| CDKN2A | ENST00000361570 | NM_058195.2 | c.290G>A | p.G97E | Identified in Germline | |
| EGFR | ENST00000275493 | NM_005228.3 | c.2369C>T | p.T790M | Identified in Germline | |
| ETV6 | ENST00000266427 | NM_001987.4 | c.672C>G | p.H224Q | Identified in Germline | |
| EZH2 | ENST00000320356 | NM_004456.3 | c.965A>G | p.N322S | Identified in Germline | |
| MET | ENST00000318493 | NM_001127500.1 | c.504G>T | p.E168D | Identified in Germline | YES |
| PTEN | ENST00000371953 | NM_000314.4 | c.235G>A | p.A79T | Identified in Germline | |
| RUNX1 | ENST00000300305 | NM_001754.4 | c.155T>A | p.M52K | Identified in Germline | |
| RUNX1 | ENST00000300305 | NM_001754.4 | c.167T>C | p.L56S | Previously Reported as Germline | YES |
| RUNX1 | ENST00000300305 | NM_001754.4 | c.733C>T | p.P245S | Identified in Germline | |
| TET2 | ENST00000380013 | NM_001127208.1 | c.100C>T | p.L34F | Previously Reported as Germline | YES |
| TET2 | ENST00000380013 | NM_001127208.1 | c.5666C>T | p.I889L | Identified in Germline | |
| TET2 | ENST00000380013 | NM_001127208.1 | c.1285G>A | p.G429R | Identified in Germline | |
| TET2 | ENST00000380013 | NM_001127208.1 | c.1379C>T | p.S460F | Identified in Germline | |
| TET2 | ENST00000380013 | NM_001127208.1 | c.2599T>C | p.Y867H | Previously Reported as Germline | YES |
| TET2 | ENST00000380013 | NM_001127208.1 | c.3251A>C | p.Q1084P | Previously Reported as Germline | YES |
| TET2 | ENST00000380013 | NM_001127208.1 | c.3255_3257delAAC | p.T1085del | Identified in Germline | |
| TET2 | ENST00000380013 | NM_001127208.1 | c.5152G>T | p.V1718L | Identified in Germline | YES |
| TET2 | ENST00000380013 | NM_001127208.1 | c.5167C>T | p.I723S | Previously Reported as Germline | YES |
| TET2 | ENST00000380013 | NM_001127208.1 | c.5449C>A | p.H1817N | Identified in Germline | |
| TP53 | ENST00000445888 | NM_000546.4 | c.704A>G | p.N235S | Identified in Germline | |
| KDM6A | ENST00000377967 | NM_021140.2 | c.1843C>G | p.L615V | Identified in Germline | |

TABLE 5

Coincidence of Mutations: This table shows the number of samples that had mutations in any given pair of genes. The gray-shaded cells on the diagonal show the number of samples that only have mutations in that gene. Cells in the top row list the total number of samples with a mutation in the gene listed in that column. Samples with more than two mutations will be counted in more than one cell per row and column. Therefore, the total number of mutation pairs (listed in the bottom row) may be greater than number of mutated samples shown inthe top row.

| | N | | | | | | | | |
|---|---|---|---|---|---|---|---|---|---|
| | 90 | 63 | 38 | 33 | 28 | 19 | 16 | 12 | 10 |
| | TET2 | ASXL1 | RUNX1 | TP53 | EZH2 | NRAS | JAK2 | ETV6 | CBL |
| TET2 | 46 | 18 | 12 | 7 | 7 | 7 | 3 | 2 | 7 |
| ASXL1 | 18 | 22 | 13 | 1 | 14 | 4 | 3 | 2 | 5 |
| RUNX1 | 12 | 13 | 14 | | 8 | 6 | | | 1 |
| TP53 | 7 | 1 | | 23 | 2 | | | 1 | |
| EZH2 | 7 | 14 | 8 | 2 | 6 | 2 | | 1 | 1 |
| NRAS | 7 | 4 | 6 | | 2 | 3 | | | |
| JAK2 | 3 | 3 | | | | | 6 | 1 | |
| ETV6 | 2 | 2 | | 1 | 1 | | 1 | 4 | |
| CBL | 7 | 5 | 1 | | 1 | | | | 2 |
| IDH2 | 1 | 4 | | | 1 | | 1 | | 2 |
| NPM1 | 1 | | | | | | | | |
| IDH1 | | 3 | | | 1 | 1 | | | |

TABLE 5-continued

Coincidence of Mutations: This table shows the number of samples that had mutations in any given pair of genes. The gray-shaded cells on the diagonal show the number of samples that only have mutations in that gene. Cells in the top row list the total number of samples with a mutation in the gene listed in that column. Samples with more than two mutations will be counted in more than one cell per row and column. Therefore, the total number of mutation pairs (listed in the bottom row) may be greater than number of mutated samples shown in the top row.

|  |  |  |  |  |  |  |  |  |
|---|---|---|---|---|---|---|---|---|
| KRAS | 2 | 1 | 1 |  | 1 |  |  |  |
| GNAS |  |  |  |  |  |  | 1 |  |
| PTPN11 |  |  | 1 |  | 1 |  | 1 |  |
| BRAF |  |  |  |  |  |  |  |  |
| PTEN | 1 |  | 1 |  |  |  |  |  |
| CDKN2A |  |  |  |  |  |  |  |  |
| TOTAL | 115 | 90 | 56 | 36 | 43 | 25 | 14 | 13 | 18 |

| N |
|---|

|  | 9 IDH2 | 8 NPM1 | 6 IDH1 | 4 KRAS | 3 GNAS | 3 PTPN11 | 2 BRAF | 1 PTEN | 1 CDKN2A |
|---|---|---|---|---|---|---|---|---|---|
| TET2 | 1 | 1 |  | 2 |  |  |  | 1 |  |
| ASXL1 | 4 |  | 3 | 1 |  |  |  |  |  |
| RUNX1 |  |  |  | 1 |  | 1 |  |  |  |
| TP53 |  |  |  |  |  |  |  | 1 |  |
| EZH2 | 1 |  | 1 |  |  |  |  |  |  |
| NRAS |  |  | 1 | 1 |  | 1 |  |  |  |
| JAK2 | 1 |  |  |  |  |  |  |  |  |
| ETV6 |  |  |  |  | 1 | 1 |  |  |  |
| CBL | 2 |  |  |  |  |  |  |  |  |
| IDH2 | 2 |  |  |  | 1 |  |  |  |  |
| NPM1 |  | 6 |  |  |  |  |  |  |  |
| IDH1 |  |  | 3 |  |  |  |  |  |  |
| KRAS |  |  |  | 2 |  |  |  |  |  |
| GNAS | 1 |  |  |  | 1 |  |  |  |  |
| PTPN11 |  |  |  |  |  | 1 |  |  |  |
| BRAF |  |  |  |  |  |  | 2 |  |  |
| PTEN |  |  |  |  |  |  |  |  |  |
| CDKN2A |  |  |  |  |  |  |  |  | 1 |
| TOTAL | 12 | 8 | 8 | 7 | 3 | 4 | 2 | 2 | 1 |

TABLE 6

Frequency of Mutated Genes and Association with Median Survival.

|  | N (%) | Median Survival years (95% CI) | p-value |
|---|---|---|---|
| All Samples | 439 | 1.86 (1.60, 2.14) |  |
| Mutation Type |  |  |  |
| TET2 | 90 (21) | 1.88 (1.26, 2.55) | 0.48 |
| ASXL1 | 63 (14) | 1.33 (0.96, 1.88) | 0.003 |
| RUNX1 | 38 (9) | 1.16 (0.77, 1.53) | <0.001 |
| TP53 | 33 (8) | 0.65 (0.44, 1.10) | <0.001 |
| EZH2 | 28 (6) | 0.79 (0.67, 1.40) | <0.001 |
| NRAS | 16 (4) | 1.03 (0.44, 1.98) | 0.006 |
| JAK2 | 13 (3) | 2.14 (1.02, 3.12) | 0.96 |
| ETV6 | 12 (3) | 0.83 (0.62, 2.29) | 0.043 |
| CBL | 10 (2) | 1.52 (0.14, 1.71) | 0.018 |
| IDH2 | 9 (2) | 1.58 (0.50, 2.14) | 0.027 |
| NPM1 | 8 (2) | 2.18 (0.59, 2.74) | 0.43 |
| IDH1 | 6 (1) | 3.30 (0.35, 9.52) | 0.52 |
| KRAS | 4 (1) | 0.89 (0.36, 7.44) | 0.54 |
| GNAS | 3 (<1) |  |  |
| PTPN11 | 3 (<1) |  |  |
| BRAF | 2 (<1) |  |  |
| PTEN | 1 (<1) |  |  |
| CDKN2A | 1 (<1) |  |  |
| DNMT3A |  |  |  |
| SF3B1 |  |  |  |

TABLE 7

Mutations and Prognosis in a Multivariable Survival Model.

|  | HR (95% CI) | p-value |
|---|---|---|
| Age |  |  |
| ≥55 yrs vs. <55 yrs | 1.81 (1.20-2.73) | 0.004 |
| IPSS Risk Group |  |  |
| Int1 vs. Low | 2.29 (1.69-3.11) | <0.001 |
| Int2 vs. Low | 3.45 (2.42-4.91) | <0.001 |
| High vs. Low | 5.85 (3.63-9.40) | <0.001 |
| Mutational Status |  |  |
| TP53 Mutation Present vs. Absent | 2.48 (1.60-3.84) | <0.001 |
| EZH2 Mutation Present vs. Absent | 2.13 (1.36-3.33) | <0.001 |
| ETV6 Mutation Present vs. Absent | 2.04 (1.08-3.86) | 0.029 |
| RUNX1 Mutation Present vs. Absent | 1.47 (1.01-2.15) | 0.047 |
| ASXL1 Mutation Present vs. Absent | 1.38 (1.00-1.89) | 0.049 |

TABLE 8

Lower Risk Prognostic Scoring System (LR-PSS)

| Clinical Variables | Points |
|---|---|
| Unfavorable Cytogenetics: not normal or del(5q) alone | 1 |
| Age ≥60 years | 2 |
| Hemoglobin <10 g/dl | 1 |

TABLE 8-continued

Lower Risk Prognostic Scoring System (LR-PSS)

| Platelet Count | |
|---|---|
| <50,000 per μl | 2 |
| 50,000-200,000 per μl | 1 |
| Bone Marrow Blasts ≥4% | 1 |

| Risk Group Assignment | Total Points |
|---|---|
| Category 1 | 0-2 |
| Category 2 | 3-4 |
| Category 3 | 5-7 |

TABLE 9

Univariate and Adjusted Hazard Ratios Associated With Mutations in 15 Genes.

| | N (%) | Univariate HR (95% CI) | p-value | IPSS Adjusted HR (95% CI) | p-value | LR-PSS Adjusted HR (95% CI) | p-value |
|---|---|---|---|---|---|---|---|
| N | 288 | | | | | | |
| Mutation Type | | | | | | | |
| TET2 | 65 (23) | 1.35 (0.97, 1.86) | 0.073 | 1.28 (0.92, 1.77) | 0.14 | 1.05 (0.75, 1.46) | 0.78 |
| SF3B1 | 64 (22) | 0.76 (0.55, 1.07) | 0.12 | 0.80 (0.57, 1.12) | 0.19 | 0.98 (0.69, 1.39) | 0.89 |
| ASXL1 | 43 (15) | 2.06 (1.44, 2.94) | <0.001 | 1.88 (1.31, 2.69) | <0.001 | 1.56 (1.08, 2.26) | 0.019 |
| U2AF1 | 46 (16) | 1.49 (1.05, 2.11) | 0.027 | 1.46 (1.03, 2.08) | 0.034 | 1.20 (0.84, 1.72) | 0.31 |
| SRSF2 | 42 (13) | 1.54 (1.08, 2.18) | 0.017 | 1.35 (0.94, 1.93) | 0.10 | 1.37 (0.96, 1.96) | 0.08 |
| DNM3TA | 36 (13) | 1.03 (0.66, 1.61) | 0.89 | 1.07 (0.69, 1.66) | 0.77 | 1.12 (0.72 1.76) | 0.61 |
| RUNX1 | 25 (9) | 2.43 (1.58, 3.74) | <0.001 | 2.26 (1.47, 3.49) | <0.001 | 1.67 (1.07, 2.61) | 0.024 |
| EZH2 | 23 (8) | 3.10 (1.99, 4.83) | <0.001 | 3.36 (2.15, 5.25) | <0.001 | 2.90 (1.85, 4.52) | <0.001 |
| JAK2 | 9 (3) | 1.75 (0.89, 3.43) | 0.10 | 1.31 (0.67, 2.58) | 0.44 | 1.54 (0.78, 3.02) | 0.21 |
| NRAS | 8 (3) | 3.42 (1.68, 6.98) | <0.001 | 2.60 (1.27, 5.32) | 0.009 | 1.60 (0.76, 3.35) | 0.22 |
| TP53 | 7 (2) | 2.24 (0.99, 5.09) | 0.054 | 2.43 (1.07, 5.52) | 0.034 | 2.63 (1.16, 5.99) | 0.021 |
| ETV6 | 6 (2) | 1.28 (0.47, 3.44) | 0.63 | 1.18 (0.44, 3.19) | 0.74 | 0.76 (0.28, 2.07) | 0.59 |
| CBL | 5 (2) | 1.88 (0.77, 4.60) | 0.17 | 1.43 (0.58, 3.50) | 0.44 | 0.85 (0.34, 2.12) | 0.73 |
| NPM1 | 5 (2) | 2.38 (0.88, 6.46) | 0.089 | 1.83 (0.67, 4.99) | 0.24 | 2.08 (0.77, 5.67) | 0.15 |
| IDH1 | 5 (2) | 1.07 (0.44, 2.60) | 0.89 | 0.74 (0.30, 1.81) | 0.50 | 1.00 (0.41, 2.44) | 0.99 |

TABLE 10

Multivariable Overall Survival Models for IPSS and LR-PSS.

| Variable | HR (95% CI) | p-value |
|---|---|---|
| Model I - IPSS, Age, Sex, and Mutation Status | | |
| Age ≥60 vs. <60 yrs | 1.61 (1.09-2.37) | 0.017 |
| IPSS Risk Classification | | |
| Intermediate-1 vs. Low | 2.28 (1.67-3.12) | <0.001 |
| Mutational Status | | |
| EZH2 Present vs. Absent | 2.93 (1.84-4.67) | <0.001 |
| NRAS Present vs. Absent | 2.56 (1.24-5.29) | 0.011 |
| ASXL1 Present vs. Absent | 1.60 (1.10-2.34) | 0.014 |
| Model II - LR-PSS, Sex, and Mutation Status | | |
| LR-PSS Classification | | |
| Category 2 vs. 1 | 1.98 (1.28-3.06) | 0.002 |
| Category 3 vs. 1 | 4.92 (3.05-7.93) | <0.001 |
| Mutational Status | | |
| EZH2 Present vs. Absent | 2.90 (1.85-4.52) | <0.001 |

29% of cases have LR-PSS Category 3 risk or EZH2 mutations.

TABLE 11

Patient Characteristics

| | N (%) |
|---|---|
| N | 288 |
| Age at Time of BM Sample (yrs.), median (range) | 69 (15, 90) |
| Sex | |
| Female | 85 (30) |
| Male | 203 (70) |
| FAB | |
| RA | 173 (60) |
| RARS | 41 (14) |
| RAEB | 71 (25) |
| RAEB-T† | 3 (1) |
| IPSS | |
| Low | 106 (37) |
| Intermediate-1 | 182 (63) |
| Red Blood Cell Transfusion | |
| Yes | 131 (45) |
| No | 111 (39) |
| Unknown | 46 (16) |
| Platelet Transfusion | |
| Yes | 39 (14) |
| No | 200 (69) |
| Unknown | 49 (17) |
| Karyotype | |
| −7/del(7q) isolated or +1 | 1 (<1) |
| Del(20q) isolated | 14 (5) |
| Del(5q) isolated | 18 (6) |
| +8 isolated | 13 (5) |
| Complex | 6 (2) |
| Normal | 206 (72) |
| Other | 30 (10) |
| Blast %, median (range) | 0 (0, 10) |
| <4% | 217 (75) |
| 4-10% | 71 (25) |

TABLE 11-continued

Patient Characteristics

| | N (%) |
|---|---|
| Hemoglobin, median (range) | 10.0 (6.1, 17.0) |
| <8.0 (gm/dl) | 30 (10) |
| 8.0-9.99 (gm/dl) | 114 (40) |
| 10.0-11.99 (gm/dl) | 96 (33) |
| ≥12.0 (gm/dl) | 48 (17) |
| Absolute Neutrophil Count (ANC), median (range) | 1,887 (19.8, 25,830) |
| <500 (cells/mm$^3$) | 26 (9) |
| 500-1,499 (cells/mm$^3$) | 87 (30) |
| 1,500-9,999 (cells/mm$^3$) | 155 (54) |
| ≥10,000 (cells/mm$^3$) | 6 (2) |
| Unknown | 14 (5) |
| Platelets, median (range) | 105 (3, 915) |
| <50 (×10$^9$/L) | 72 (25) |
| 50-200 (×10$^9$/L) | 136 (47) |
| >200 (×10$^9$/L) | 80 (28) |

TABLE 12

Assignments from IPSS Lower Risk Groups to LR-PSS Risk Categories

| | | LR-PSS Risk Category | | |
|---|---|---|---|---|
| | N | 1 | 2 | 3 |
| A. Mapping of IPSS Lower Risk Groups (n = 288) | | | | |
| IPSS Risk Group | Low | 38 | 67 | 1 |
| | Intermediate-1 | 19 | 93 | 70 |
| B. Mapping of IPSS Lower Risk Scores (n = 283)* | | | | |
| Total IPSS Score | 0 | 38 | 67 | 1 |
| | 0.5 | 13 | 70 | 27 |
| | 1.0 | 6 | 19 | 42 |

*5 patients with Intermediate-1 risk were excluded from this table because they had missing clinical information making it unclear if their total IPSS score was 0.5 or 1.0.

TABLE 13A

Multivariable COX Survival Models - From our original NEJM Paper

| Variable | HR (95% CI) | p-value |
|---|---|---|
| Age | | |
| ≥55 yrs vs. <55 yrs | 1.81 (1.20-2.73) | 0.004 |
| IPSS Risk Group | | |
| Int1 vs. Low | 2.29 (1.69-3.11) | <0.001 |
| Int2 vs. Low | 3.45 (2.42-4.91) | <0.001 |
| High vs. Low | 5.85 (3.63-9.40) | <0.001 |
| Mutational Status - Present vs. Absent | | |
| TP53 Mutation | 2.48 (1.60-3.84) | <0.001 |
| EZH2 Mutation | 2.13 (1.36-3.33) | <0.001 |
| ETV6 Mutation | 2.04 (1.08-3.86) | 0.029 |
| RUNX1 Mutation | 1.47 (1.01-2.15) | 0.047 |
| ASXL1 Mutation | 1.38 (1.00-1.89) | 0.049 |

137/439 (31.2%) samples carry one or more prognostic mutations

TABLE 13B

Multivariable COX Survival Models - With DNMT3A and Splice Genes included

| Variable | HR (95% CI) | p-value |
|---|---|---|
| Age | | |
| ≥55 yrs vs. <55 yrs | 1.77 (1.18-2.67) | 0.006 |
| IPSS Risk Group | | |
| Int1 vs. Low | 2.37 (1.74-3.21) | <0.001 |
| Int2 vs. Low | 3.65 (2.55-5.21) | <0.001 |
| High vs. Low | 6.60 (4.07-10.70) | <0.001 |
| Mutational Status - Present vs. Absent | | |
| EZH2 Mutation | 2.52 (1.63-3.89) | <0.001 |
| TP53 Mutation | 2.42 (1.57-3.74) | <0.001 |
| ETV6 Mutation | 1.96 (1.03-3.71) | 0.039 |
| RUNX1 Mutation | 1.47 (1.00-2.14) | 0.048 |
| DNMT3A Mutation | 1.42 (1.01-1.98) | 0.044 |
| U2AF1 Mutation | 1.38 (1.01-1.90) | 0.049 |

184/439 (41.9%) samples carry one or more prognostic mutations

EQUIVALENTS

Those skilled in the art will recognize, or be able to ascertain using no more than routine experimentation, numerous equivalents to the specific procedures described herein. Such equivalents are considered to be within the scope of the invention and are covered by the following claims. Various substitutions, alterations, and modifications may be made to the invention without departing from the spirit and scope of the invention as defined by the claims. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof.

REFERENCES

1. Ebert B L, Pretz J, Bosco J, et al. Identification of RPS14 as a 5q-syndrome gene by RNA interference screen. Nature 2008; 451:335-9.
2. Haase D, Germing U, Schanz J, et al. New insights into the prognostic impact of the karyotype in MDS and correlation with subtypes: evidence from a core dataset of 2124 patients. Blood 2007; 110:4385-95.
3. Bejar R, Levine R, Ebert B L. Unraveling the Molecular Pathophysiology of Myelodysplastic Syndromes. Journal of Clinical Oncology 2011; 29:504-15.
4. Greenberg P, Cox C, LeBeau M M, et al. International Scoring System for Evaluating Prognosis in Myelodysplastic Syndromes. Blood 1997; 89:2079-88.
5. Garcia-Manero G, Shan J, Faderl S, et al. A prognostic score for patients with lower risk myelodysplastic syndrome. Leukemia 2008; 22:538-43.
6. Malcovati L, Germing U, Kuendgen A, et al. Time-Dependent Prognostic Scoring System for Predicting Survival and Leukemic Evolution in Myelodysplastic Syndromes. J Clin Oncol 2007; 25:3503-10.
7. Pedersen-Bjergaard J, Andersen M K, Andersen M T, Christiansen D H. Genetics of therapy-related myelodysplasia and acute myeloid leukemia. Leukemia 2008; 22:240-8.

8. Horiike S, Kita-Sasai Y, Nakao M, Taniwaki M. Configuration of the TP53 Gene as an Independent Prognostic Parameter of Myelodysplastic Syndrome. Leukemia & Lymphoma 2003; 44:915-22.
9. Padua R A, Guinn B A, Al-Sabah A I, et al. RAS, FMS and p53 mutations and poor clinical outcome in myelodysplasias: a 10-year follow-up. Leukemia 1998; 12:887-92.
10. Paquette R L, Landaw E M, Pierre R V, et al. N-ras mutations are associated with poor prognosis and increased risk of leukemia in myelodysplastic syndrome. Blood 1993; 82:590-9.
11. Kosmider O, Gelsi-Boyer V, Cheok M, et al. TET2 mutation is an independent favorable prognostic factor in myelodysplastic syndromes (MDSs). Blood 2009; 114:3285-91.
12. Chen C Y, Lin L I, Tang J L, et al. RUNX1 gene mutation in primary myelodysplastic syndrome—the mutation can be detected early at diagnosis or acquired during disease progression and is associated with poor outcome. Br J Haematol 2007; 139:405-14.
13. Steensma D P, Gibbons R J, Mesa R A, Tefferi A, Higgs D R. Somatic point mutations in RUNX1/CBFA2/AML1 are common in high-risk myelodysplastic syndrome, but not in myelofibrosis with myeloid metaplasia. Eur J Haematol 2005; 74:47-53.
14. Pardanani A, Patnaik M M, Lasho T L, et al. Recurrent IDH mutations in high-risk myelodysplastic syndrome or acute myeloid leukemia with isolated del(5q). Leukemia 2010; 24:1370-2.
15. Kosmider O, Gelsi-Boyer V, Slama L, et al. Mutations of IDH1 and IDH2 genes in early and accelerated phases of myelodysplastic syndromes and MDS/myeloproliferative neoplasms. Leukemia 2010; 24:1094-6.
16. Kaneko H, Misawa S, Horiike S, Nakai H, Kashima K. TP53 mutations emerge at early phase of myelodysplastic syndrome and are associated with complex chromosomal abnormalities. Blood 1995; 85:2189-93.
17. Kita-Sasai Y, Horiike S, Misawa S, et al. International prognostic scoring system and TP53 mutations are independent prognostic indicators for patients with myelodysplastic syndrome. Br J Haematol 2001; 115:309-12.
18. Rocquain J, Carbuccia N, Trouplin V, et al. Combined mutations of ASXL1, CBL, FLT3, IDH1, IDH2, JAK2, KRAS, NPM1, NRAS, RUNX1, TET2 and WT1 genes in myelodysplastic syndromes and acute myeloid leukemias. BMC Cancer 2010; 10:401.
19. MacConaill L E, Campbell C D, Kehoe S M, et al. Profiling Critical Cancer Gene Mutations in Clinical Tumor Samples. PLoS ONE 2009; 4:e7887.
20. Badalian-Very G, Vergilio J-A, Degar B A, et al. Recurrent BRAF mutations in Langerhans cell histiocytosis. Blood:blood-2010-04-279083.
21. Thomas R K, Baker A C, Debiasi R M, et al. High-throughput oncogene mutation profiling in human cancer. Nat Genet 2007; 39:347-51.
22. Sekeres M A. The epidemiology of myelodysplastic syndromes. Hematol Oncol Clin North Am 2010; 24:287-94.
23. Sekeres M A, Schoonen W M, Kantarjian H, et al. Characteristics of US patients with myelodysplastic syndromes: results of six cross-sectional physician surveys. J Natl Cancer Inst 2008; 100:1542-51.
24. Rollison D E, Howlader N, Smith M T, et al. Epidemiology of myelodysplastic syndromes and chronic myeloproliferative disorders in the United States, 2001-2004, using data from the NAACCR and SEER programs. Blood 2008; 112:45-52.
25. Odero M D, Vizmanos J L, Roman J P, et al. A novel gene, MDS2, is fused to ETV6/TEL in a t(1; 12)(p36.1; p13) in a patient with myelodysplastic syndrome. Genes, Chromosomes and Cancer 2002; 35:11-9.
26. Silva F P G, Morolli B, Storlazzi C T, et al. ETV6 mutations and loss in AML-M0. Leukemia 2008; 22:1639-43.
27. Suarez H G, du Villard J A, Caillou B, Schlumberger M, Parmentier C, Monier R. gsp mutations in human thyroid tumours. Oncogene 1991; 6:677-9.
28. Kalfa N, Lumbroso S, Boulle N, et al. Activating Mutations of Gsα in Kidney Cancer. The Journal of Urology 2006; 176:891-5.
29. Wood L D, Parsons D W, Jones S, et al. The genomic landscapes of human breast and colorectal cancers. Science 2007; 318:1108-13.
30. Kan Z, Jaiswal B S, Stinson J, et al. Diverse somatic mutation patterns and pathway alterations in human cancers. Nature 2010; 466:869-73.
31. Smith A E, Mohamedali A M, Kulasekararaj A, et al. Next-generation sequencing of the TET2 gene in 355 MDS and CMML patients reveals low abundance mutant clones with early origins, but indicates no definite prognostic value. Blood 2010:blood-2010-03-274704.
32. Fisher C L, Pineault N, Brookes C, et al. Loss-of-function Additional sex combs like 1 mutations disrupt hematopoiesis but do not cause severe myelodysplasia or leukemia. Blood 2010; 115:38-46.
33. Ko M, Huang Y, Jankowska A M, et al. Impaired hydroxylation of 5-methylcytosine in myeloid cancers with mutant TET2. Nature 2010; 468:839-43.
34. Ernst T, Chase A J, Score J, et al. Inactivating mutations of the histone methyltransferase gene EZH2 in myeloid disorders. Nat Genet 2010; 42:722-6.

We claim:

1. A method of aggressively treating myelodysplastic syndrome (MDS) in a subject, the method comprising:
    (a) detecting whether one or more protein sequence-disrupting mutations is present in each of genes TP53, ETV6, EZH2, RUNX1 and ASXL1 in a polynucleotide sample obtained from a subject, using a nucleic acid detection assay;
    (b) diagnosing the subject as needing aggressive treatment for MDS when one or more mutations is detected in two or more of the TP53, ETV6, EZH2, RUNX1 and ASXL1 genes; and
    (c) administering an effective amount of an aggressive drug regimen comprising azacytidine, decitabine, lenalidomide, and/or bone marrow transplantation, to the subject diagnosed in step (b) to aggressively treat MDS.

2. The method of claim 1, wherein the presence of at least one mutation in two or more of the TP53, ETV6, EZH2, RUNX1 and ASXL1 genes indicates a decreased overall survival of the subject when compared to a subject without the mutation.

3. The method of claim 1, wherein the subject has refractory anemia with ring sideroblasts (RARS) type MDS.

4. The method of claim 1, wherein the International Prognostic Scoring System (IPSS) classification of the subject is low or intermediate risk MDS.

5. A method of aggressively treating myelodysplastic syndrome (MDS) in a subject selected for aggressive MDS therapy, the method comprising:
    (a) obtaining a biological sample from a subject at a first time point;

(b) assaying the sample of step (a) to detect the presence of one or more protein sequence-disrupting mutations in each of the TP53, ETV6, EZH2, RUNX1 and ASXL1 genes in the subject's sample at the first time point;

(c) obtaining a biological sample from the subject at a second time point;

(d) assaying the sample of step (c) to detect the presence of one or more protein sequence-disrupting mutations in each of the TP53, ETV6, EZH2, RUNX1 and ASXL1 genes in the subject's sample at the second time point;

(e) selecting the subject as needing aggressive therapy for MDS by detecting an increase in the frequency of occurrence of the one or more mutations in two or more of the TP53, ETV6, EZH2, RUNX1 and ASXL1 genes in the sample obtained at the second time point relative to the frequency of occurrence of the one or more mutations in two or more of the TP53, ETV5, EZH2, RUNX1 and ASXL1 genes in the sample obtained at the first time point; and administering an effective amount of an aggressive drug regimen comprising azacytidine, decitabine, lenalidomide, and/or bone marrow transplantation to the subject selected for aggressive MDS therapy based on step (e), thereby aggressively treating MDS in the subject.

6. The method of claim 5, wherein the subject has previously been treated for MDS.

7. The method of claim 5, wherein the sample obtained at the first time point is obtained from the subject prior to the subject being treated for MDS.

8. The method of claim 5, wherein the sample obtained at the second time point is obtained from the subject after the subject is treated for MDS.

9. The method of claim 5, wherein the one or more mutations is detected by a method selected from the group consisting of Next-Generation sequencing, Mass spectrometry genotyping, real time polymerase chain reaction, single nucleotide polymorphism (SNP) arrays, and interphase fluorescent in situ hybridization (FISH) analysis.

10. The method of claim 5, wherein the one or more mutations is not a silent mutation.

11. The method of claim 5, further comprising detecting at least one risk factor associated with MDS.

12. The method of claim 11, wherein the risk factor is International Prognostic Scoring System (IPSS) score.

13. The method of claim 5, wherein the sample obtained at the first time point or the sample obtained at the second time point is isolated from bone marrow or from a buccal swab of the subject.

14. The method of claim 5, wherein the one or more mutations is detected by Next-Generation genomic sequencing and/or Mass spectrometry genotyping.

15. A method of treating a subject having myelodysplastic syndrome (MDS), the method comprising:

(a) detecting one or more protein sequence-disrupting mutations in each of the TP53, ETV6, EZH2, RUNX1 and ASXL1 genes in a biological sample obtained from a subject by performing sequencing, hybridization, quantitative amplification, mass spectrometry genotyping, microplate array diagonal gel electrophoresis, oligonucleotide-specific ligation, invasive cleavage followed by mass spectrometry, immobilized padlock probes and rolling circle amplification, or a protein truncation test; and (b) administering to the subject an effective amount of azacytidine, decitabine, lenalidomide, and/or bone marrow transplantation following step (a), which detects the subject's risk for decreased or poor overall survival, thereby requiring aggressive treatment of MDS.

16. The method of claim 15, wherein the one or more mutations is detected by a method selected from the group consisting of Next-Generation sequencing, Mass spectrometry genotyping, real time polymerase chain reaction, single nucleotide polymorphism (SNP) arrays, and interphase fluorescent in situ hybridization (FISH) analysis.

17. The method of claim 15, wherein the one or more mutations is not a silent mutation.

18. The method of claim 15, further comprising detecting at least one MDS-associated risk factor, which is an International Prognostic Scoring System (IPSS) score.

19. The method of claim 1, wherein the biological sample is isolated from bone marrow or from a buccal swab of the subject.

20. The method of claim 15, wherein the biological sample is isolated from bone marrow or from a buccal swab of the subject.

21. The method of claim 1, wherein the one or more protein sequence-disrupting mutations in the TP53, ETV6, EZH2, RUNX1 and ASXL1 genes is set forth in Table 3.

22. The method of claim 5, wherein the one or more protein sequence-disrupting mutations in two or more of the TP53, ETV6, EZH2, RUNX1 and ASXL1 genes is set forth in Table 3.

23. The method of claim 15, wherein the one or more protein sequence-disrupting mutations in two or more of the TP53, ETV6, EZH2, RUNX1 and ASXL1 genes is set forth in Table 3.

24. A method of treating a patient for myelodysplastic syndrome (MDS), the method comprising:

(a) assaying a biological sample obtained from a patient for one or more protein sequence-disrupting mutations in each of the TP53, ETV6, EZH2, RUNX1 and ASXL1 genes, wherein the one or more protein sequence-disrupting mutations detected in two or more of the TP53, ETV6, EZH2, RUNX1 and ASXL1 genes is independently associated with decreased overall survival (OS) for MDS;

(b) selecting aggressive therapy for treating the patient having said one or more mutations detected in step (a); and (c) administering said aggressive therapy to treat MDS in the patient.

25. The method of claim 24, wherein the aggressive therapy for MDS comprises administering to the patient an effective amount of azacytidine, decitabine, lenalidomide, and/or bone marrow transplantation.

26. The method of claim 24, wherein the International Prognostic Scoring System (IPSS) classification of the patient is low or intermediate risk MDS.

27. The method of claim 24, wherein the one or more protein sequence-disrupting mutations in two or more of the TP53, ETV6, EZH2, RUNX1 and ASXL1 genes is set forth in Table 3.

28. The method of claim 24, wherein the patient's biological sample is a bone marrow or a buccal swab sample.

29. A method of stratifying a patient as at risk or not at risk for decreased overall survival (OS) from myelodysplastic syndrome (MDS) and treating the at risk patient with appropriate MDS therapy; the method comprising:

(a) assaying a biological sample obtained from an MDS patient for one or more protein-sequence disrupting mutations in each of the TP53, ETV6, EZH2, RUNX1 and ASXL1 genes;

(b) detecting in the patient's sample the one or more protein sequence-disrupting mutations in two or more of the TP53, ETV6, EZH2, RUNX1 and ASXL1 genes, wherein the one or more protein sequence-disrupting mutations is independently associated with decreased overall survival (OS);
(c) stratifying the patient as at risk for decreased OS based on step (b); and
(d) treating the patient of step (c) with an aggressive MDS therapy comprising one or more of azacytidine, decitabine, lenalidomide, and/or bone marrow transplantation.

30. The method of claim 29, wherein the one or more protein sequence-disrupting mutations in two or more of the TP53, ETV6, EZH2, RUNX1 and ASXL1 genes is set forth in Table 3.

31. The method of claim 29, wherein the patient's biological sample is a bone marrow or a buccal swab sample.

* * * * *